United States Patent
Qiu et al.

(10) Patent No.: US 11,730,545 B2
(45) Date of Patent: *Aug. 22, 2023

(54) SYSTEM AND METHOD FOR MULTI-CLIENT DEPLOYMENT OF AUGMENTED REALITY INSTRUMENT TRACKING

(71) Applicant: University Health Network, Toronto (CA)

(72) Inventors: Zigang Jimmy Qiu, Toronto (CA); Stefan Hofer, Toronto (CA); Blake Murphy, Toronto (CA); Tomas J. Saun, Toronto (CA); Lukasz Brzozowski, Mississauga (CA); Trinette Wright, Toronto (CA); Xun Lin, Toronto (CA)

(73) Assignee: University Health Network, Toronto (CA)

( * ) Notice: Subject to any disclaimer, the term of this patent is extended or adjusted under 35 U.S.C. 154(b) by 0 days.

This patent is subject to a terminal disclaimer.

(21) Appl. No.: 17/886,195

(22) Filed: Aug. 11, 2022

(65) Prior Publication Data
US 2022/0378510 A1    Dec. 1, 2022

Related U.S. Application Data

(63) Continuation of application No. 16/882,703, filed on May 25, 2020, now Pat. No. 11,413,094.
(Continued)

(51) Int. Cl.
*A61B 34/10* (2016.01)
*G06T 15/00* (2011.01)
(Continued)

(52) U.S. Cl.
CPC ............ *A61B 34/10* (2016.02); *G06T 15/005* (2013.01); *G06T 19/006* (2013.01); *A61B 2034/101* (2016.02); *G06T 15/06* (2013.01)

(58) Field of Classification Search
CPC .............. A61B 34/10; A61B 2034/101; G06T 15/005; G06T 15/06; G06T 19/006
See application file for complete search history.

(56) References Cited

U.S. PATENT DOCUMENTS

| | | | | |
|---|---|---|---|---|
| 6,477,580 | B1 * | 11/2002 | Bowman-Amuah | ..... G06F 9/54 709/236 |
| 2003/0058277 | A1 | 3/2003 | Bowman-Amuah | |

(Continued)

OTHER PUBLICATIONS

Chen et al., "Recent Developments and Future Challenges in Medical Mixed Reality", IEEE International Symposium on Mixed and Augmented Reality (ISMAR), 2017, pp. 1-13.
(Continued)

*Primary Examiner* — Michelle Chin
(74) *Attorney, Agent, or Firm* — Bereskin & Parr LLP/S.E.N.C.R.L., s.r.l.; Tonino Rosario Orsi; Ray Kovarik

(57) ABSTRACT

Methods and related systems and devices are described for performing various AR medical applications, including a method of guiding augmented reality (AR) intervention. In one aspect, a primary client device: receives model sets, an intervention plan having an intervention field, and session information about a session related to the AR intervention from a server; receives first real-time input data from a first input device; generates metrics by evaluating an execution of the intervention plan by comparing the intervention plan to the first real-time input data; displays real-time graphics, based at least in part on the metrics, spatially over the intervention field; receives real-time status data, from the server, about a replicate client device that joins the session;
(Continued)

sends the first real-time input data, the metrics and the evaluation computed from the intervention plan, through the server, to the replicate client device.

20 Claims, 44 Drawing Sheets

Related U.S. Application Data

(60) Provisional application No. 62/852,763, filed on May 24, 2019.

(51) Int. Cl.
*G06T 19/00* (2011.01)
*G06T 15/06* (2011.01)

(56) References Cited

U.S. PATENT DOCUMENTS

2017/0053540 A1* 2/2017 Meagher .................. G09B 5/00
2017/0124894 A1 5/2017 Essafi et al.

OTHER PUBLICATIONS

Kuhlemann et al., "Towards X-ray Free Endovascular Interventions—Using HoloLens for on-line holographic visualization", Healthc. Technol. Lett., Jul. 2017, pp. 1-4.
Kim et al., "Virtual Reality and Augmented Reality in Plastic Surgery: A Review", Arch. Plast. Surg., May 2017, 44(3), pp. 179-187.
Stefan et al., "A Mixed-Reality Approach to Radiation-Free Training of C-arm Based Surgery", Lecture Notes in Computer Science (including subseries Lecture Notes in Artificial Intelligence and Lecture Notes in Bioinformatics), LNCS, Springer Verlag, 2017,10434, pp. 540-547.
Nguyen et al., "Preliminary Development of Augmented Reality Systems for Spinal Surgery", Proc. of SPIE, 2017, 10050: 100500K-1 to -5.
Guha et al., "Augmented Reality in Neurosurgery: A Review of Current Concepts and Emerging Applications", Can. J. Neurol. Sci. / J. Can. des Sci. Neurol., May 2017, 44(3), pp. 235-245.
Zhang et al., "High-Quality See-Through Surgical Guidance System Using Enhanced 3-D Autostereoscopic Augmented Reality", IEEE Trans. Biomed. Eng., Aug. 2017, 64(8), pp. 1815-1825.
Qian et al., "Comprehensive Tracker Based Display Calibration for Holographic Optical See-Through Head-Mounted Display", arXiv, Computer Science, 2017 (8 pages).
Gasques Rodrigues et al., "Exploring Mixed Reality in Specialized Surgical Environments", Proceedings of the 2017 CHI Conference Extended Abstracts on Human Factors in Computing Systems—CHI EA '17, 2017, pp. 2591-2598.
Tepper et al., "Mixed Reality with HoloLens: Where Virtual Reality Meets Augmented Reality in the Operating Room", Plast. Reconstr. Surg., Nov. 2017, 140(5), pp. 1066-1070.
Cui et al., "Augmented Reality with Microsoft HoloLens Holograms for Near Infrared Fluorescence Based Image Guided Surgery", Proc. of SPIE, 2017, 11049: 1004901-1 to -6.
Perkins et al., "A Mixed-Reality System for Breast Surgical Planning", IEEE International Symposium on Mixed and Augmented Reality (ISMAR-Adjunct), 2017, pp. 269-274.
Qian et al., "Technical Note: Towards Virtual Monitors for Image Guided Interventions—Real-time Streaming to Optical See-Through Head Mounted Displays", arXiv, 2017 (6 pages).
Qian et al., "Comparison of Optical See-Through Head-Mounted Displays for Surgical Interventions with Object-Anchored 2D-Display", Int. J. Comput. Assist. Radiol. Surg., 2017, 12(6), pp. 901-910.
Meola et al., "Augmented Reality in Neurosurgery: A Systematic Review", Neurosurg. Rev., Oct. 2017, 40(4), pp. 537-548.
Rae et al., "Neurosurgical burr hole placement using the Microsoft HoloLens", Proc. of SPIE, 2018, 10576: 105760T-1 to -8.
Yoon et al., "Augmented reality for the surgeon: Systematic review", Int. J. Med. Robot. Comput. Assist. Surg., 2018, 14(4): e1914 (pp. 1-13).
Bosc et al., "Intraoperative augmented reality with heads-up displays in maxillofacial surgery: a systematic review of the literature and a classification of relevant technologies", International Journal of Oral and Maxillofacial Surgery, Churchill Livingstone, 2018/ 2019, 48(1): 132-139.
Wilkinson et al., "The FAIR Guiding Principles for scientific data management and stewardship", Scientific Data, 2016 3: 160018 (pp. 1-9).
Non-final Office Action and Notice of References Cited dated Nov. 26, 2021 in U.S. Appl. No. 16/882,703 (12 pages).

* cited by examiner

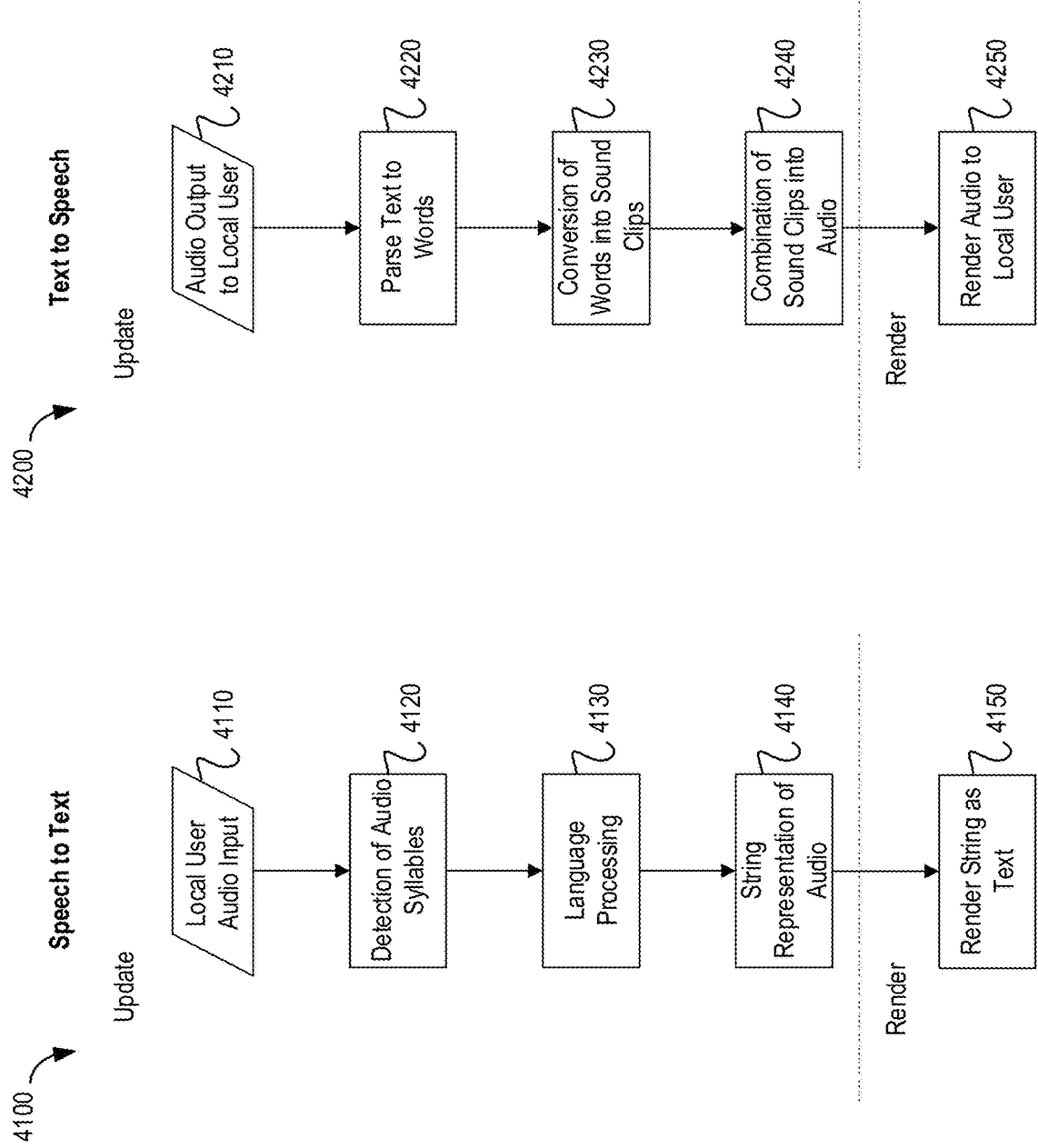

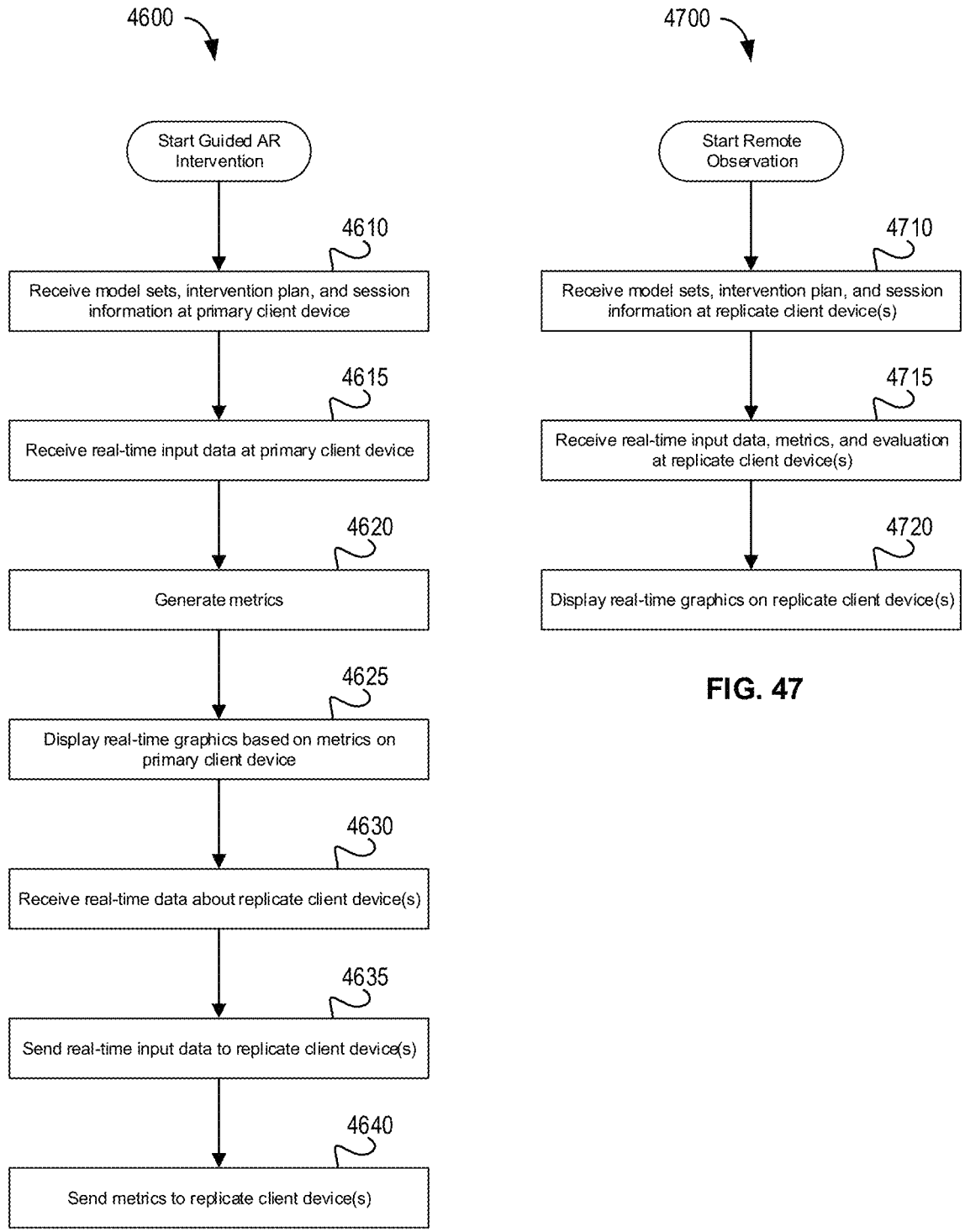

SYSTEM AND METHOD FOR MULTI-CLIENT DEPLOYMENT OF AUGMENTED REALITY INSTRUMENT TRACKING

CROSS-REFERENCES TO RELATED APPLICATIONS

The present utility patent application is a continuation of, and claims the priority benefit of, U.S. patent application Ser. No. 16/882,703 filed May 25, 2020, and entitled "System and Method for Multi-Client Deployment of Augmented Reality Instrument Tracking". U.S. patent application Ser. No. 16/882,703 in turn claims the benefit of U.S. Provisional Patent Application No. 62/852,763, filed May 24, 2019, and entitled "System and Method for Multi-Client Deployment of Augmented Reality Instrument Tracking". The entire contents of U.S. Provisional Patent Application No. 62/852,763 and U.S. patent application Ser. No. 16/882,703 are hereby incorporated by reference.

FIELD

Various embodiments are described herein that generally relate to a system and method for multi-client deployment of augmented reality instrument tracking.

BACKGROUND

The following paragraphs are provided by way of background to the present disclosure. They are not, however, an admission that anything discussed therein is prior art or part of the knowledge of persons skilled in the art.

Augmented reality (AR) is a technology where computer-generated information (e.g., imaging, sound, text, haptic feedback) is superimposed on a view of the real world, thus providing a composite "augmented" view of reality. The combination of AR with personalized surgery has the potential to improve planning, intervention, guidance, and education through quantitative and spatial feedback. As a spatial communication medium, it enables better application and dissemination of knowledge and expertise. Until recently, AR was limited to research facilities with specialized and expensive equipment. The current generation of AR devices have made advances in technological innovation, affordability, and portability. The AR experience relies on a combination of technologies to realize a personalized and contextual spatial experience. Recent progress in mobile computing with different sensor arrays has enabled AR experiences across smartphones and tablets. Many large technology companies appear to be committed to AR capabilities on their devices and platforms for years to come.

In head-mounted AR devices, there have been recent developments that mirror the past progress of Virtual Reality (VR) devices. The VR environment is completely virtual and computer-generated, unlike the AR environment where the goal is to enhance a person's actual reality by adding or superimposing additional information to better interact with certain tasks. VR devices are best known from gaming applications. Consumer VR first demonstrated immersive interactions by combining the computing power of modern desktop computers to render hi-fidelity stereoscopic renderings at a high refresh rate with a large field of view and motion tracking.

AR headsets take advantage of low-cost and low-power sensor arrays found in mobile devices with the technology advancements of VR. Current AR headsets are optical see-through devices that use beam combiners to route stereoscopic renderings of virtual objects to fuse with the real world. They use a comprehensive suite of sensors, such as accelerometers, gyroscopes, RGB+depth (RGB-D) cameras, and microphones, to digitize the real world in three dimensions (3D), with machine learning enabled interactivity from the user through voice and gestures. The technologies for the current generation of AR headsets are still maturing, but current AR devices are at a fraction of the previous cost. Common examples of the current generation of headsets include: HoloLens by Microsoft, and Google-backed Magic Leap.

AR has become a ubiquitous technology across devices and platforms potentially available to both clinicians and patients. As a malleable spatial medium that combines the virtual and real with evolving context, AR enables medical professionals to communicate and manage complexity encountered on a daily basis in personalized treatments. In personalized surgery, augmented reality may be a technical medium that can maximize clinical performance and improve patient outcomes.

AR also has the ability to combine different technologies such as multi-modal imaging, computer vision, computer graphics, navigation, human-machine interactions, and machine learning. It is able to fuse all the complex information from these technologies and present them in a spatially coherent and contextually relevant way. However, there are shortcomings in the current state of the art of AR as applied to the context of intervention and surgery.

SUMMARY OF VARIOUS EMBODIMENTS

Various embodiments of a system and method for multi-client deployment of augmented reality instrument tracking are provided according to the teachings herein that may be used in surgical planning, intervention, guidance, and/or education.

In one broad aspect, in accordance with the teachings herein, there is provided a computer-implemented method of guiding augmented reality (AR) intervention using a primary client device and a server, the primary client device having a first processor, the method comprising: receiving, at the primary client device, model sets, an intervention plan having an intervention field, and session information about a session related to the AR intervention from the server; receiving, at the primary client device, first real-time input data from the first input device; generating, at the first processor, metrics by determining an evaluation of an execution of the intervention plan by comparing the intervention plan to the first real-time input data; displaying, on the primary client device, real-time graphics, based at least in part on the metrics, spatially over the intervention field; receiving, at the primary client device, real-time status data, from the server, about a replicate client device connected to the server after the replicate client device joins the session; sending, from the primary client device, the first real-time input data, through the server, to the replicate client device within the session; sending, from the primary client device, the metrics and the evaluation computed from the intervention plan, through the server, to the replicate client device within the session; receiving, at the primary client device, second real-time input data from the server, the second real-time input data originating from the replicate client device and relating to the intervention plan; and displaying, at the primary client device, real-time graphics based at least in part on the second real-time input data from the replicate client device.

In at least one embodiment, for remotely observing the guided AR intervention using the replicate client device having a second processor and a second input device, the method further comprises: receiving, at the replicate client device, the model sets, the intervention plan, and the session information about the session related to the AR intervention from the server; receiving, at the replicate client device, the first real-time input data, the metrics, and the evaluation broadcasted from the primary client device; and displaying, on the replicate client device, real-time graphics based at least in part on the model sets, the intervention plan, the first real-time input data, the metrics, and the evaluation.

In at least one embodiment, for providing remote mentoring of the guided AR intervention, the method further comprises: receiving, at the replicate client device, the second real-time input data from the second input device; and sending, from the replicate client device, the second real-time input data, through the server, to one or more additional replicate client devices connected to the server and the primary client device.

In at least one embodiment, for managing multi-user AR collaboration, the method further comprises: receiving, at the server, local user inputs from the replicate client device providing remote instructions; sending the local user inputs through the server to the primary client device; displaying remote video input on the replicate client device in combination with the model sets and the intervention plan, the model sets including an underlying surface model; executing, by the replicate client device, a pixel selection evaluator based at least in part on the local user inputs and the remote video input, thereby generating a first pixel selection output; executing, by the replicate client device, a model selection evaluator based at least in part on the model sets and the first pixel selection output to map a pixel location in a render window to a 3D location of the underlying surface model, thereby generating a first model selection output; rendering, on the replicate client device, first selected faces of the underlying surface model based at least in part on the first model selection output; and rendering, on the replicate client device, first traced pixels based at least in part on the first pixel selection output.

In at least one embodiment, for managing the multi-user AR collaboration at the primary client device performing the AR intervention, the method further comprises: processing remote user inputs on the primary client device; receiving local video input from the primary client device; executing, by the primary client device, a pixel selection evaluator based at least in part on the remote user inputs and the local video input, thereby generating a second pixel selection output; executing, by the primary client device, a model selection evaluator based at least in part on the model sets and the remote user inputs, thereby generating a second model selection output; rendering audio instructions based at least in part on the remote user inputs at the primary client device; rendering second selected faces based at least in part on the second pixel selection output at the primary client device; and rendering second traced pixels based at least in part on the second model selection output at the primary client device.

In at least one embodiment, to synchronize devices and tracks of the multi-user AR collaboration, the method further comprises: storing the first real-time input data in a first buffer in corresponding first device tracks of the primary client device; generating first clock ticks at the primary client device; processing the first real-time input data in the first buffer through a first filter chain from the first clock ticks; generating first data frames from the first filter chain; receiving, at the server, the first data frames from the primary client device having a first set of corresponding time stamps determined from the first clock ticks; storing the second real-time input data in a second buffer in corresponding second device tracks of the replicate client device; generating second clock ticks at the replicate client device; processing the second real-time input data in the second buffer through a second filter chain from the second clock ticks; generating second data frames from the second filter chain; receiving, at the server, the second data frames from the replicate client device having a second set of corresponding time stamps determined from the second clock ticks; generating, at the server, combined data frames based at least in part on the first data frames and the second data frames along with the first set of corresponding time stamps and the second set of corresponding time stamps; and storing the combined data frames in a database.

In at least one embodiment, the method further comprises: retrieving, by the server, the combined data frames from the database; generating, by the server, output clock ticks; extracting, by the server, a primary client data frame and a primary client time stamp from the combined data frames for the primary client device corresponding to a current output clock tick; extracting, by the server, a replicate client data frame and a replicate client time stamp from the combined data frames for the replicate client device corresponding to the current output clock tick; combining, by the server, extracted data frames of the primary client device and the replicate client device between server time stamps corresponding to current and previous output clock ticks; and broadcasting, by the server, the combined data frames along with corresponding time stamps to the primary client device and the replicate client device.

In at least one embodiment, for guiding geometric resection by AR visualization, the method further comprises: obtaining, by the server, a plurality of resection planes from the intervention plan; obtaining, by a client device, a plurality of active cut planes from a tracked instrument from one of the first real-time input data or the second real-time input data; determining, by the client device, the evaluation by comparing at least one of the plurality of active cut planes to at least one of the plurality of resection planes; calculating, by the client device, the metrics to determine at least one of angle offset and tip-to-plane distance; calculating, by the client device, the faces of the surface model that intersects with the plane of the tracked instrument; and producing, by the client device, the AR visualization by generating the trajectory of the tracked instrument, outlining an intersection of one of the plurality of active cut planes and the model set, and displaying a color-coded angle offset and a tip-to-plane distance to indicate precision, wherein the client device is the primary client device or the replicate client device.

In at least one embodiment, the for guiding needle placement by AR visualization, the method further comprises: obtaining, by the server, a plurality of line trajectories from the intervention plan, each of the line trajectories comprising an entrance point and a target point; obtaining, by a client device, a plurality of active instrument line placements from a tracked instrument from one of the first real-time input data or the second real-time input data; determining, by the client device, the evaluation by comparing at least one of the plurality of active instrument line placements to at least one of the plurality of line trajectories; calculating, by the client device, the metrics to determine at least one of tip-to-trajectory distance, tip-to-target distance, and instrument-to-trajectory angle; calculating, by the client device, the closest point between the tracked instrument tip and the planned trajectory; and producing, by the client device, the AR visualization by generating a trajectory of the tracked instrument, generating an intersection of a trajectory of the tracked instrument with the target point, generating a line between a tip of the tracked instrument and a planned line trajectory, and displaying a color-coded tip-to-trajectory distance, a tip-to-target distance, and an instrument-to-trajectory angle to indicate precision, wherein the client device is the primary client device or the replicate client device.

In at least one embodiment, for displaying critical structure avoidance by AR visualization, the method further comprises: obtaining, by the server, a first image of an intervention target and a critical structure image of the intervention target from the intervention plan; obtaining, by a client device, a plurality of tool placements from one of the first real-time input data or the second real-time input data from a tracked instrument; determining, by the client device, the evaluation by comparing at least one of the plurality of tool placements to a no-fly zone obtained from an overlay of the critical structure image on the first image; calculating, by the client device, the metrics to determine an incidence of the at least one of the plurality of tool placements with the no-fly zone; and displaying the AR visualization on the client device by showing in-field alerts indicating placement or trajectory of the tracked instrument intersecting with the no-fly zone, wherein the client device is the primary client device or the replicate client device.

In one broad aspect, in accordance with the teachings herein, there is provided a system for performing guiding augmented reality (AR) intervention for planning, intervention, guidance, and/or education for medical applications, wherein the system comprises: a server including: a database having: a plurality of data models that each have a plurality of model set records, a plurality of plans records, a plurality of recordings records, and a plurality of instruments records; a plurality of user records; and a plurality of session records; and at least one processor that is operatively coupled to the database and configured to execute program instructions for implementing: an HTTP server for providing endpoints for queries and delivery of content, user authentication, and management of sessions; and a WebSocket server to enable multi-client broadcast of data across device specific listening channels by setting up WebSocket clients; and a primary client device that is communicatively coupled to the server to interact with the HTTP server and the WebSocket server, the primary client device including a first processor and a first input device, the primary client device being configured to: receive model sets, an intervention plan having an intervention field, and session information about a session related to the AR intervention from the server; receive first real-time input data from the first input device; generate metrics by determining an evaluation of an execution of the intervention plan by comparing the intervention plan to the first real-time input data; display real-time graphics, based at least in part on the metrics, spatially over the intervention field; receive real-time status data, from the server, about a replicate client device connected to the server after the replicate client device joins the session; send the first real-time input data, through the server, to the replicate client device within the session; send the metrics and the evaluation computed from the intervention plan, through the server, to the replicate client device within the session; receive second real-time input data from the server, the second real-time input data originating from the replicate client device and relating to the intervention plan; and display real-time graphics based at least in part on the second real-time input data from the replicate client device.

In at least one embodiment, the system further comprises the replicate client device, the replicate client device having a second processor and a second input device, wherein for remotely observing the guided AR intervention the replicate client device is configured to: receive the model sets, the intervention plan, and the session information about the session related to the AR intervention from the server; receive the first real-time input data, the metrics, and the evaluation broadcasted from the primary client device; and display real-time graphics based at least in part on the model sets, the intervention plan, the first real-time input data, the metrics, and the evaluation.

In at least one embodiment, for providing remote mentoring of the guided AR intervention: the replicate client device is configured to: receive the second real-time input data from the second input device; and send the second real-time input data, through the server, to one or more additional replicate client devices connected to the server and the primary client device.

In at least one embodiment, for managing multi-user AR collaboration: the server is configured to receive local user inputs from the replicate client device providing remote instructions and send the local user inputs to the primary client device; and the replicate client device is configured to: display remote video input in combination with the model sets and the intervention plan, the model sets including an underlying surface model; execute a pixel selection evaluator based at least in part on the local user inputs and the remote video input, thereby generating a first pixel selection output; execute a model selection evaluator based at least in part on the model sets and the first pixel selection output to map a pixel location in a render window to a 3D location of the underlying surface model, thereby generating a first model selection output; render first selected faces of the underlying surface model based at least in part on the first model selection output; and render first traced pixels based at least in part on the first pixel selection output.

In at least one embodiment, for managing the multi-user AR collaboration at the primary client device performing the AR intervention, the primary client device is configured to: process remote user inputs; receive local video input; execute a pixel selection evaluator based at least in part on the remote user inputs and the local video input, thereby generating a second pixel selection output; execute a model selection evaluator based at least in part on the model sets and the remote user inputs, thereby generating a second model selection output; render audio instructions based at least in part on the remote user inputs; render second selected faces based at least in part on the second pixel selection output; and render second traced pixels based at least in part on the second model selection output.

In at least one embodiment, to synchronize devices and tracks of the multi-user AR collaboration: the primary client device is configured to: store the first real-time input data in a first buffer in corresponding first device tracks of the primary client device; generate first clock ticks; process the first real-time input data in the first buffer through a first filter chain from the first clock ticks; and generate first data frames from the first filter chain; the replicate client device is configured to: store the second real-time input data in a second buffer in corresponding second device tracks of the replicate client device; generate second clock ticks at the replicate client device; process the second real-time input data in the second buffer through a second filter chain from the second clock ticks; and generate second data frames from the second filter chain; and the server is configured to: receive, from the primary client device, the first data frames having a first set of corresponding time stamps determined from the first clock ticks; receive the second data frames from the replicate client device having a second set of corresponding time stamps determined from the second clock ticks; and generate combined data frames based at least in part on the first data frames and the second data frames along with the first set of corresponding time stamps and the second set of corresponding time stamps; and store the combined data frames in a database.

In at least one embodiment, the server is further configured to: retrieve the combined data frames from the database; generate output clock ticks; extract a primary client data frame and a primary client time stamp from the combined data frames for the primary client device corresponding to a current output clock tick; extract a replicate client data frame and a replicate client time stamp from the combined data frames for the replicate client device corresponding to the current output clock tick; combine extracted data frames of the primary client device and the replicate client device between server time stamps corresponding to current and previous output clock ticks; and broadcast the combined data frames along with corresponding time stamps to the primary client device and the replicate client device.

In at least one embodiment, for guiding geometric resection by AR visualization: the server is configured to obtain a plurality of resection planes from the intervention plan and send the plurality of resection planes to a client device; and the client device is configured to: obtain a plurality of active cut planes from a tracked instrument from one of the first real-time input data or the second real-time input data; determine the evaluation by comparing at least one of the plurality of active cut planes to at least one of the plurality of resection planes; calculate the metrics to determine at least one of angle offset and tip-to-plane distance; calculate the faces of the surface model that intersects with the plane of the tracked instrument; and produce the AR visualization by generating the trajectory of the tracked instrument, outlining an intersection of one of the plurality of active cut planes and the model set, and displaying a color-coded angle offset and a tip-to-plane distance to indicate precision, wherein the client device is the primary client device or the replicate client device.

In at least one embodiment, for guiding needle placement by AR visualization: the server is configured to obtain and send a plurality of line trajectories from the intervention plan to a client device, where each of the line trajectories comprise an entrance point and a target point; and the client device is configured to: obtain a plurality of active instrument line placements from a tracked instrument from one of the first real-time input data or the second real-time input data; determine the evaluation by comparing at least one of the plurality of active instrument line placements to at least one of the plurality of line trajectories; calculate the metrics to determine at least one of tip-to-trajectory distance, tip-to-target distance, and instrument-to-trajectory angle; calculate the closest point between the tracked instrument tip and the planned trajectory; and produce the AR visualization by generating a trajectory of the tracked instrument, generating an intersection of a trajectory of the tracked instrument with the target point, generating a line between a tip of the tracked instrument and a planned line trajectory, and displaying a color-coded tip-to-trajectory distance, a tip-to-target distance, and an instrument-to-trajectory angle to indicate precision, wherein the client device is the primary client device or the replicate client device.

In at least one embodiment, for displaying critical structure avoidance by AR visualization: the server is configured to obtain and send a first image of an intervention target and a critical structure image of the intervention target from the intervention plan to a client device; and the client device is configured to: obtain a plurality of tool placements from one of the first real-time input data or the second real-time input data from a tracked instrument; determine the evaluation by comparing at least one of the plurality of tool placements to a no-fly zone obtained from an overlay of the critical structure image on the first image; calculate the metrics to determine an incidence of the at least one of the plurality of tool placements with the no-fly zone; and display the AR visualization on the client device by showing in-field alerts indicating placement or trajectory of the tracked instrument intersecting with the no-fly zone, wherein the client device is the primary client device or the replicate client device.

In another broad aspect, in accordance with the teachings herein, there is provided a computer-implemented method of managing a multi-user augmented reality (AR) collaboration, the method comprising: receiving first model sets from a first client device; receiving local user inputs from the first client device; processing remote video input onto the first client device; executing a model selection evaluator based on the first model sets and the local user inputs; executing a pixel selection evaluator based on the local user inputs and the remote video input; rendering selected faces based on the output from the model selection evaluator; rendering traced pixels based on the output from the pixel selection evaluator; receiving second model sets from a second client device; processing remote user inputs onto the second client device; receiving local video input from the second client device; executing a model selection evaluator based on the second model sets and the remote user inputs; executing a pixel selection evaluator based on the remote user inputs and the local video input; rendering audio instructions based on the remote user inputs; rendering selected faces based on the output from the pixel selection based on the pixel selection evaluator; rendering traced pixels based on the output from the model selection evaluator; and managing socket broadcasts of at least one of the local user inputs, the remote video input, the remote user inputs, and the local video input.

In another broad aspect, in accordance with the teachings herein, there is provided a computer-implemented method of inside-out tracking using a client device having a processor, the method comprising: receiving tool image data of a tool at the processor from a first camera; determining tool coordinates from the tool image data using the processor; mapping the tool coordinates to device coordinates using the processor; mapping the device coordinates to client device coordinates using the processor; mapping the client device coordinates to reference coordinates using the processor; generating a virtual-space image of the tool by applying a registration transform to the reference coordinates using the processor; and displaying the virtual-space image of the tool on a display.

In another broad aspect, in accordance with the teachings herein, there is provided a computer-implemented method of controlling devices and tracks, the method comprising: generating clock ticks; receiving a first plurality of input data from a first device into a buffer; having a first set of corresponding time stamps determined from the clock ticks; processing the buffer data on the clock ticks to generate the first plurality of data frames along with the first set of corresponding time stamps; receiving a second plurality of input data from a second device into a buffer; having a second set of corresponding time stamps determined from the clock ticks; processing the buffer data on the clock ticks to generate the second plurality of data frames along with the second set of corresponding time stamps; sending each of the plurality of data frames and time stamps to the server; and outputting each of the plurality of data frames to an AR application.

In another broad aspect, in accordance with the teachings herein, there is provided a computer-implemented method for performing AR-assisted scientific output augmentation at a client device having a processor, the method comprising: receiving a surface representation of a Cone Beam Computed Tomography (CBCT) model and a corresponding figure from a journal article at the client device; anchoring the CBCT model to the figure image using the processor; calculating a pose using the processor by matching known spatial points of the figure image to image points of the CBCT model via homography; and displaying the pose on a display.

In another broad aspect, in accordance with the teachings herein, there is provided a computer-implemented method for performing AR-assisted surgical procedure walkthrough at a client device having a processor, the method comprising: receiving a virtual surgical plan at the client device; receiving a virtual model at the client device; embedding the virtual model to a physical object using the processor; receiving tool manipulation data from user input at the client device; modifying a view of the virtual model in relation to the physical object using the processor based on the tool manipulation data; determining metrics by using the processor to apply spatial registration and track the tool used in execution of the virtual surgical plan; and providing feedback at the client device based on the metrics.

In another broad aspect, in accordance with the teachings herein, there is provided a computer-implemented method for performing outside-in tracking at a client device having a processor, the method comprising: receiving device image data at the processor from a first camera; determining device coordinates from the device image data using the processor; mapping the device coordinates to device sensor coordinates using the processor; mapping the device sensor coordinates to device-tracker coordinates using the processor; mapping the device-tracker coordinates to device-reference coordinates using the processor; applying a first registration transform to the device-reference coordinates using the processor to display the device in virtual space; receiving tool image data at the processor from a second camera; determining tool coordinates from the tool image data using the processor; mapping the tool coordinates to tool sensor coordinates using the processor; mapping the tool sensor coordinates to tool-tracker coordinates using the processor; mapping the tool-tracker coordinates to tool-reference coordinates using the processor; generating a virtual-space image of the tool by applying a second registration transform to the tool-reference coordinates using the processor; and displaying the virtual-space image of the tool on a display.

In another broad aspect, in accordance with the teachings herein, there is provided a device for performing an AR method related to at least one of planning, intervention, guidance, and education for medical applications, wherein the device comprises: a display for displaying AR images; a user interface for receiving user input at the device; a memory for storing program instructions for performing the AR method; and a processor that is operatively coupled to the display, the user interface and the memory, wherein the processor is configured to execute the program instructions for performing a method according to any one of the methods described in accordance with the teachings herein.

In another broad aspect, in accordance with the teachings herein, there is provided a system for performing allowing at least one client device for perform an AR method related to at least one of planning, intervention, guidance, and education for medical applications, wherein the system comprises: a server including: a database having: a plurality of data models that each have a plurality of model set records, a plurality of plans records, a plurality of recordings records and a plurality of instruments records; a plurality of user records; and a plurality of session records; and at least one processor that is operatively coupled to the database and configured to execute program instructions for implementing: an HTTP server for providing endpoints for queries and delivery of content, user authentication, and management of sessions; and a WebSocket server to enable multi-client broadcast of data across device specific listening channels by setting up WebSocket clients; and at least one client device that is communicatively coupled to the server to interact with the HTTP server and the WebSocket server, the at least one client device being defined according to the any of the teachings herein and being configured to perform any one of the methods described in accordance with the teachings herein.

Other features and advantages of the present application will become apparent from the following detailed description taken together with the accompanying drawings. It should be understood, however, that the detailed description and the specific examples, while indicating preferred embodiments of the application, are given by way of illustration only, since various changes and modifications within the spirit and scope of the application will become apparent to those skilled in the art from this detailed description.

BRIEF DESCRIPTION OF THE DRAWINGS

For a better understanding of the various embodiments described herein, and to show more clearly how these various embodiments may be carried into effect, reference will be made, by way of example, to the accompanying drawings which show at least one example embodiment, and which are now described. The drawings are not intended to limit the scope of the teachings described herein.

FIG. 41 shows a flow chart of an example embodiment of a method of text to speech conversion in the AR system of FIG. 1A.

FIG. 42 shows a flow chart of an example embodiment of a method of speech to text conversion in the AR system of FIG. 1A.

FIG. 46 shows a flow chart of an example embodiment of a method of guiding AR intervention in the AR system of FIG. 1A.

FIG. 47 shows a flow chart of an example embodiment of a method for remotely observing a guided AR intervention in the AR system of FIG. 1A.

Figure 1A:
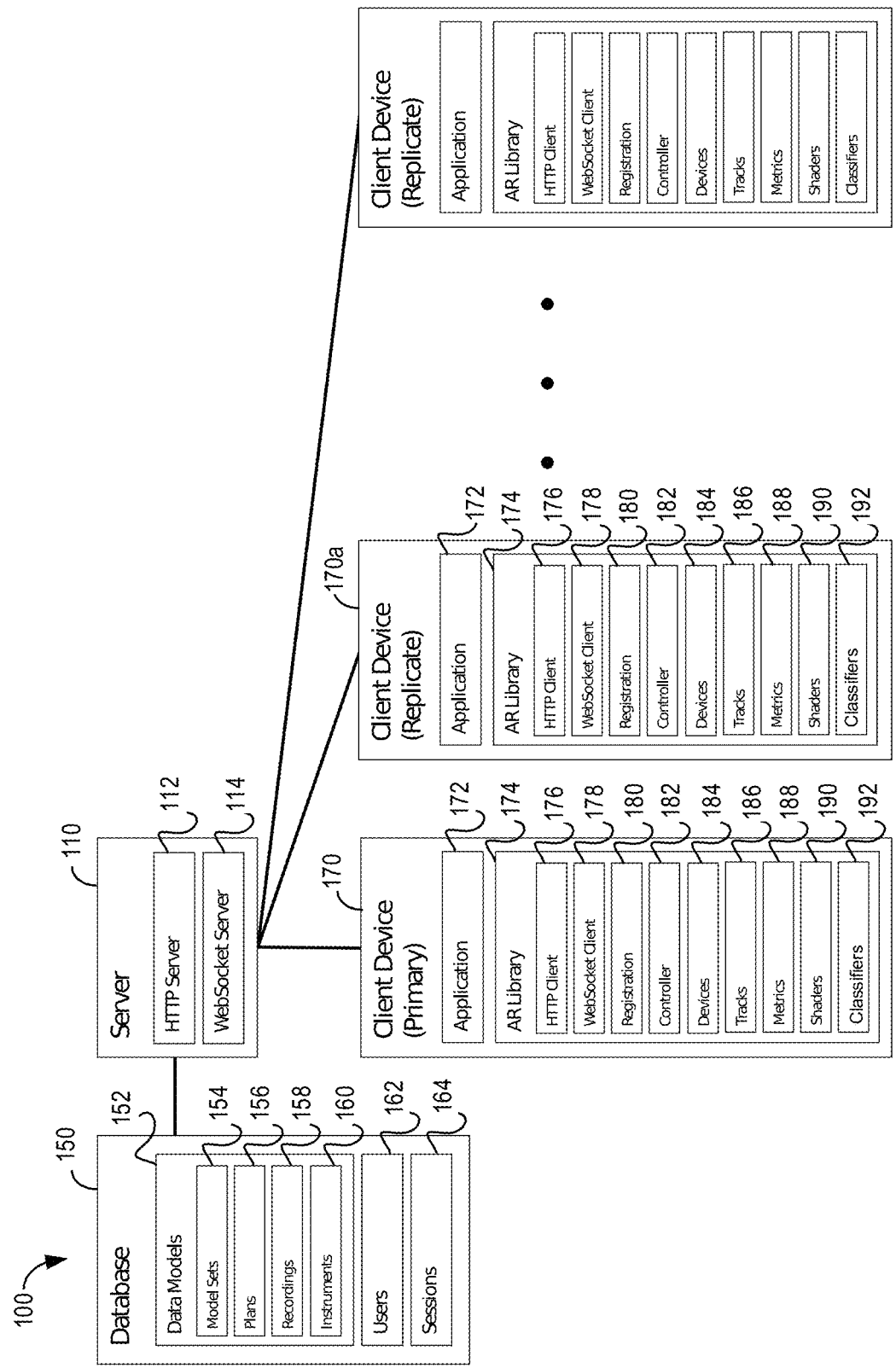
FIG. 1A illustrates an example embodiment of an augmented reality (AR) system for multi-client broadcasting and streaming in accordance with the teachings herein.

Further aspects and features of the example embodiments described herein will appear from the following description taken together with the accompanying drawings.

DETAILED DESCRIPTION OF THE EMBODIMENTS

Various embodiments in accordance with the teachings herein will be described below to provide an example of at least one embodiment of the claimed subject matter. No embodiment described herein limits any claimed subject matter. The claimed subject matter is not limited to devices, systems, or methods having all of the features of any one of the devices, systems, or methods described below or to features common to multiple or all of the devices, systems, or methods described herein. It is possible that there may be a device, system, or method described herein that is not an embodiment of any claimed subject matter. Any subject matter that is described herein that is not claimed in this document may be the subject matter of another protective instrument, for example, a continuing patent application, and the applicants, inventors or owners do not intend to abandon, disclaim, or dedicate to the public any such subject matter by its disclosure in this document.

It will be appreciated that for simplicity and clarity of illustration, where considered appropriate, reference numerals may be repeated among the figures to indicate corresponding or analogous elements. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures, and components have not been described in detail so as not to obscure the embodiments described herein. Also, the description is not to be considered as limiting the scope of the embodiments described herein.

It should also be noted that the terms "coupled" or "coupling" as used herein can have several different meanings depending on the context in which these terms are used. For example, the terms coupled or coupling can have a mechanical or electrical connotation. For example, as used herein, the terms coupled or coupling can indicate that two elements or devices can be directly connected to one another or connected to one another through one or more intermediate elements or devices via an electrical signal, electrical connection, or a mechanical element depending on the particular context.

It should also be noted that, as used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

It should be noted that terms of degree such as "substantially", "about", and "approximately" as used herein mean a reasonable amount of deviation of the modified term such that the end result is not significantly changed. These terms of degree may also be construed as including a deviation of the modified term, such as by 1%, 2%, 5%, or 10%, for example, if this deviation does not negate the meaning of the term it modifies.

Furthermore, the recitation of numerical ranges by endpoints herein includes all numbers and fractions subsumed within that range (e.g., 1 to 5 includes 1, 1.5, 2, 2.75, 3, 3.90, 4, and 5). It is also to be understood that all numbers and fractions thereof are presumed to be modified by the term "about" which means a variation of up to a certain amount of the number to which reference is being made if the end result is not significantly changed, such as 1%, 2%, 5%, or 10%, for example.

The example embodiments of the devices, systems, or methods described in accordance with the teachings herein may be implemented as a combination of hardware and software. For example, at least some embodiments or a portion of the embodiments described herein may be implemented, at least in part, by using one or more computer programs, executing on one or more programmable devices comprising at least one processing element and at least one storage element (i.e., at least one volatile memory element and at least one non-volatile memory element). The hardware may comprise input devices including at least one of a touch screen, a keyboard, a mouse, buttons, keys, sliders, and the like, as well as one or more of a display, a printer, and the like depending on the implementation of the hardware.

It should also be noted that there may be some elements that are used to implement at least part of the embodiments described herein that may be implemented via software that is written in a high-level procedural language such as object-oriented programming. The program code may be written in C++, C#, Python, JavaScript, or any other suitable programming language and may comprise modules or classes, as is known to those skilled in object-oriented programming. Alternatively, or in addition thereto, some of these elements implemented via software may be written in assembly language, machine language, or firmware as needed. In either case, the language may be a compiled or interpreted language.

At least some of these software programs may be stored on a computer-readable medium such as, but not limited to, ROM, a magnetic disk, an optical disc, a USB key, and the like that is readable by a device having at least one processor, an operating system, and the associated hardware and software that is necessary to implement the functionality of at least one of the embodiments described herein. The software program code, when read by the device, configures the device to operate in a new, specific, and predefined manner (e.g., as a specific-purpose computer) in order to perform at least one of the methods described herein.

At least some of the programs associated with the devices, systems, and methods of the embodiments described herein may be capable of being distributed in a computer program product comprising a computer-readable medium that bears computer-usable instructions, such as program code, for one or more processing units. The medium may be provided in various forms, including non-transitory forms such as, but not limited to, one or more diskettes, compact disks, tapes, chips, and magnetic and electronic storage. In alternative embodiments, the medium may be transitory in nature such as, but not limited to, wire-line transmissions, satellite transmissions, internet transmissions (e.g., downloads), media, digital and analog signals, and the like. The computer-usable instructions may also be in various formats, including compiled and non-compiled code.

In accordance with the teachings herein, there are provided various example embodiments for systems and methods for multi-client deployment of augmented reality (AR) instrument tracking which may be used in the context of at least one of surgical planning, intervention, guidance, and education. The example embodiments are not necessarily limited to multi-client deployment of AR, but may also be applicable to mixed reality (MR), virtual reality (VR), augmented virtuality (AV), and similar modes of technology.

For example, in at least one embodiment, an AR system is provided that utilizes multi-client broadcasting and streaming to allow real-time guided AR intervention (e.g., surgery) using metrics. The system (or a client device that is part of the AR system) receives or loads an intervention (e.g., surgical) plan and session information related to the AR intervention (e.g., surgery). The session information may include access credentials, a session identifier, and a port, which can be obtained from a server in the AR system. The server can facilitate communication between multiple client devices. The system (or client device) receives real-time data (e.g., position and orientation) of a tool (e.g., an osteotome) from an input device, such as an AR headset (also known as "AR glasses") or a mobile device (e.g., a tablet device). The server can permit at least one other client device to join the session. The system (or client device) can receive real-time data, from the server, of the at least one other client device joined in the session. The system (or client device) can send real-time data to the server to be broadcast to any (or all) of the client devices joined in the session. The system (or client device) modifies the real-time data by applying volume operations (e.g., dilation and erosion) or mesh operations (e.g., space portioning) based on the intervention plan and/or the session information. The system (or client device) modifies the real-time data further by determining intersections. The system (or client device) generates metrics by determining an evaluation (i.e., scoring) of an execution of the intervention (e.g., surgical) plan by comparing the initial intervention (e.g., surgical) plan to user execution. The system (or client device) can display real-time graphics (e.g., shaders) based on the evaluation.

In an implementation of the at least one embodiment of the AR system described above, the real-time guided AR intervention (e.g., surgery) uses metrics to guide geometric resection. In particular, the intervention plan comprises a plurality of resection planes; the real-time data comprises a plurality of active cut planes; the evaluation is determined by comparing at least one of the plurality of active cut planes to at least one of the plurality of resection planes; and the metrics comprise at least one of angle offset and tip-to-plane distance.

In another implementation of the at least one embodiment of the AR system described above, the real-time guided AR intervention (e.g., surgery) uses metrics to guide needle placement. In particular, the intervention plan comprises a plurality of line trajectories, each of the line trajectories comprising an entrance point and a target point; the real-time data comprises a plurality of active needle placements; the evaluation is determined by comparing at least one of the plurality of active needle placements to at least one of the plurality of line trajectories; and the metrics comprise at least one of tip-to-trajectory distance, tip-to-target distance, and needle-to-trajectory angle.

In yet another implementation of the at least one embodiment of the AR system described above, the real-time guided AR intervention (e.g., surgery) uses metrics to guide critical structure avoidance. In particular, the intervention plan comprises a first image of an intervention target and a critical structure image of the intervention target; the real-time data comprises a plurality of tool placements; the evaluation is determined by comparing at least one of the plurality of tool placements to a no-fly zone obtained from an overlay of the critical structure image on the first image; and the metrics comprise the incidence of the at least one of the plurality of tool placements with the no-fly zone.

In at least one embodiment, the system provides a 3D comparison of a user's actual movements to a stored "surgical plan". If a user makes the exact same movements, for example, as the pre-defined surgical plan, the system may provide the user with a very high score. The shaders are displayed as computer graphics that describe how a surface behaves, which may reflect how the system renders data or content in real time. For example, the shader can be used to show performance metrics, graphically represented by a different color or overlays. The shaders can be, for example, opaque, semi-transparent, or outlines. The shaders may also be used so that the meshes can be seen in ways that enhance the AR experience. For example, the shaders can be used to indicate how well a user performed compared to the pre-defined surgical plan. It will be appreciated that any reference to a "surgical plan" in this disclosure applies equally to an "intervention plan", and vice versa.

In another aspect, a technical problem is providing a similar experience to different users across different devices and different platforms in different locations (e.g., mobile, browser, headset), where there may also be vendor differences (e.g., Apple, Android, Windows). Current mobile devices have more computing power than headsets, yet mobile devices require rendering for a single display as opposed to headsets, which uses dual renderings (as needed for each eye). At least one of the embodiments described in accordance with the teachings herein provides a technical solution to this problem by creating models at different levels of detail and optimizing settings to accommodate for the different levels of computing power of different devices that are operating on the same source data (e.g., refresh rate, clipping planes, and polygon count).

In another aspect, another technical problem is providing device-specific implementations in a development environment that consists of cross-platform engines and libraries (e.g., Unity and Vuforia). For example, outline shaders (that apply a simple outline around an object) do not display correctly on headsets, but they do on mobile devices. At least one of the embodiments described in accordance with the teachings herein provides a technical solution to this problem by having different shader implementations on headsets to display cutting planes in a surgical plan.

In another aspect, another technical problem is that the same-voice recognition implementation works on Android and Microsoft devices, but not with iOS devices, or that same-voice recognition is in varying degrees of implementation with Microsoft devices being the most developed. At least one of the embodiments described in accordance with the teachings herein provides a technical solution by having a separate iOS implementation.

In another aspect, another technical problem is the different level of support for common libraries and frameworks across devices, such as .NET versions, where a headset supports legacy versions at major releases behind mobile devices, resulting in access to a reduced feature set. At least one of the embodiments described in accordance with the teachings herein provides a technical solution by having a different implementation of functions, such as WebSockets.

In another aspect, another technical problem is the difficulty of coordinating device/platform specific rendering. For example, remote browsers have a virtual experience as they do not view physical models in the local space, and different shaders are needed on different devices. At least one of the example embodiments described in accordance with the teachings herein provides a technical solution by having different display options based on context, when no physical model is present, to visualize the base anatomical model as well, and by using wireframes on virtual models, which provide a better display of surgical plans.

In another aspect, another technical problem is the difficulty of reconciling different coordinate system types with different rendering engines. For example, Unity™ uses left-handed coordinate systems, while other rendering engines use right-handed coordinate systems. At least one of the embodiments described in accordance with the teachings herein provides a technical solution by mapping coordinate systems back and forth across different rendering engines. For example, where a rendering engine uses a left-handed coordinate system, the positive x, y, and z axes point right, up, and forward, respectively, and positive rotation is clockwise about the axis of rotation. Where a rendering engine uses a right-handed coordinate system, the positive x and y axes point right and up, and the negative z axis points forward, and positive rotation is counter-clockwise about the axis of rotation. Such a formal convention defines a 3D coordinate system (X/Y/Z). Where the convention used by various rendering engines is known, the coordinate mappings are accomplished by creating inversion matrices which swap an axis to display correctly on the "new" coordinate system.

In another aspect, another technical problem is the difficulty of broadcasting and streaming device data so that multiple local and remote clients can visualize content in a synchronized way. At least one of the embodiments described in accordance with the teachings herein provides a technical solution by having data broadcasted to and shared across clients through WebSockets, which is a common standard with implementations across different languages and frameworks. At least one of the embodiments described in accordance with the teachings herein provides another technical solution by using time-stamped buffers at the device level to help synchronize data from remote clients in local applications. The data is synchronized such that the data displays at the same time and speed across various devices. For example, all the devices display an image at the receive time derived from the same data set, but possibly at different points of view, zoom levels, or perspectives (despite differences for optimization of images).

In another aspect, another technical problem is the difficulty of co-registration of multiple devices and coordinate systems. At least one of the embodiments described in accordance with the teachings herein provides a technical solution by (a) using reference coordinate frames that are specific to each device/sensor; (b) collecting data of a reference object present in each individual reference frame;

and (c) utilizing measurement correspondences that enable co-registration of coordinate frames.

In another aspect, another technical problem is the difficulty of real-world deployment to institutions that have organizational firewalls, along with the associated security and privacy issues. At least one of the embodiments described in accordance with the teachings herein provides a technical solution by ensuring that, at the system level, security and privacy are used at the data store, encryption is used in storage and transit of data, anonymization of data is used, and distribution of data during a session is not permanently stored but only exists in RAM for the duration of the session. At least one of the embodiments described in accordance with the teachings herein provides another technical solution by providing an AR system that complies with different institutions' security and privacy policies and uses VPN tunnels, while simultaneously allowing technical staff at each institution control over privacy and security settings of the system.

Reference is first made to FIG. 1A, showing an example embodiment of an augmented reality (AR) system 100 for multi-client broadcasting and streaming. The system 100 provides a framework for AR applications with data streaming and synchronization that can be deployed across multiple devices locally and remotely. The system 100 includes a server 110 and a database 150 where the server 110 can communicate with one or more client devices 170. The server 110 may include one or more computers that operate as an HTTP server 112 and a WebSocket server 114. Client devices 170 may be, for example, mobile devices (e.g., tablets, phones), desktops, laptops, headsets, or projector systems. The client devices 170 may have a processor (which can refer to a single processor, or collectively to a dual processor or multiple processors). The application 172 is a software program that may be deployed natively or through web standards conforming browsers supporting technologies such as WebGL and WebXR. The application 172 is used to allow a user to operate one or more of the AR methods described herein on their client device. The application 172 may have a user interface (UI) for operation of these AR methods. The client devices 170 may operate software or otherwise communicate with the server 110 such that the client devices 170 can be logically divided into a primary client device 170 and one or more replicate client devices 170a (only one of which is labelled in FIG. 1A for ease of illustration). For simplicity, reference to client device 170 applies equally to replicate client device 170a unless specifically referred to as the primary device, and vice versa.

An AR library 174 and the database 150 can be agnostic to the engine and rendering architecture of the applications 172 across client devices 170 due to conformance to device application programming interfaces (APIs), platform software development kits (SDKs), data, and technology standards. For example, one client device 170 may deploy the application 172 on a tablet via Unity, a popular game engine, whereas another client device 170 may be an iPhone that runs an application built via Apple's native toolchain and ARKit.

The database 150 includes references and relations for: (a) data models 152 used in AR applications, (b) user profiles 162 (shown as "Users 162") for access control and authentication of the users of the client devices 170, and (c) sessions 164 for synchronization of AR applications that are used across multiple devices and locations.

In this example embodiment, the data models 152 used in the AR system 100 include model sets records 154, plans records 156, recordings records 158, and instruments records 160.

The model sets records 154 can be more generalized data models and include static surface and volume representations derived across different imaging modalities such as, but not limited to, at least one of computed tomography (CT), medical resonance (MR), positron emission tomography (PET), and ultrasound (US), for example. These can span across multiple stages of imaging and intervention such as, but not limited to, at least one of preoperative, intraoperative, postoperative, and ex-vivo, for example. The static surface and volume representations can represent different physiological data such as, but not limited to, at least one of the normal anatomy and contours of structure and disease, for example.

Alternatively, or in addition, the static surface and volume representations can represent: surface anatomy of the skin; contours of normal bony anatomy and abnormal or morphological differences; disruptions or irregularities in bony anatomy (e.g., fractures of the bone, and tumors of the bone); surface and internal anatomy of soft tissue (e.g., blood vessels, muscles, and nerves) in the normal and abnormal/diseased state; regions of interest; and critical structures to be avoided. Surface and volume representations can also include non-human or animal data, tools, and/or physical features of the environment (e.g., operating room table, operating room lights, fiducial markers, and operating microscope). When displaying critical structure avoidance by AR visualization, the intervention plan may include an intervention target and a critical structure surface or volume in proximity of the intervention target.

The plans records 156 include parametric information and geometric representations regarding how a procedure is to be executed in reference to data from the model sets records 154 such as contours of structure and disease. Examples of parametric information for a procedure include: lines defined by a point; direction vectors from an entry and target point; planes defined by a point and a normal as fitted to a set of entry and target points. Geometric representations can be used for rendering, such as four vertices and a quad that makes up the plane.

The recordings records 158 include dynamic information recorded through connected devices such as, but not limited to, at least one of navigation data of tracked tools, gesture information of users using a tracked tool, annotations (e.g., audio, text), video, and sensor streams, for example.

The data models 152 used for AR applications may adhere to FAIR data principles (see, e.g., https://www.nature.com/articles/sdata201618): Findable, Accessible, Interoperable, Reusable. Alternatively, or in addition, the data models 152 may be configured to adhere to other data principles or standards. The FAIR data principles are described as follows:

Findable: data is assigned a globally unique and persistent identifier (ID) and is described using rich metadata;

Accessible: data is retrievable by the ID via standard communication protocols with appropriate authentication and authorization, and metadata can be retrieved independently of underlying data;

Interoperable: metadata is represented in standard data-interchange format, data assets (e.g., any other data) are stored in standard formats, and metadata references other metadata or data as appropriate; and Reusable: metadata specifies a data usage license, metadata adheres to community standards, and metadata describes data assets through accurate and relevant attributes.

The data models 152 may adhere to FAIR guidelines through the following implementations:

Findability: a Universally Unique IDentifier (UUID4) is generated and assigned to each data model 152, and each data model 152 is paired with a detailed metadata;

Accessibility: REST API endpoints provide JavaScript Object Notation (JSON) responses that are human and machine-readable, metadata is retrieved independently of data model assets, and only authorized users may access data model assets (authentication is done via OAuth2 protocol);

Interoperability: API replies are in JSON, which is a data-interchange format consumable by most languages and platforms, and data model assets are stored in industry standard formats (e.g., DICOM/Nifti for volume representations, and OBJ for mesh representations); and Reusability: metadata contains tag attributes that provide a context for the data and can be queried against, metadata specifies a license and conditions for data use, and metadata specifies references and sources where data was used.

Advantageously, in at least one embodiment, the server 110 and the database 150 of the system 100 can be used to manage the AR data and various user sessions by using metadata that adheres to FAIR data principles.

The metadata JSON for a data model 152 may contain a number of fields such as, but not limited to:

ID: a universally unique identifier for the data model 152;

Description: a detailed description of the underlying data and procedures;

Date: the date that the data model 152 was created;

Correspondence contact: a contact person for inquiries regarding data;

Nodes: a parent/child relationship between representations, coordinate systems, and their transforms;

License: authorization and use permission information;

References: external references, including supporting publications, institutional research protocol number, and where data has been used;

ModelSets: resource paths (e.g., where the data is stored on a server, cloud, or folder structure) for volume and surface representations with corresponding SHA-2 and SHA-3 hashes;

Plan: a resource path for a plans record 156;

Instruments: resource paths with corresponding SHA-2 and SHA-3 hashes for surface representations of instruments records 160 used with the data model 152; and Recording: a resource path of recordings records 158.

In some embodiments, some of these fields may not be used and/or additional fields may be used.

The fields may also include: Tags: which are query fields that include five subfields: (1) Site: anatomical site, (2) Pathology/Injury: types of pathology and injuries present; (3) Intervention: type of procedure; (4) Modalities: underlying modalities included in the model sets record 154, and (5) Recordings: a list of recordings records 158. The fields may be used when, for example, the server 110 or a client device 170 uses a query to find procedures.

In a particular implementation, real-time data is broadcasted through WebSocket as JSON objects with associated metadata in the header field. The JSON object contains:

Name: a data event name for the data model 152;

Header: a metadata array descriptive of the message field for the data model 152; and Message: a data array corresponding to the event for the data model 152.

Tool data, user commands, metrics, and evaluations are broadcasted as a JSON object with a metadata header from a client device 170.

As an example, osteotomies and needle guidance may have the following encapsulation:

```
{
  "name": "eval",
  "header": [
    "distancevalidity",
    "pitchvalidity",
    "rollvalidity",
    "distance",
    "pitch",
    "roll"
  ],
  "message": [1, 1, 1, 1.11, 3.57, 4.91]
}
{
  "name": "eval",
  "header": [
    "distancevalidity",
    "distanceToLineValidity",
    "angleValidity",
    "distance",
    "distanceToLine",
    "angle"
  ],
  "message": [1, 1, 1, 2.10, 2.23, 9.71]
}
```

Client devices 170 may also utilize message queues for inter-process communication between connected hardware devices and data sharing between APIs such as with navigation hardware, microphone, or gesture interfaces.

Advantageously, in at least one embodiment, the data models 152 can be used to provide visual feedback. The data models 152 include data related to anatomy, pathology, instruments, and surgical plans generated post patient image acquisition. Typical patient image acquisitions include volume images (e.g., a series of DICOM files)—surgical planning data, segmentations, surface models, and instrument representations used in AR are not stored in a standardized way (because most patient images are interchanged with a picture archiving and communication system (PACS) server, which only manages DICOM files). Surgical planning data may be parametrically defined, which includes at least one of entry and target points, line definitions, and segmentations (e.g., manual, semi-automatic, or automatic from contouring over patient images), which can lead to segmented surface models that are representations of the anatomy and an underlying pathology. Instrument representations may be generated through 3D modelling or CAD, or may be reversed-engineered through 3D modelling and CAD from a reference surface scan. The data models 152 used in AR can also be used to provide visual feedback where the spatial and temporal context is better conveyed by the alignment of the visual feedback to physical space. Furthermore, tracked instruments provide real-time qualitative (visual) and quantitative feedback (metrics) with respect to the surgical plan.

The model sets records 154 may include representations for surface or volume rendering that are directly derived from imaging and segmentation across various stages. The volume representations may be stored in traditional medical image formats such as Nifti and anonymized DICOM, where headers encapsulate spatial information in origin, orientation, spacing, and extent of the data volume, as well as the voxel scalar data type. In addition to volumes that are directly derived from imaging modalities, volumes may also come from planning, such as prescribed radiation dose volumes in radiation therapy or contours or point annotations of various anatomical structures and disease. Volume representations can be visualized via direct volume rendering on the application 172 by using various visualization techniques such as ray-casting and texture-based methods. Two-dimensional (2D) slices can be specified according to indices across the imaging axes or via a point and normal to interpolate scalar values on an oblique imaging plane.

In at least one embodiment, the 2D slices are specified using a DICOM series. The DICOM series may contain origin, spacing, and direction meta information in the DICOM tags. For each DICOM file in the series, there may also be a slice location index in the DICOM tag indication where the slice is along the axis of the series. DICOM files belonging to the same series can be stacked to form a 3D matrix of scalar values (voxels). Once stacked in a volume, slices in the other two axes may be retrieved by fixing a location in the axis of interest and retrieving the 2D submatrix. Furthermore, once the 3D matrix of a voxel is formed, oblique planes (i.e., planes that are not in alignment with the axes of the volume) can be defined, the intersecting voxels of an oblique plane can be determined, and scalar values can be interpolated.

Surface models can be created from volumetric imaging through application of marching cubes to generate polygonal meshes. Masking can be applied on the volume prior to applying marching cubes to specify regions of interest (ROI) and better delineate structure. The marching cubes can also be used on contour volumes to generate their surface representations. The polygonal meshes can result from these operations by application of marching cubes. The polygonal meshes may also be constructed via physical tools such as digitizer pens tracing out anatomy (e.g., across phantoms, cadavers, patients) or digital tools to edit meshes and define regions and patterns. The surface models can be stored in standardized file formats such as OBJ geometry definitions (e.g., stored as .OBJ files).

Face normals can be calculated by application of the cross product on face edges. Winding order consistency (e.g., ordering of vertices for edges) can be checked by propagating through neighboring faces and comparing ordering of vertices in shared edges. Winding order consistency ensures that surface normals are oriented in the same direction. Vertex normals can be calculated by summing the normals of faces that share the same vertex. Consistent normal orientation can ensure proper rendering of the surface representation and ease of correction (e.g., reversing normals across the whole model). Face normals and vertex normals can be used in the surface models for rendering, where lighting models depend on the normal of a face/vertex and the camera direction, and the angle between a surface and a light source affects illumination at the face/vertex. More specifically, face normals may be important for rendering meshes. For example, face normals facing outwards show the material (e.g., color, light reflective properties, transparency) facing outwards towards the user. Face normals facing inwards, however, put a material on the inside of the object, which causes the object to look strange and not realistic to the user.

The plans records 156 can be stored as JSONs where fields specify parameters for the planning geometry. Types of plans records 156 include sets of line trajectories for needle procedures and sets of cutting planes for geometric resection. The plans records 156 can be generated through diagnostic viewing and planning software in reference to patient imaging. Line trajectories may be determined by an entry point and a target point. The cutting plane may be defined by a set of entry/target points, then the plane may be fitted to a set of points.

The recordings records 158 can be stored as JSON files, with recorded device data stored in an array according to their device channel field (e.g., from which device the data originated). Data streams that are recorded can be synchronized, where each measurement corresponds to a clock tick of a controller that is used by the client devices 170. An automation track can be created that corresponds to events, interactions, and parameter changes captured during a recording in a recordings record 158.

The instruments records 160 include surface representations of various clinical tools and instruments such as, but not limited to, probes, interventional tools, surgical tools, and biopsy tools, for example. The tools may include tweezers, forceps, scissors, bone instruments, surgical and vascular clips and clamps, scalpels, retractors, wound closure systems, and vascular access instruments. Different surface scanners (e.g., depth cameras or lasers) can be used to scan these objects (i.e., tools and instruments) and create a point cloud that represents the surface of the object. These point clouds can then be converted into a mesh.

The user profiles 162 can contain account, authentication, and access data that is used for auditing users of the system 100.

The sessions 164 can be allocated dynamically to host real-time bi-directional communication between the server 110 and multiple connected client devices 170 via WebSockets. A user having a user profile 162 may create a session 164 with a password and distribute to other users with their respective user profiles 162 for login.

As previously mentioned, the server 110 may include one or more computers that operate as the HTTP server 112 and the WebSocket server 114. The server 110 may be, for example, a physical server, a virtual server, or a shared server. The HTTP server 112 and the WebSocket server 114 may be implemented, for example, as their own separate physical servers or modules on the server 110.

The HTTP server 112 can expose the API endpoints, which may include requests for data models 152 (e.g., model sets records 154, plans records 156, recordings records 158), user profiles 162, and sessions 164. For example, the data model endpoints can allow HTTP methods, including the GET (e.g., GET datamodels), PUT (e.g., PUT datamodel), and POST (e.g., POST datamodel) operations. The GET datamodels operation can be used to retrieve a complete list of authorized data models 152 from the database 150. The GET datamodels operation can specify tags including site, intervention, modality, recording, and/or pathology/injury for queries for data models 152 that match specified tag fields. The GET datamodels operation can also specify an ID to get metadata for a specified data model 152 corresponding to the ID where the metadata includes data asset paths and hash values. The PUT datamodel operation can specify an ID and a supplied recording in order to update a specific data model 152 with the supplied recordings record 158. The POST datamodel operation can be used to upload a new data model archive including all assets with accompanying metadata.

The user endpoints can be used to authenticate users based on credentials, in order to enable the querying and retrieval of authorized content. For example, the user endpoints can utilize the POST operations: (1) POST user to create a new user profile 162 with a supplied name and password, and (2) POST login user to authenticate a user based on credentials. The user endpoints can also utilize GET operations to retrieve a list of users according to supplied query parameters such as by name, organization, and session. The PUT operations allow updates of user information and settings. The DELETE operation allows the deletion of users.

The session endpoints can be used to help manage Web-Socket communication across multiple connected client devices 170. The session endpoints can utilize the POST operations: (1) POST session to create a session 164 with a supplied name and password, and (2) POST login session to authenticate a user based on credentials and session access. The GET operation allows retrieval of available sessions by a user's session history, session the user is invited to, and access credentials. The PUT operation allows updates of a session such as user invite lists, referenced data models, settings, etc. The DELETE operation allows the deletion of a session.

The WebSocket server 114 can manage real-time broadcast and streaming of dynamic information across client devices 170 in the same session. For example, the WebSocket server 114 can synchronize device data streams across the same broadcast and listening channel ID within a session 164. The WebSocket server 114 can host multiple sessions 164 which client devices 170 may connect to. Each session 164 can represent a shared AR experience where the underlying data models 152 are shared by various users across the connected client devices 170.

The client devices 170 can come in many different forms and technologies. The client devices 170 can host the AR library 174 and application 172 (native or web). The client devices 170 may stream data from locally connected devices and hardware or via the WebSocket channels from a broadcasting client in the same session 164. The primary client device 170 denotes the client device that is locally connected to the devices and hardware providing real-time data streams.

In at least one embodiment, a user of the primary client device 170 logs in and creates a session. The user then selects reference data models 152 for the session and invites other users to join the session. A reference data model 152 is linked to the session and retrieved by the client device 170. The client device 170 loads the data model 152 and sets up the rendering scene and data model representations. Users of replicate client devices 170*a* can join a session they are invited to and can receive their data streams via device channels through WebSocket. Locally connected data devices and hardware are initialized and set up via their API. Data streams (locally or remote via WebSocket) from connected devices are received and used to update object representations and computations. Client devices 170 include devices such as, but not limited to, mobile devices, AR headsets, VR headsets, projector systems, and web browsers (such as laptops and tablets), for example. Accordingly and advantageously, in such embodiments, the system 100 provides sessions for a shared AR experience across multiple client devices 170, both local and remote.

Mobile devices include phones and tablets, where the camera and inertial measurement unit (IMU) sensors of these devices can be used to provide tracking and pose estimation between physical space and virtual space. Mobile devices can also support touch screen interaction, audio recording and playback, and communication endpoints such as Bluetooth, WiFi, and LTE. Current and future generations of Android and iOS devices support AR capabilities at the device and platform level.

Headsets are capable of providing spatial interaction, reconstruction, tracking, and pose estimation between physical space and virtual space via a comprehensive suite of sensors (e.g., accelerometers, gyroscopes, RGB+Depth cameras, microphones). Headsets can use stereoscopic rendering and semitransparent displays to merge virtual content with the real world. Headsets can also support user feedback via machine learning enabled interactions through voice and gestures interpreted through the sensors. Wireless communication capabilities of the headsets include Bluetooth and WiFi.

Projector systems can fuse virtual models with the real world by projecting the render window directly on a physical field. The projector can be treated as an inverse pinhole camera, where the virtual camera of the render window is matched to its intrinsics (e.g., optical center, focal lengths, and field of view) so that overlay between virtual and physical content can be spatially registered and visualized accurately. This may enable, for example, matching of a physical object and its virtual representation in location, orientation, and scale. Outside-in tracking can enable tracking of pico-projectors and updating of the virtual camera based on tracked poses.

Most modern browsers already support HTTP2 protocols as well as WebSocket. A connected camera device may provide a real-world stream for an AR overlay. Client applications can run in the browser utilizing web technologies such as WebGL and WebXR. Applications that run in standards conforming browsers are inherently cross-platform and can run across different devices, including mobile, headsets, desktops, and laptops.

Client device applications 172 can be built and deployed natively across devices, with common engines such as Unity or Unreal Engine, or with cross-platform browsers conforming to web standards such as WebGL and WebXR. The application 172 can consist of setup, update, and render loops, the implementation details of which are dependent on the choice of engines and SDKs used. In setup, data assets can be loaded to create their graphic primitives and representations, such as instantiation of vertices and faces and setting material properties such as specular, diffuse, and ambient color values. Virtual cameras can be set up to match the calibrated parameters of corresponding client device cameras to enable spatially accurate real-virtual overlay. In update-render loops, data from input devices can be used for computation and updating of position and orientation of data model graphic representations.

In at least one implementation, applications 172 are created using a game engine (such as Unity). For example, an application 172 is coded for both Android and iOS devices through Unity, creating one application 172 for both devices. Device-specific SDKs can then deploy the application 172 to the devices. Alternatively, device-specific applications 172 can be written in a more native way without the use of the game engine, but they can only then use the device SDKs and not any of the extra SDKs provided through a game engine. For example, separate applications 172 are coded for an iOS device using Xcode and for an Android device using Android studio, creating applications 172 that show the same information on the different devices.

The AR library 174 provides endpoints for the client application 172 that can, for example, acquire and set up models, broadcast and stream data including updated transforms of dynamic objects that are tracked, configure devices and track settings, and evaluate output metrics. The AR library 174 includes various software code organized into a set of classes or modules (i.e., classes that facilitate similar functions and processing), not limited to a single programming language in implementation. For example the various modules include an HTTP client module 176, a WebSocket client module 178, a registration module 180, a controller module 182, a devices module 184, a tracks module 186, a metrics module 188, a shaders module 190, and a classifiers module 192.

The HTTP client module 176 can handle requests/replies to the REST API endpoints of the HTTP server 112. These include authenticating and login of the user, querying and fetching of data, validation of fetched data against hashes, and session management. In some implementations, frameworks provide implementations of HTTP protocol out of the box or via third-party libraries.

The WebSocket client module 178 can broadcast and listen to other client devices 170 in device channels in a session 164. Device channel data streams can be sent and received as JSON strings. Recipient devices can parse the JSON string to extract the data frame, which can be sent to its corresponding track for propagation. The tracks module 186 can generate tracks that are agnostic to whether devices are physically connected, through WebSocket, or a loaded playback.

Advantageously, in at least one embodiment, the system 100 employs client devices 170 not only to display AR data, but also for tracking (e.g., of tools, cameras, hands, fingers, gestures), particularly in combination with external sensors for spatial computing and gesture/voice recognition, as well as providing real-time feedback of natural user interaction and instrument measurements relative to anatomy and plan. Client devices 170 may be connected to each other (e.g., wirelessly or through cabled Internet) through a session that enables data to be streamed across devices.

The registration module 180 can ensure that content is synchronized spatially and temporally across data and devices. The registration module 180 can provide functionality to co-register via spatial feature correspondences and manage data and devices across multiple coordinate systems by the use of scene graphs.

The controller module 182 can set up and activate devices that can interact in a session through a vendor device API, manage tracks to receive, record, and process device data streams, and synchronize data on the client device. The API can enable, for example, initialization, activation, and configuration of settings programmatically. The controller module 182 can use a high-resolution clock where each tick corresponds to updates using the devices module 184 and the tracks module 186. The clock may be an operating system level timer that can be used to timestamp received data, which are stored in buffers and can be interpolated or queried after for synchronization. As devices often have their own frame rate, a global clock can be used to synchronize data frames and help manage recording and playback of multiple data streams.

The devices module 184 can be used to provide data streams for consumption through a device API and exchange to the server 110 and with other client devices in the same session 164 via WebSocket. Each data stream message may include an identifier and an array of values. The various devices that interact with the server 110 may have their own device and data API from a vendor for initialization and data streaming. The devices may obtain data corresponding to hardware such as microphones, IMUs, navigation systems, eye trackers, spatial computing devices, video and camera devices, haptics, and touch-screens on mobile client devices 170, and package the data into the data streams. The devices may be on-board or external, communicating with the client device 170 via a physical link or through WebSocket.

IMUs can be used for pose estimation in AR applications and typically contain a minimum of 6 degrees of freedom (DoF). IMUs can stream measurements from an axis-aligned 3-axis accelerometer and a 3-axis gyroscope used to estimate relative position and pose (one view from the next).

Micro-electro-mechanical-systems (MEMS) sensors may be attached to camera-based devices to supplement pose estimation with computer vision techniques. They may also be attached rigidly to the body to capture dynamics, such as capturing motion of an anatomical structure and a disease in correlation with movement such as breathing.

Microphones can be used to provide audio data to enable audio-to-text dictation, recording of audio clips for annotation, voice control, and communication with other connected users.

Navigation systems, such as active or passive optical tracking, can be used to provide accurate and precise outside-in tracking across a large working volume. Sensors may be attached to client devices 170 or tools to enable optical tracking and guidance.

Eye trackers may be attached to headset devices or worn independently by the user along with a world-facing camera. Eye trackers can be used to provide eye tracking data to enable interactivity and manipulation of virtual models as well as gaze measurements which may be used in assessment of learners across tasks or to evaluate cognitive load.

Spatial computing devices may be attached rigidly to client devices 170 to provide inside-out tracking and gesture interaction. Spatial computing devices come in a variety of technologies, such as RGB-Depth cameras (structured light, time-of-flight) and wide-angle stereoscopic systems coupled with IMUs.

Video and camera systems can be used to enable different imaging modalities such as but not limited to endoscopy and ultrasound, for example. A video capture device can also be used to interface with a client device and stream video data (e.g., for remote advice and monitoring) through modern digital communication links.

Haptic devices can be used to provide feedback based on biomechanical models matched with surface representations and tracked instruments. The dynamics of a tracked instrument's position and biomechanical model can be used to modulate an output signal to the electromechanically coupled haptic device to produce feedback for the user. The biomechanical models include, for example, reference deformation and physics models, such as in Simulation Open Framework Architecture (SOFA). Surface deformation models can be tied to graphic primitives such as vertices or faces of a body's surface geometry then monitored and tracked with a depth camera (e.g., RGB-D).

Advantageously, in at least one embodiment, the system 100 provides tracking of surgical instruments, which can be fused with AR content and physical models. For example, suppose one part of a tool is tracked with outside-in or inside-out tracking. Since the system 100 knows the location and orientation of this part of the tool (e.g., the end), other parts of the tool can be calculated from this position (e.g., the tip of the needle or the end of the blade). The system 100 can be set up (or programmed) so that different AR content is viewed at these locations with the correct orientation, such as a plane at the end of the tool to give the user feedback on the blade position and orientation to confirm it is correct before proceeding with the cuts. The application 172 can facilitate the update and render loop. A camera on the client device 170 can provide data that is used to facilitate inside-out tracking. An external tracking camera can provide data that is used to facilitate outside-in tracking.

The tracks module 186 uses memory blocks to buffer and filter data streams from devices (e.g., live as connected physically, through a WebSocket client, or playback from recording). A buffer is a memory window that stores incoming samples with time stamps. Incoming data from data streams can be pushed into the buffer. Stored values can be used for interpolation based on controller clock tick for synchronization. Buffered data can also be used for smoothing or prediction via moving average filters or Kalman filter.

Advantageously, in at least one embodiment, the system 100 uses tracks to buffer and filter device data for broadcasting and synchronization across multiple clients in a session.

The metrics module 188 contains software code for evaluators that may be used on static or dynamic data to generate quantitative output for feedback and guidance in virtual walkthroughs, simulations, or live cases. Real-time data may be live from connected devices or may be recorded from the devices. Examples of real-time data include position and orientation of tracked surgical instruments (e.g., needle tip position and orientation, plane of cutting saw or osteotome, drill tip position and orientation, orientation and position of surgical plates/screws, and depth of cut or movement), or video streams from sources such as ultrasound or endoscopy systems.

Advantageously, in at least one embodiment, the system 100 provides real-time feedback of tracked surgical instruments, metrics module 188 relevant to a procedure or intervention, and a scoring assessment.

The shaders module 190 can be useful for AR rendering in a surgical context by providing real-time data without cluttering the visual field, which may be accomplished by computing visualization for vertex and geometry graphic primitives of a model object such as, for example, only visualizing the outline of an object rather than the entire virtual object. The shaders module 190 can contain OpenGL Shading Language (GLSL) and High-Level Shading Language (HLSL) implementations for non-photorealistic rendering. These include outline and silhouette shaders that can be applied to surface representations of anatomic structures, disease contours, and margins.

In at least one implementation, the shaders module 190 can adjust the transparency of objects so what is underneath the object can be seen, or display regions like a 2D outline with regions encircled by the outline being empty. The shaders module 190 can also turn the visibility of particular objects off if the user felt it was no longer necessary to see it, but allow the user to turn the object back to being visible at any point.

The classifiers module 192 can be used in AR rendering as well. The classifiers module 192 can contain pre-trained machine learning models that may be used across device data streams. These include, but are not limited to, at least one of ensemble models for hand gestures (e.g., adaptive boosting, decision trees, support vector machine (SVM), naïve bayes, random forest), motion localization across video frames, and single shot multi-box detectors for object detection. Training data of left- and right-hand gestures can be collected where each training sample for a hand is a feature vector of, for example, 28 values, including finger and joint positions, direction vectors of fingers and joints, and palm position and normal. Training can be performed via multiple classifiers, including decision trees, SVMs, adaptive boosting naïve bayes, and random forest. An aggregated classifier can pass input feature vectors to trained classifiers, with the majority result being stored in a circular buffer. The majority result of the circular buffer is the classification result that can be used by the system 100.

Figure 1B:
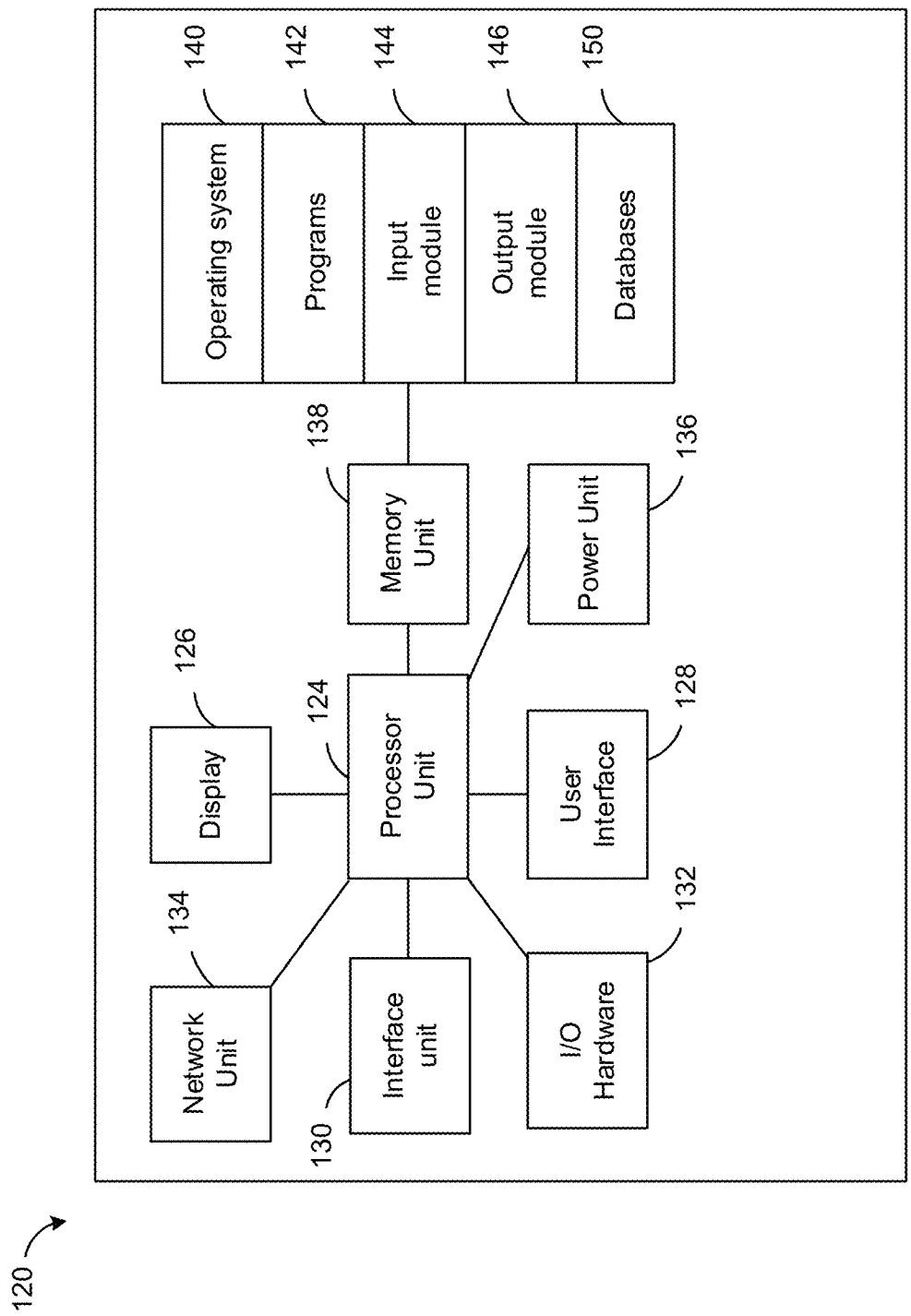
FIG. 1B shows an example embodiment of a server that can be used with the AR system of FIG. 1A.

Referring now to FIG. 1B, shown therein is a block diagram of an example embodiment of a server 120 that can be used with the AR system 100 of FIG. 1A. The server 120 may operate as the HTTP server 112, the WebSocket server 114, or both. The server 120 may run on a single computer, including a processor unit 124, a display 126, a user interface 128, an interface unit 130, input/output (I/O) hardware 132, a network unit 134, a power unit 136, and a memory unit (also referred to as "data store") 138. In other embodiments, the server 120 may have more or less components but generally function in a similar manner. For example, the server 120 may be implemented using more than one computing device.

The processor unit 124 may include one processor. Alternatively, there may be a plurality of processors that are used by the processor unit 124, and these processors may function in parallel and perform certain functions. The display 126 may be, but not limited to, a computer monitor or an LCD display such as that for a tablet device or a desktop computer. The user interface 128 may be an Application Programming Interface (API) or a web-based application that is accessible via the network unit 134. The network unit 134 may be a standard network adapter such as an Ethernet or 802.11x adapter.

The memory unit 138 may store the program instructions for an operating system 140, program code 142 for other applications, an input module 144, an output module 146, and the database 150. The programs 142 comprise program code that, when executed, configures the processor unit 124 to operate in a particular manner to implement various functions, tools, processes, and methods for the system 100.

In at least one embodiment, the AR system 100 allows real-time guided AR intervention (e.g., surgery) using metrics. Referring now to FIG. 46, shown therein is a flow chart of an example embodiment of a method of guiding AR intervention 4600 in the AR system 100 of FIG. 1A. Method 4600 provides steps (which may or may not occur in an order, and some of which may be processed concurrently) that may be carried out in whole or in part to guide AR intervention using the server 110, the primary client device 170, and a replicate client device 170*a*. The primary client device 170 and the replicate client device 170*a* each have their own processors and input devices that can generate real-time input data.

At 4610, the primary client device 170 receives model sets, an intervention plan having an intervention field, and session information about a session related to the AR intervention from the server 110.

At 4615, the primary client device 170 receives real-time input data from the input device of the primary client device 170. The real-time input data may include tracked input device information such as pose and position, as well as video and sound if the first input device has that capability. The input device may include an instrument (e.g., an osteotome or scalpel) and a tracker camera tracking the instrument and providing the pose/orientation data for the instrument.

At 4620, the processor of the primary client device 170 generates metrics by determining an evaluation of an execution of the intervention plan by comparing the intervention plan to the real-time input data. The metrics may be selected based on any of the metrics described herein or other appropriate metrics.

At 4625, the primary client device 170 displays real-time graphics based on the generated metrics that are spatially displayed over the intervention field. The real-time graphics may provide feedback on deviations between the tracked tool and the planned intervention.

At 4630, the primary client device 170 receives real-time status data from the server 110 about a replicate client device 170*a* connected to the server 110 after the replicate client device 170*a* joins the session. The replicate client device 170*a* can be used, for example, for remote interactions.

At 4635, the primary client device 170 sends the real-time input data through the server 110 to the replicate client device 170*a* within the session. The replicate client device 170*a* may receive the real-time input data and render a scene. Remote users may then view and gain insight into the scene that is seen by the user of the primary client device 170.

At 4640, the primary client device 170 sends the metrics and the evaluation computed from the intervention plan, through the server 110, to the replicate client device 170*a* within the session.

In at least one embodiment, the AR system 100 allows remote observation of a real-time guided AR intervention (e.g., surgery) using a replicate client device 170*a*. Referring now to FIG. 47, shown therein is a flow chart of an example embodiment of a method of remotely observing a guided AR intervention 4700 in the AR system 100 of FIG. 1A. Method 4700 provides steps (which may or may not occur in a certain order, and in some cases some of which may be processed concurrently) that may be carried out in whole or in part to guide and/or observe AR intervention using the server 110, the primary client device 170, and a replicate client device 170*a*. The primary client device 170 and the replicate client device 170*a* each have their own processors and input devices that can generate real-time input data.

At 4710, the replicate client device 170*a* receives the model sets, the intervention plan, and the session information about the session related to the AR intervention from the server 110.

At 4715, the replicate client device 170*a* receives the real-time input data, the metrics, and the evaluation broadcasted from the primary client device 170.

At 4720, the replicate client device 170*a* displays real-time graphics based on the model sets, the intervention plan, the real-time input data, the metrics, and the evaluation.

Method 4600 and method 4700 can be combined, in which case the steps of method 4600 may be considered the primary client device stage and the steps of method 4700 may be considered the replicate client device stage.

Additionally, method 4600 and method 4700 may be used by a plurality of replicate client devices 170*a*. When there is more than one replicate client device 170*a*, references to a replicate client device 170*a* in the steps to method 4600 and method 4700 can be interpreted as referring to one or more replicate client devices 170*a*. In such a case, at any point during the method 4600 or the method 4700, additional replicate client devices 170*a* may join or leave the session, such that at any given instant, there may be zero, one, or more replicate client devices 170*a* connected to the server 110.

In at least one embodiment, the AR system 100 allows real-time remote mentoring of the guided AR intervention. The remote mentoring can be accomplished by carrying out additional steps to those of method 4600. These additional steps are described as follows. (1) The replicate client device 170*a* receives real-time input data from the input device of the replicate client device 170*a*. The real-time input may help provide instruction and context from expert to novice. This may include, for example, selection of surface model regions, audio for vocal instruction, and/or tracked tool data in their local setup (e.g., the expert may have a 3D printed replica of the case, which their instruments are registered to and can demonstrate how to best approach/position the instrument). (2) The replicate client device 170*a* sends this real-time input data (received in the previous step) through the server 110 to one or more additional replicate devices connected to the server 110 and the primary client device 170. (3) The primary client device 170 receives this real-time input data (sent in the previous step) from the server 110. (4) The primary client 170 displays real-time graphics based on the real-time input data (received in the previous step) that originated from the replicate client device 170*a*.

Figure 2:
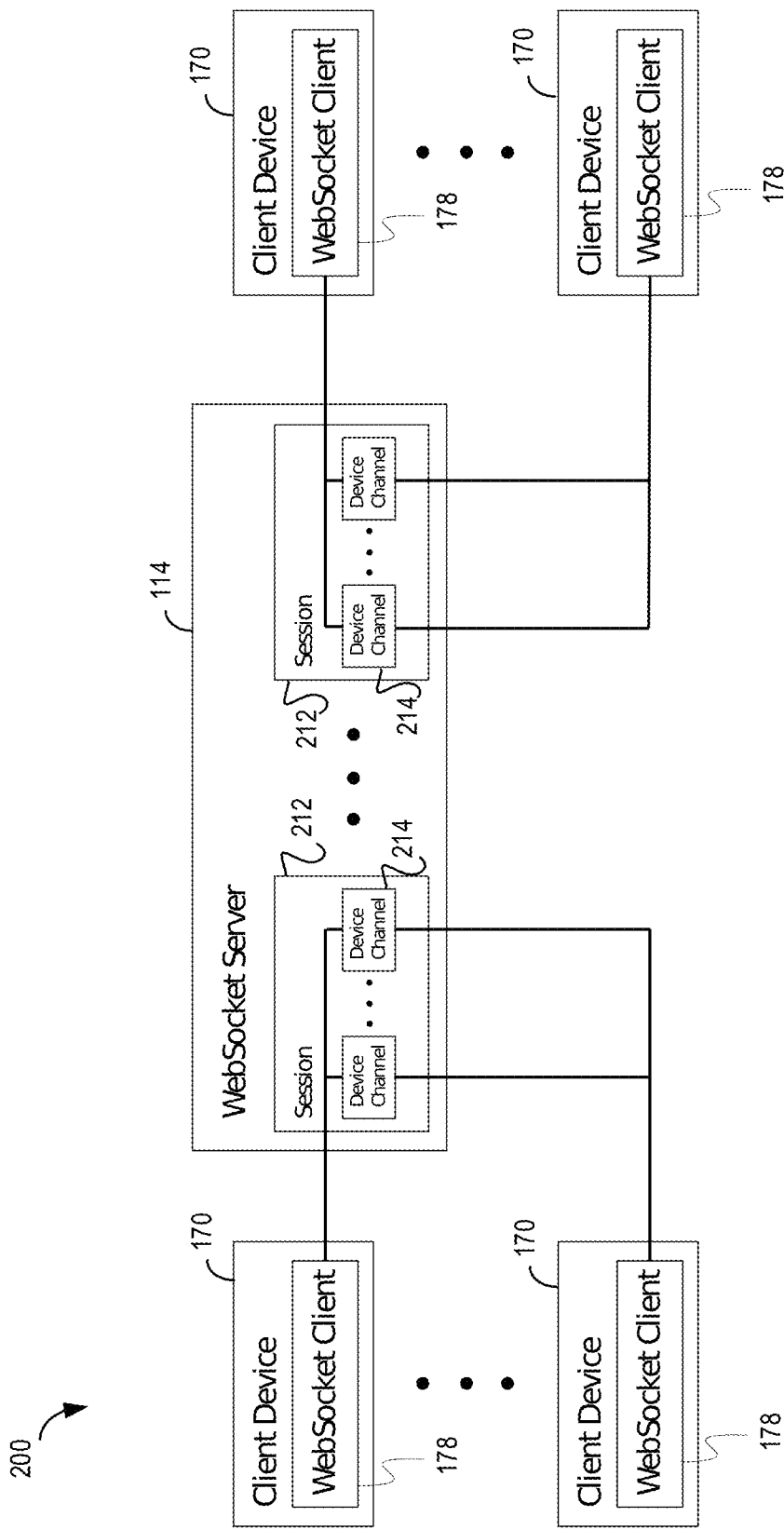
FIG. 2 shows an example embodiment of a multi-client configuration of a WebSocket server connected to client devices in the AR system of FIG. 1A.

Referring now to FIG. 2, shown therein is an example embodiment of a multi-client configuration 200 for a WebSocket server 114 connected to client devices 170 in the AR system 100. The server 110 can provide REST endpoints to client devices 170 for data exchange, synchronization, and streaming. The HTTP server 112 can provide endpoints for query and delivery of content, user authentication, and management of sessions 212. The WebSocket server 114 can enable multi-client broadcast of real-time data across device specific listening channels 214 (also referred to as device channels 214). The server 110 may be localized to different network sizes, such as those run on a computer on a siloed LAN and Wi-Fi SSID (operating room), across a hospital network, or deployed in the cloud so client devices 170 may connect remotely from different geo-locations. The client devices 170 may connect via a WebSocket client module 178 to a session 212 served or broadcast by the WebSocket server 114. The client devices 170 in the same session 212 may subscribe to the same device channels 214 where device data frames are broadcast and streamed.

Advantageously, in at least one embodiment, the system 100 utilizes the server 110 to store, retrieve, and update data models 152 (e.g., raw data, metadata), and broadcast real-time data across client devices 170, which may come from instruments and devices (e.g., video, two-way audio). The data and metadata can further adhere to the FAIR principles described above.

Figure 36:
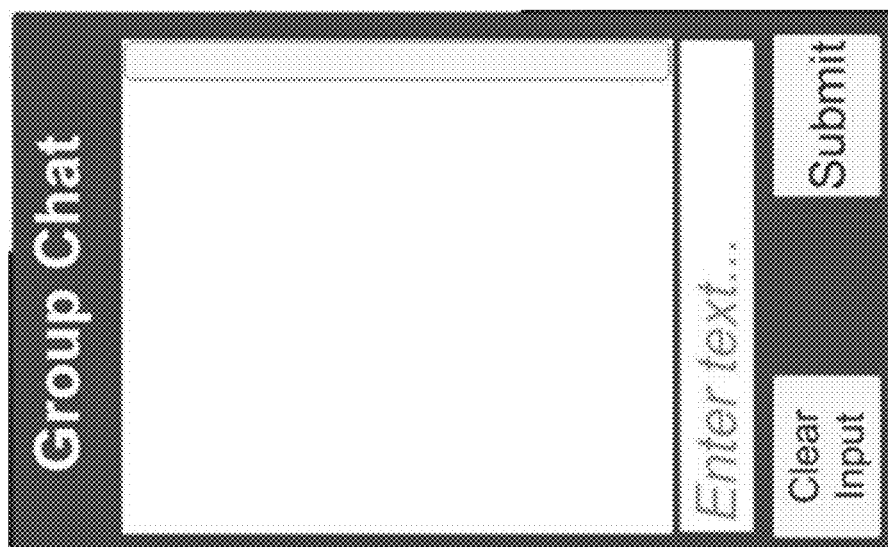
FIG. 36 shows an example layout of a chat window.

In at least one embodiment, the processors of each of the client devices 170 can generate a chat window that enables communication between all connected client devices 170. The chat window contains a field to view previously sent messages and an input field that allows for a message to be created. When the submit button is selected, the message contained in the input field is broadcast to all client devices through the server 110. An example layout of the chat window is shown in FIG. 36. The chat window can be minimized and receive messages even while not visible. There can be a maximum number of messages that are stored on the individual client devices 170 to minimize the amount of memory this feature requires. The messages may contain the username associated with the client device 170 and the message. The client devices 170 can be categorized and a message color assigned to each category. This can be done to improve readability of the messages.

Figure 37:
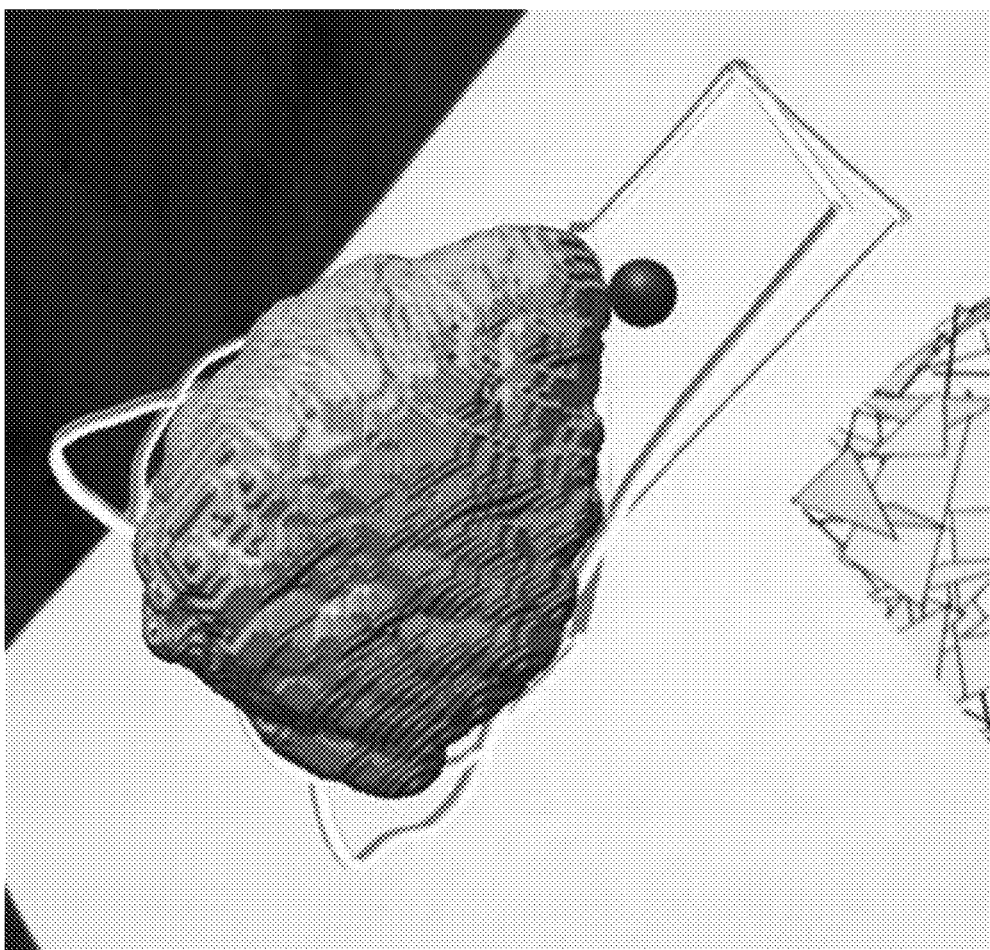
FIG. 37 shows an example of a sphere mesh appearing on a model set at the beginning of a procedure for creating a text annotation.
Figure 39:
FIG. 39 shows an example of the additional information viewable in the text annotation of FIG. 37.
Figure 38:
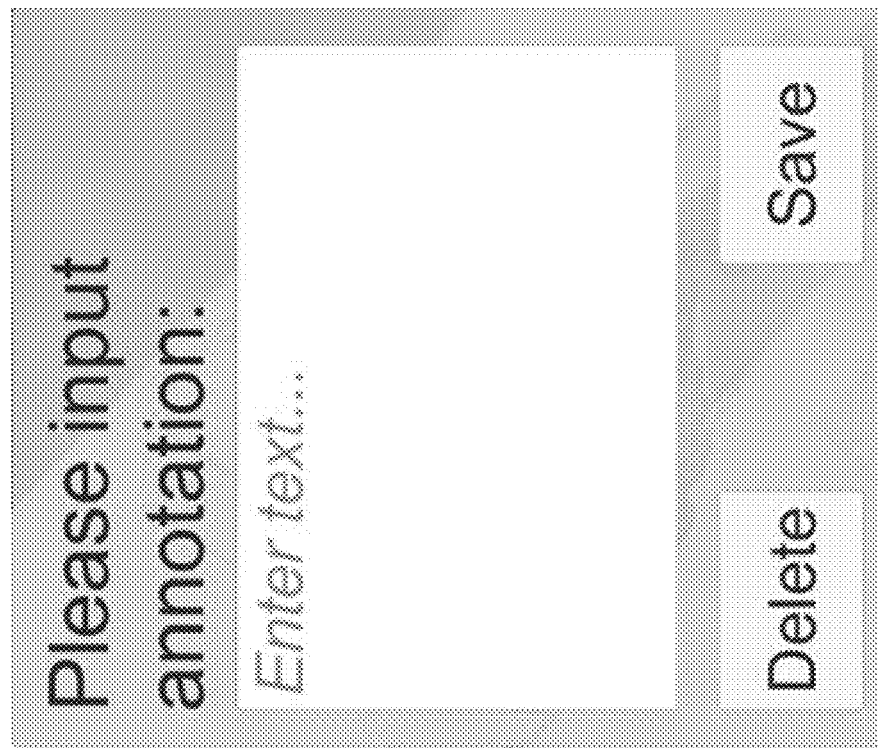
FIG. 38 shows an example of an input window to enter additional information for the text annotation FIG. 37.

In at least one embodiment, additional information relating to the visible model set can be created and sent to all connected client devices 170. Specific client devices 170 can have the feature of creating text annotations that are then broadcast to all connected client devices 170. The procedure for creating a text annotation is to enable the feature and then select a 3D point on the model set. For example, a visually distinct object, such as a sphere, can then appear across all client devices 170 at this position (e.g., as shown in FIG. 37). This allows all client devices 170 to visually see that one main client is adding additional information. The processor of the primary client device 170 can then generate a window to input associated text (e.g., as shown in FIG. 38). There can be options to delete the annotation or save it. Deletion of the annotation causes the sphere to be removed across all client devices 170. If the option to save is selected, the text is broadcast to all client devices 170, and the sphere changes color. This indicates that there is a message associated with the sphere mesh. The message can be viewed by selecting the sphere (e.g., as shown in FIG. 39).

Figure 40:
FIG. 40 shows an example of control of a client device viewpoint.

In at least one embodiment, a primary client device 170 has the feature of controlling the view point of all connected replicate client devices 170*a*. This feature enables all connected replicate client devices 170*a* to view the model set from the same position and orientation. The position data (e.g., in the form of a vector) and orientation data (e.g., in the form of a quaternion) of the primary client device 170 in regards to the physical model is calculated and then broadcast to the replicate client devices 170*a*. All replicate client devices 170*a* have the ability to view the model set independently from other replicate client devices 170*a*. This can be disabled, and the incoming position and orientation data can be used to move and orient the viewpoint of the replicate client device 170*a*. An example of such control of the client device viewpoint is shown in FIG. 40, where the view of the primary client device 170 is broadcast so that connected replicate client devices 170*a* have the same view.

Figure 3:
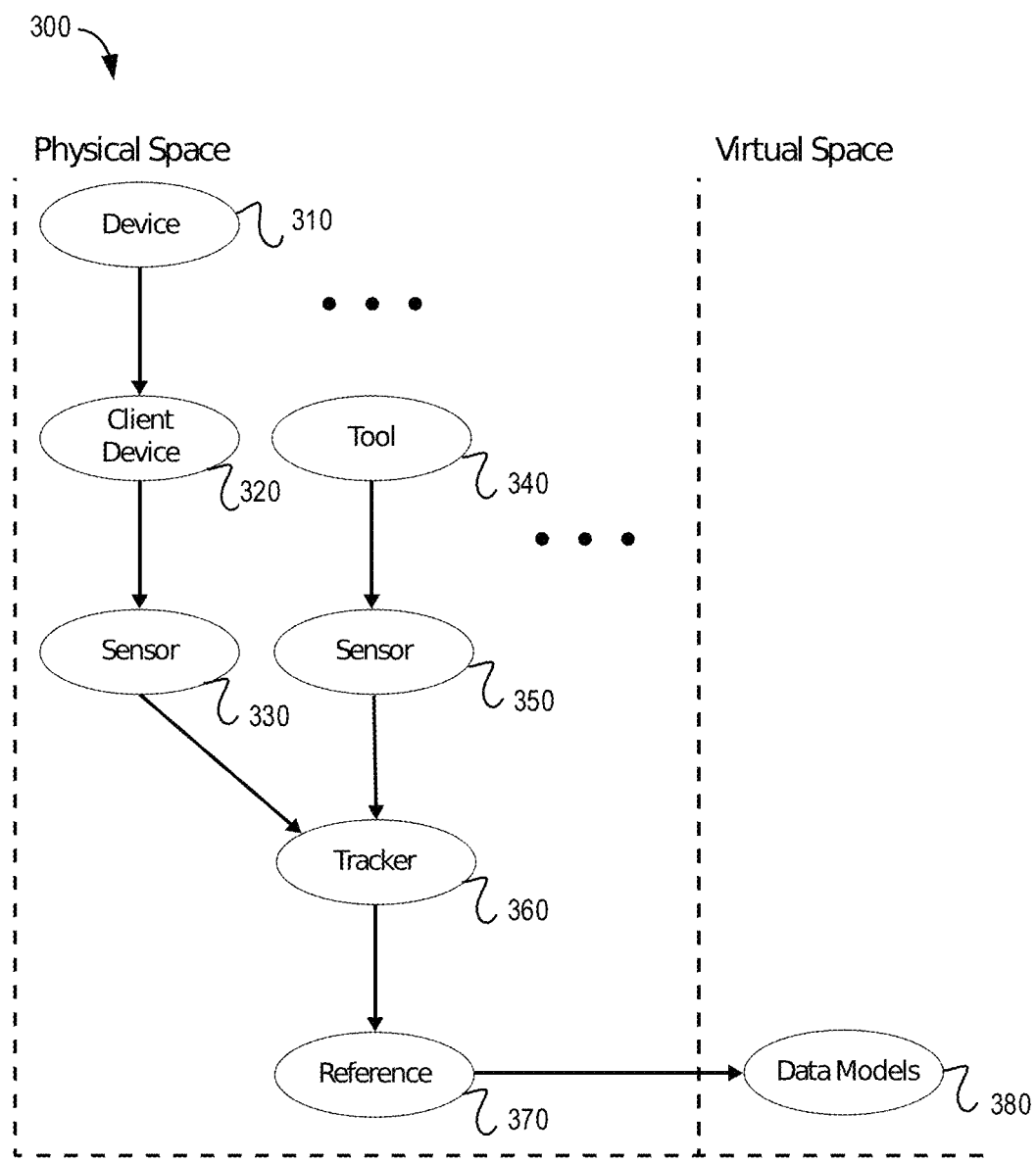
FIG. 3 shows an example of a scene graph for an outside-in navigation setup.

Referring now to FIG. 3, shown therein is an example of a scene graph 300 for an outside-in navigation setup. A tracked reference is attached rigidly to the body (e.g., adhesively to surface or anchored via screws). A tracked reference is an object of known geometry with designed identifiable features. The tracker detect and extract features determine the transform (e.g., rotation and translation) of the reference in the tracker node coordinate system. The geometry and features of a reference sensor or a reference marker is known a priori by design such as infrared spheres with known engineered spacing between each sphere or image marker with pre-computed scale and rotation invariant image features. Detected and extracted features from a tracking system are then matched to the features known a priori to determine the transform via homography, perspective-n-point, or rigid registration between 3D point correspondences. A registration transform maps points in the physical space (the reference sensor) to the virtual space (data models).

In at least one implementation, the tracked reference is a marker or a collection of infrared spheres that are detected by cameras. The attachment point depends on the object. For tools, this can be the end of the object so that it does not affect the user's ability to use the tool, and it is always visible to the cameras. These markers can be secured using various methods such as clamps, tapes, or screws, depending on what the body is.

Scene graphs are used to represent spatial relationships between model representations, devices, and tools. A node in the graph represents a coordinate system, and an edge between two nodes defines the transform between them. The directionality of the edge denotes how the transform is to be applied for traversal. Going along the direction (where directionality of the arrow is the forward transform and going against the arrow is the inverse transform) applies the forward transform, and going in the opposing direction applies the inverse transform. The transform is a 4×4 matrix containing the rotation and translation that maps a point from one coordinate system to the other.

In at least one embodiment, scene graph 300 represents an example embodiment of an outside-in navigation setup in which each node corresponds to a coordinate system in an outside-in tracking setup for client device 170. The scene graph 300 represents a tracking setup for AR-capable devices. This setup provides outside-in tracking. Outside-in tracking uses an external tracker to track sensors that are placed on a headset or another AR device in use to determine pose of the device. An external optical tracker with a large field of view can track active or passive optical sensors fixed rigidly to the client device 170 or clinical tools. In at least one implementation, tracking of the headset or mobile device is done using cameras that are placed around a room; the device itself does not calculate where it is but it might calculate its orientation depending on the device.

Node 310 represents the device coordinate system, which application 172 receives data streams from. The data streaming device is rigidly attached to the client device 170 and has a fixed transform to the coordinate system of the client device 170. Node 320 represents the coordinate system of the client device 170. Node 330 represents the coordinate system of a sensor attached to the client device 170 tracked by an external tracker. The edge between nodes 320 and 330 represents the transform to map a point in the client device coordinate system to the sensor. Node 340 represents the coordinate system of a physical tool or instrument. Node 350 represents the coordinate system of the sensor attached rigidly to the physical tool or instrument. The edge between nodes 340 and 350 represents the transform to map a point in the tool coordinate system to the attached sensor. Node 360 represents the external tracker coordinate system. Edges between nodes 330 and 360 and between nodes 350 and 360 represent the transforms that map a point in coordinate systems of sensor node 330 and sensor node 350 to the tracker. Node 370 represents the coordinate system of a reference sensor attached to a physical body. Node 380 represents the coordinate system of the virtual space and data model set. The edge between nodes 370 and 380 represents the transform that maps points in the physical coordinate system of the reference sensor to the virtual coordinate system.

Following the scene graph and concatenation transforms of edges traversed between source and destination nodes, the client device 170 may then map coordinates of a tool (node 340) or device (node 310) to data model coordinates (node 380) and display the virtual-space images of the device and the tool. The application 172 may generate the virtual-space images.

In at least one embodiment, the client device 170, having a processor, can carry out a method of outside-in tracking, the method comprising: receiving device image data at the processor from a first camera; determining device coordinates from the device image data using the processor; mapping the device coordinates to device sensor coordinates using the processor; mapping the device sensor coordinates to device-tracker coordinates using the processor; mapping the device-tracker coordinates to device-reference coordinates using the processor; applying a first registration transform to the device-reference coordinates using the processor to display the device in virtual space; receiving tool image data at the processor from a second camera; determining tool coordinates from the tool image data using the processor; mapping the tool coordinates to tool sensor coordinates using the processor; mapping the tool sensor coordinates to tool-tracker coordinates using the processor; mapping the tool-tracker coordinates to tool-reference coordinates using the processor; generating a virtual-space image of the tool by applying a second registration transform to the tool-reference coordinates using the processor; and displaying the virtual-space image of the tool on a display.

Figure 4:
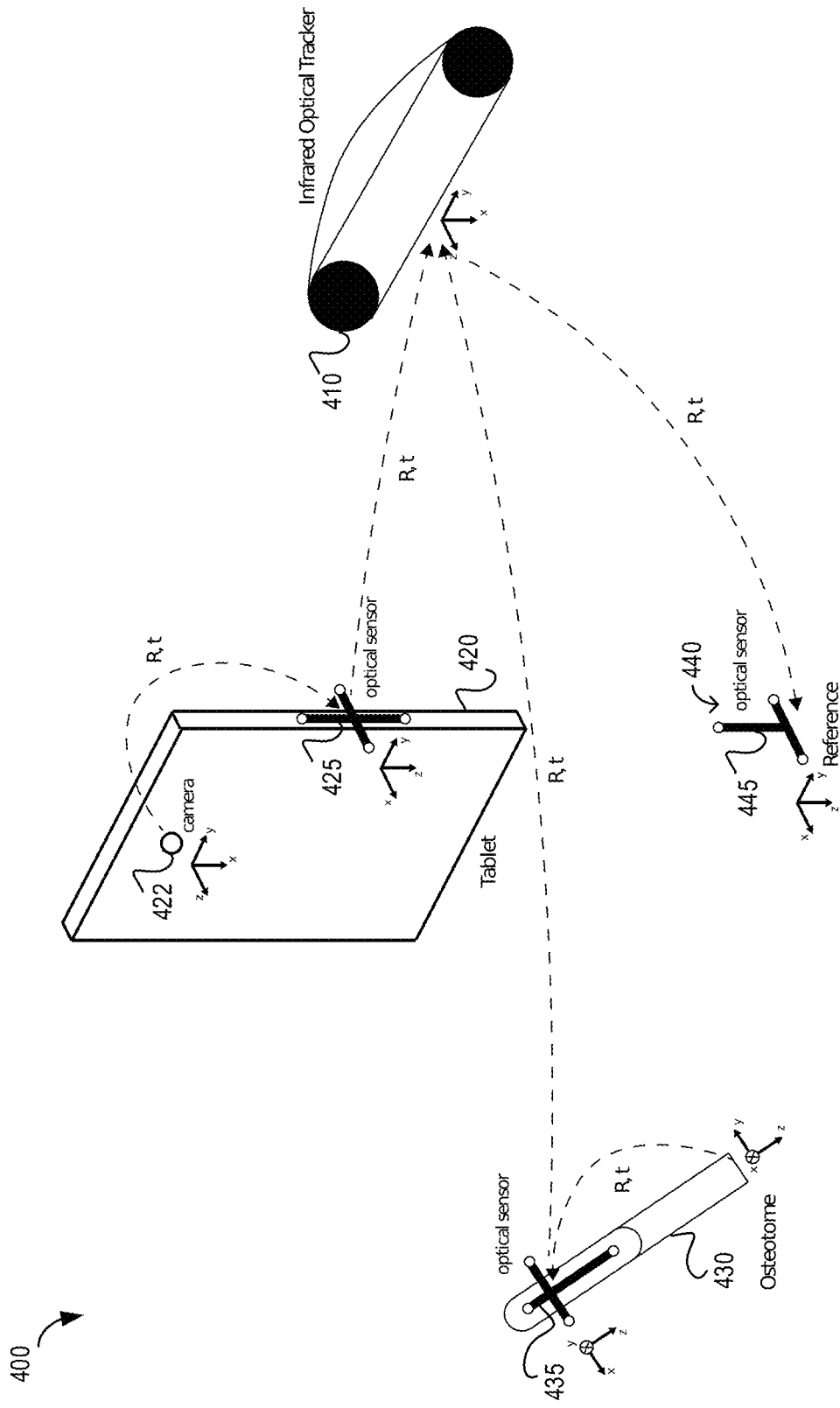
FIG. 4 shows an example of an outside-in tracking setup used in osteotomy.

Referring now to FIG. 4, shown therein is an example embodiment of outside-in tracking 400 used in osteotomy in which a tablet device is used with an osteotome that is tracked by an infrared optical tracker. An external system is used to track sensors that are attached rigidly to tools and client devices 170. Dashed lines show the directions that follow the scene graph 300 of FIG. 3. The external optical tracker is an infrared optical tracker 410. The client device 170 is a tablet 420 having a camera 422, and an optical sensor 425 that corresponds to sensor node 330. The osteotome 430 corresponds to the tool node 340 with the optical sensor 435 corresponding to sensor node 350. The transforms between the optical sensors 425, 435, the tablet 420, and the osteotome 430 are offset transforms that align the coordinates of the camera 422 (i.e., the origin of the camera corresponds to the device origin on mobile devices in the context of AR applications) and the coordinates of the osteotome 430 to their respective sensors. The infrared optical tracker 410 uses a reference 440, which has an optical sensor 445 that corresponds to reference node 370.

Figure 6:
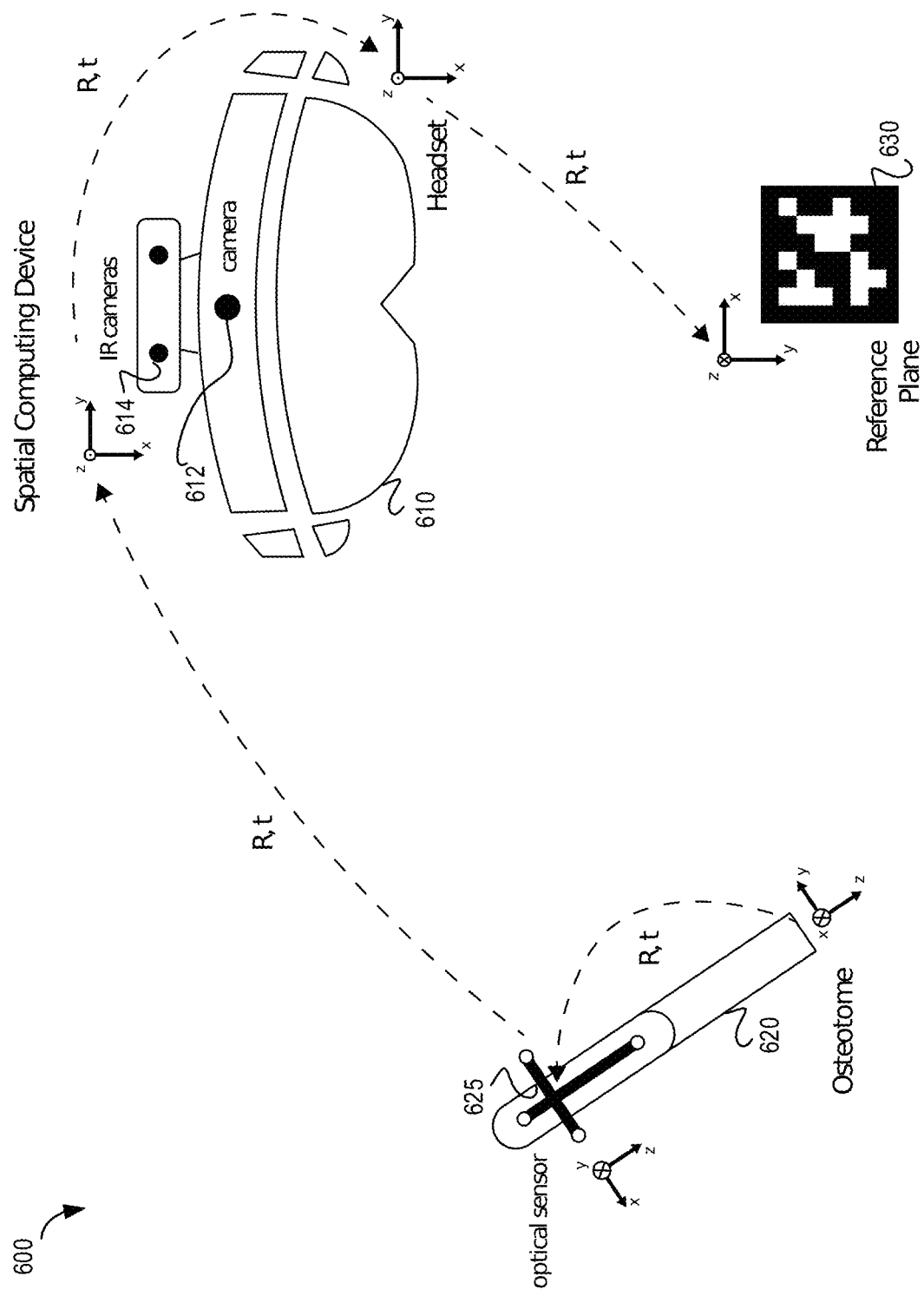
FIG. 6 shows an example of an inside-out tracking setup used in osteotomy.

In contrast to the traditional navigation setup, AR-capable devices may use inside-out tracking to provide tracking of reference sensors and pose estimation with an on-board device camera and IMUs. Additional spatial computing devices can be used to provide tool tracking, as they can provide a larger field of view, matching requirements of tool handling in the surgical field. An example of a headset device with an attached infrared spatial computing device is shown in FIG. 6 (described below). In that example, the client device 170 is the headset, and the device node 520 corresponds to the infrared spatial computing device.

Figure 5:
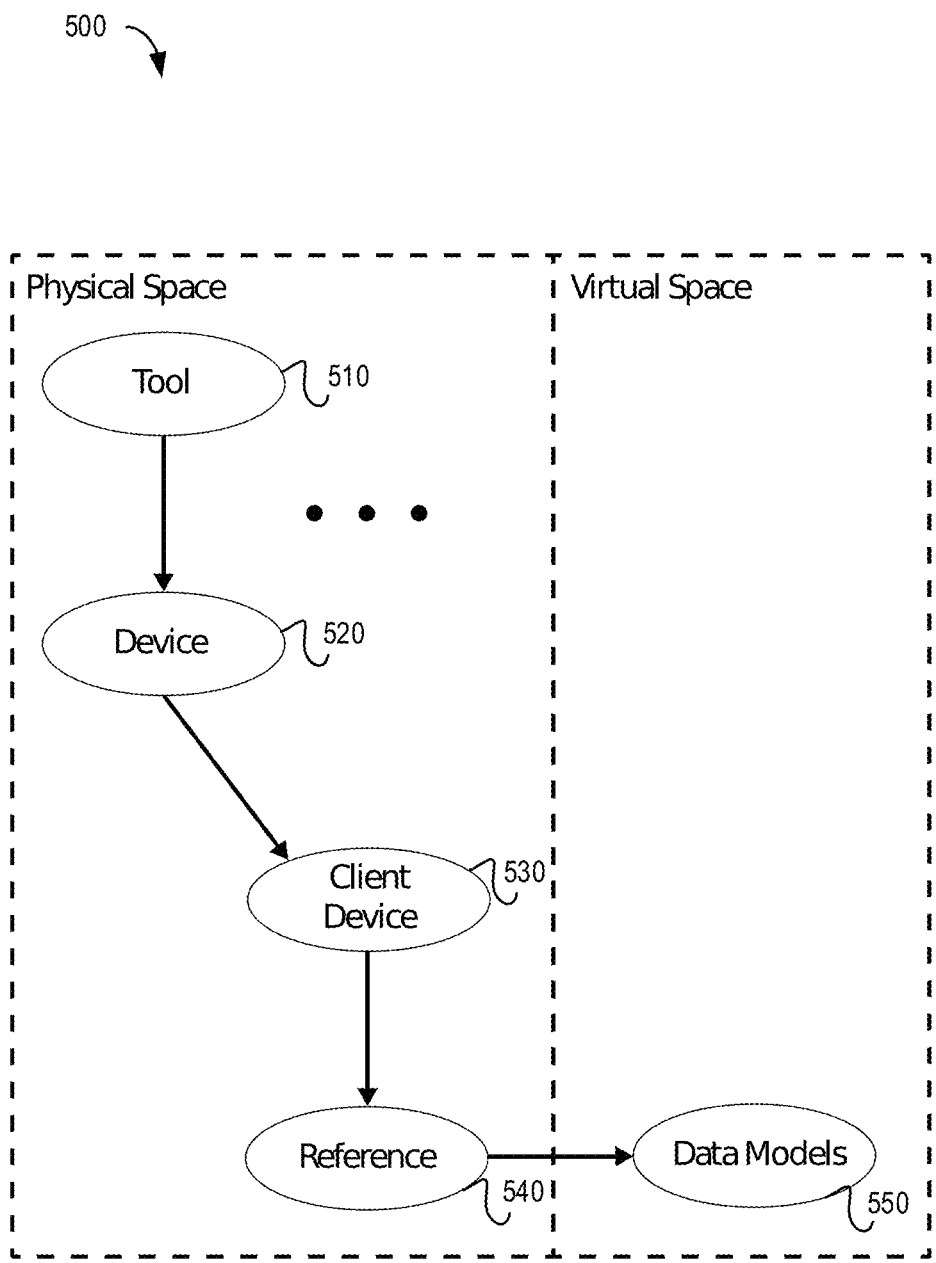
FIG. 5 shows an example of a scene graph for inside-out tracking.

Referring now to FIG. 5, shown therein is an example embodiment of a scene graph 500 which represents a tracking setup adapted to AR-capable devices for inside-out tracking. Inside-out tracking is where the sensors/camera are attached to the device (inside) and look out to the environment to calculate device position. This is contrary to outside-in tracking, whereby external sensors detect the device and calculate its position relative to their fixed position. One or the other, or both, may be used in various AR/VR devices. A camera of the client device 170 is used to track a reference sensor. A separate spatial computing device with a larger field of view (e.g., larger than the field of view of a headset or mobile device) is used to track tools using active or passive optical sensors that are fixed rigidly to the client device 170 or to clinical tools. Each node of the scene graph 500 corresponds to a coordinate system for the inside-out setup of client device 170.

Node 510 represents the coordinate system of the tool or instrument. Node 520 represents the coordinate system of the spatial computing device (e.g., an RGB-D camera or a stereo infrared camera). The edge between node 510 and node 520 represents the transform between the tool or instrument and the spatial computing device where the position and orientation of the tool or instrument is computed by the spatial computing device. Node 530 represents the coordinate system of the client device 170. The edge between node 520 and node 530 represents the fixed transform between the spatial computing device attached to the client device 170. Node 540 represents a physical reference in the space or attached to a body. The edge between node 530 and node 540 represents the transform between the client device 170 and reference as determined by the client device camera and detected features of the reference matched to features known a priori. Node 550 represents the coordinate system of the virtual space and the data model 152. The edge between node 540 and node 550 represents the transform that maps points in the physical coordinate system of the reference to the virtual coordinate system. Following the scene graph and concatenation transforms of edges traversed between source and destination nodes, the client device 170 may then map coordinates of the tool (node 510) to data model coordinates (node 550) and display the virtual-space images of the device and the tool. The application 172 may generate the virtual-space images.

Referring now to FIG. 6, shown therein is an example embodiment of an inside-out tracking setup 600 that can be used in osteotomy. A headset 610 using an attached infrared (IR) camera 614 (or, for example, a pair of IR cameras) is used to track a reference plane 630, and a spatial computing device is used to track a tool, such as an osteotome 620. The spatial computing device may be a dedicated RGB-D camera or stereo camera that captures information from the physical space to extract spatial information, for example, for tracking tools or features in the environment to extract a 3D pose estimation of the headset and/or detected objects. The headset 610 includes a (e.g., RGB-D) camera 612 and one or more IR cameras 614. The headset 610 corresponds to the client device node 530. The osteotome 620 corresponds to the tool node 510. The osteotome 620 has an optical sensor 625 attached thereon. The transforms between the optical sensor 625, the headset 610, and the osteotome 620 are offset transforms that align the coordinates of the camera 612 (i.e., the origin of the camera corresponds to the device origin on the spatial computing devices in the context of AR applications) and the coordinates of the osteotome 620. The camera 612 uses the reference plane 630, which corresponds to reference node 540. The reference plane is a physical version of an image marker, whose image features are computed a priori. The camera 612 can extract image features of video frames and match features to those computed a priori, where pose estimation of the camera 612 can then be computed via homography.

In at least one embodiment, the client device 170, having a processor, can carry out a method of inside-out tracking, the method comprising: receiving tool image data of a tool at the processor from a first camera; determining tool coordinates from the tool image data using the processor; mapping the tool coordinates to device coordinates using the processor; mapping the device coordinates to client device coordinates using the processor; mapping the client device coordinates to reference coordinates using the processor; generating a virtual-space image of the tool by applying a registration transform to the reference coordinates using the processor; and displaying the virtual-space image of the tool on a display.

The data models 152 used for AR applications (e.g., data models 380 and data models 550) can be co-registered prior to insertion and indexing to the database 150. This can be handled post image acquisition as part of the processing, segmentation, and optimization pipeline. Image volumes across different imaging modalities can be registered via common landmarks or via image-based methods including cross-correlation and mutual information.

An example of such registration of image volumes can arise with CT/MRI images of body parts. A CT or MRI image of a body part such as a face is scaled and translated based on common anatomic features. These may be intrinsic features such as a bony landmark or extrinsic features such as a fiducial marker, or a combination of these features in two dimensions and three dimensions. Fusing or overlaying images from CT and MRI where one or more common landmarks such as a bony prominence present in both images is used to align the images accurately and register the remaining information accurately in physical space (e.g., blood vessels and soft tissue tumor from MRI are fused/registered with CT data, which is better at bony reconstruction).

The exact scene graph configuration (e.g., scene graph 300 and scene graph 500) in AR is dependent on the client device and tracking configuration. For inside-out tracking (see, e.g., FIG. 5), mobile devices by themselves may rely on a camera and internal IMUs to provide tracking and infer device pose relative to a reference. Additional devices and sensors, such as RGB-D cameras, may be attached as well to the device for improved spatial reconstruction, sensing, and tracking of tools across a wide field. Many spatial devices are camera-based. Camera-based systems can be co-registered via relative pose calculations through perspective-n-point, homographies, random sample consensus (RANSAC), and Kalman filtering post device camera calibrations.

Device camera calibrations can calculate the intrinsics, distortion coefficients, and view angle of the camera. When virtual cameras in rendering pipelines are modeled as ideal pinhole cameras with zero distortion and their optical center located at the center of the render window, pixel mappings are calculated to map device camera frames to that of an ideal pinhole camera, correcting for optical center offset and distortion. Pose calculations of the calibrated ideal pinhole device camera can then be used to update the transform of the virtual camera, and overlay of data models 152 can be matched more accurately post mapping correction.

Figure 7:
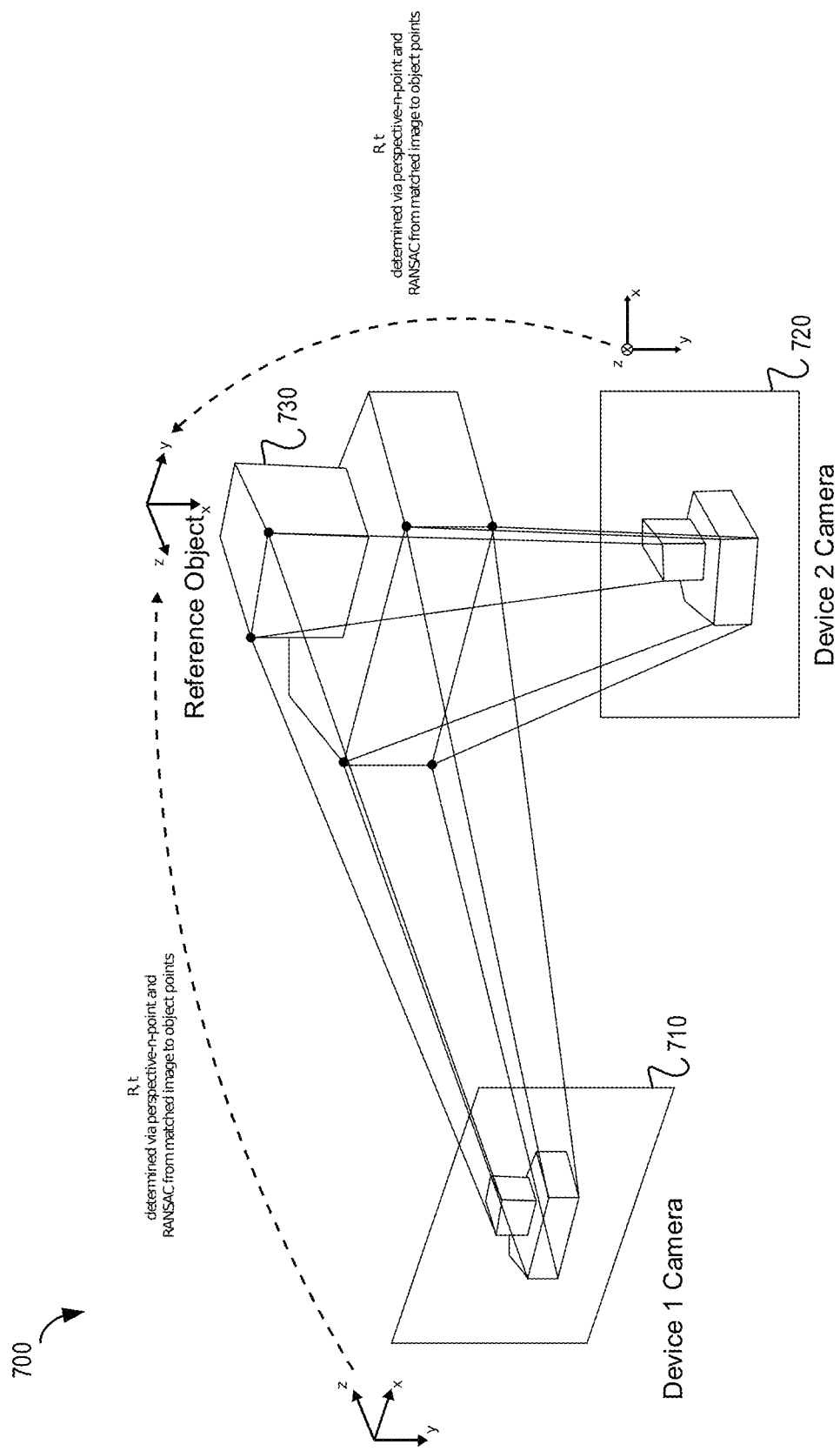
FIG. 7 shows an example of pose calculation of two camera devices viewing a common reference object with known coordinates and spatial points.

Referring now to FIG. 7, shown therein is an example of pose calculation 700 of two camera devices viewing a common reference object with known coordinates and spatial points. Pose can be recovered through perspective-n-point.

Given a reference object 730 with known spatial points matched to image points in a corresponding frame from device 1 camera 710, the camera pose with respect to the reference object 730 can be calculated through perspective-n-point. This can be repeated for additional attached camera devices, such as device 2 camera 720. For the two-device setup, this can create the scene graph relationship in FIG. 8 (described below), where device 2 camera 720 is rigidly registered to device 1 camera 710, where the registration transform is determined through the scene graph traversal from device 2 camera 720 to device 1 camera 710.

Figure 8:
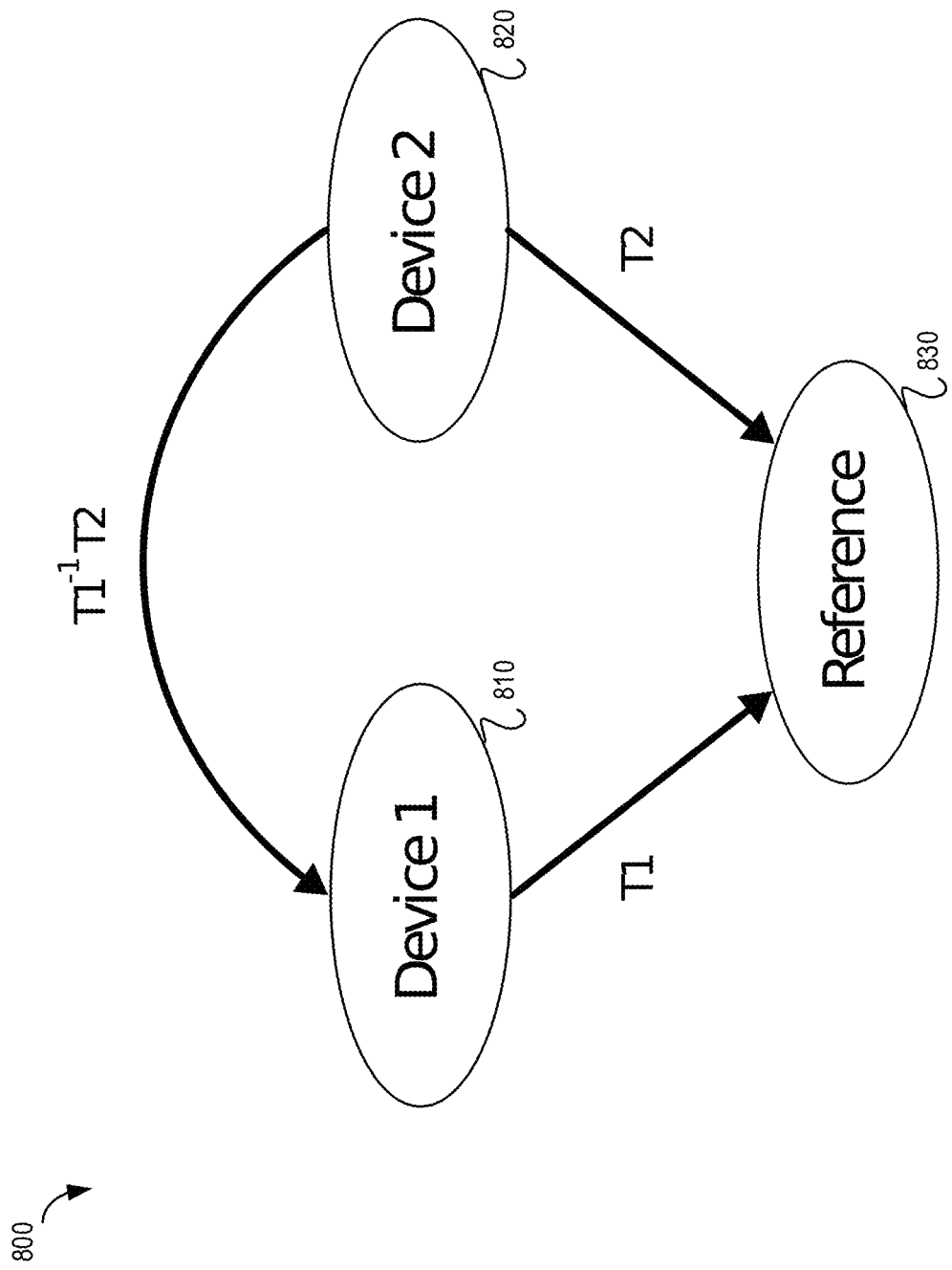
FIG. 8 shows an example of a scene graph equivalency for two devices viewing a common reference object.

Referring now to FIG. 8, shown therein is an example of a scene graph equivalency 800 for two devices viewing a common reference object. For camera-based systems that are rigidly attached, the device registration transforms are fixed and relative pose can be calculated via perspective-n-point or homography.

For reference planes with known spatial points, the camera pose relative to the reference plane can be determined with matched image and spatial points through homography. The registration transform is then determined through traversal of the scene graph.

In scene graph equivalency 800, a first registration transform T1 is applied to the spatial points from device 1 camera 810 viewing a reference 830. A second registration transform T2 is applied to the spatial points from device 2 camera 820 viewing the reference 830. The transform from device 2 camera 820 to device 1 camera 810 is therefore $T1^{-1}T2$ (where $T1^{-1}$ is the inverse of T1).

Figure 9:
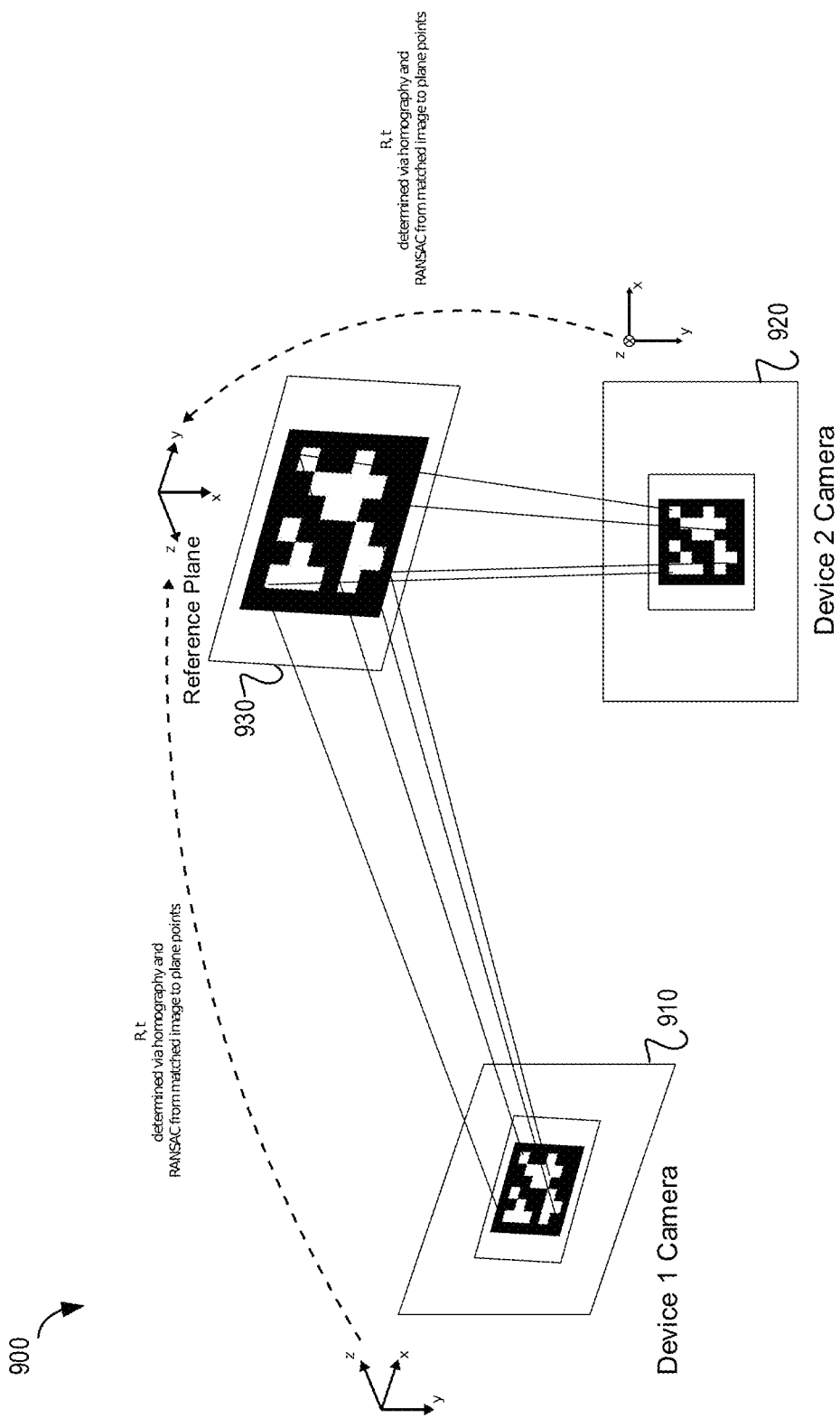
FIG. 9 shows an example of pose calculation of two camera devices viewing a common planar object with known coordinates and spatial points.

Referring now to FIG. 9, shown therein is an example of pose calculation 900 of two camera devices viewing a common planar object with known coordinates and spatial points. Pose can be recovered through homography.

Given a reference plane 930 with known planar points matched to image points in a corresponding frame from device 1 camera 910, the camera pose with respect to the reference plane 930 can be calculated through homography. This can be repeated for additional attached camera devices, such as device 2 camera 920. For the two-device setup, this can also create the scene graph relationship in FIG. 8 (described above), where device 2 camera 920 is rigidly registered to device 1 camera 910, and where the registration transform is determined through the scene graph traversal from device 2 camera 920 to device 1 camera 910.

Scene graph equivalency 800 may be used with pose calculation 900 in a manner similar to that used with pose calculation 700. Use of scene graph equivalency 800 can be modified depending on the type of reference 830 used. For example, for pose calculation 900, the registration transforms can be determined via homography and RANSAC from the matched image to plane points.

In at least one embodiment, the client device 170 can carry out a method of co-registration of spatial devices using one or more of pose calculation 700, pose calculation 900, and scene graph equivalency 800. The method begins with the client device 170 receiving a first frame of a reference object from a first camera. The application 172 determines first image points from the first frame. The application 172 determines a first camera pose by perspective-n-point or homography applied to the first image points matched to the first frame. The client device 170 receives a second frame of the reference object from a second camera. The application 172 determines second image points from the second frame. The application 172 determines a second camera pose by perspective-n-point or homography applied to the second image points matched to the second frame. The application 172 combines the first camera pose and the second camera pose to co-register the spatial devices.

For offset calculation between an attached sensor and a tool, certain modifications may be required. Multiple measurements can be collected between the sensor and an anchored reference point with the tip of the tool touching the reference point. The translation offset between the sensor and the tip of the tool can then be calculated through optimization of the system of equations across collected measurements. Alternatively, or in addition, a pre-calibrated pointer tool may be used to touch the tool tip with the sensor acting as the reference.

Virtual and physical models may be registered using known spatial points (fiducials or anatomic landmarks), requiring a minimum of 3 common points, or via surface methods including iterative closest point (ICP) and 4-point congruent sets (4PCS).

Registration with known spatial points may require identifying matched pairs of points on the physical model and the surface or volume representation of the virtual model. Physical model points may be selected via a tracked and calibrated pointer tool.

For surface-based registration, point clouds of the physical model from spatial computing devices (e.g., stereoscopic, RGB-D, time-of-fight cameras) can be registered to the surface representation of a virtual model via 4PCS and ICP.

Object tracking of a known reference object or planar marker may be achieved through perspective-n-point or homography as mentioned above (see, e.g., the method of co-registration of spatial devices). In the context of object tracking, the device can be continuously updating its relative pose with respect to the tracked reference as opposed to determining a fixed rigid relationship between two devices viewing the same reference. The tracked object or planar marker may be of a fixed relationship to a physical model, or the physical model may be tracked itself through feature correspondence.

Deformation tracking can be achieved via RGB-D cameras where RGB frame pairs of matched image features have corresponding depth image values. A depth image value corresponds to a point in the point cloud which is registered to a vertex and polygons in the surface representation of the virtual model. Thus, tracking point cloud changes can be used to compute corresponding mesh dynamics from frame to frame.

Inside-out tracking may be facilitated via client device APIs and platform SDKs. These include ARKit on iOS devices and ARCore across Google devices.

For generalized camera-based tracking, a high-contrast image may be used for planar marker tracking, where reference image features are known a priori as spatial points on the plane. Matched spatial points and image points in a frame may then be used to calculate camera pose via homography.

Tracking of infrared reflective passive spheres can be accommodated by an attached spatial computing device with an infrared sensor. In a stereoscopic setup, a circular Hough transform can first be applied to locate marker centers. Then centers can be matched according to epipolar geometry. Matched centers can then be triangulated to determine centers in 3D. A sensor definition can be expressed as a distance graph between labelled markers. Post triangulation, a distance graph may be constructed and matched to the definition distance graph to extract a marker ID.

Outside-in tracking can be enabled by attaching passive or active sensors to client devices and tools.

Figure 10:
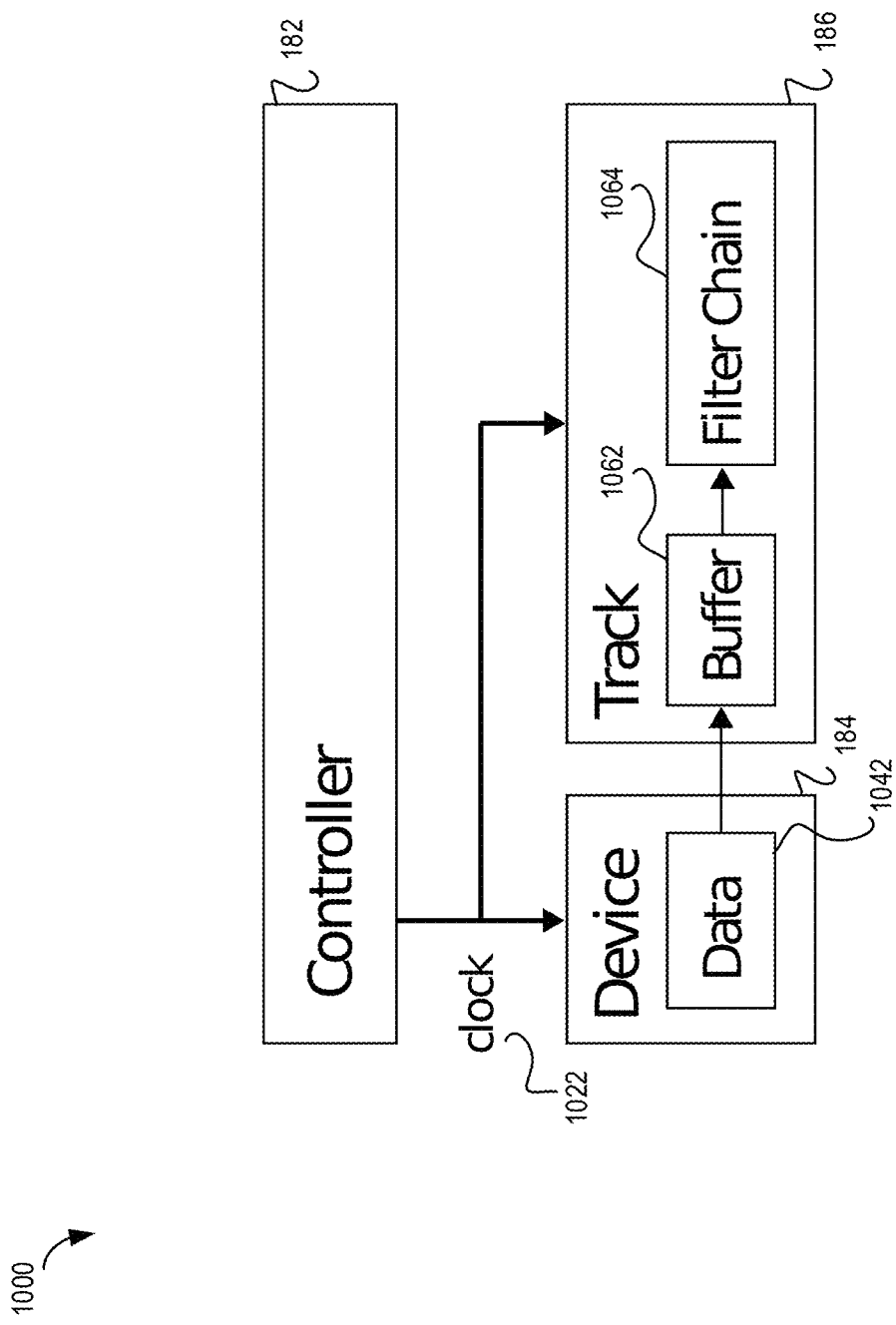
FIG. 10 shows an example of a controller connected to a device and a corresponding buffer.

Referring now to FIG. 10, shown therein is an example of a controller configuration 1000 of the controller module 182 interacting with the devices module 184 and the tracks module 186. In controller configuration 1000, the controller module 182 generates a clock tick 1022 to propagate data 1042.

The controller module 182 can be responsible for setting up and activating devices via the devices module 184, the management of tracks through the tracks module 186, and synchronizing data 1042 on the client device 170. The controller module 182 can use a high-resolution clock where each clock tick 1022 corresponds to updates using the devices module 184 and the tracks modules 186. As input devices 184 of a client device 170 often have their own frame rate, a global clock on client device 170 can be used to synchronize data frames and help manage recording and playback of multiple data streams.

Live client devices 170 can run simultaneously at different frame rates. Time-stamped data from the devices module 184 can be stored in a buffer 1062 provided by the corresponding tracks module 186 of the client device 170. This also corresponds to the data frame broadcast to device channels via WebSocket. For client devices 170 listening on the WebSocket device channel, the data frame can be parsed and then stored in the buffer of their respective device tracks.

On a controller clock tick 1022, the closest data frame from the buffer 1062 can be propagated through a filter chain 1064.

For recorded data, playback devices can simulate the output format of a real device with data parsed and snapped to controller clock ticks 1022. Unlike live devices, playback devices can propagate data based on the controller's clock.

The tracks are containers that buffer and filter a data stream from client devices 170 (live as connected physically, through a WebSocket client, or playback from recording).

Every tracks module 186 can use a buffer 1062 that is filled by the time-stamped data from its corresponding device. Each data frame in the buffer 1062 can be a vector of values. On a controller clock tick 1022, the data frame from the buffer 1062 can be propagated through the filter chain 1064. The final filter output can be passed along to the AR application for consumption and to evaluate against desired metrics.

Filters that process input data frames can be chained to process device data in sequence. Common filters include moving average, Kalman filter, N-step delay, thresholding, and remapping filters via look-up tables and transfer functions.

For video frames, filters include grayscale, motion detection, focus measure, screenshot, convolution, smoothing, sharpening, edge detection, circular Hough transform, and remapping filters.

Data streams in video tracks can be 2D arrays (e.g., video frames) rather than vectors.

Annotation tracks can be tracks that are generated through interaction with the system 100 by the end user. These may be audio and dictation as captured through the microphone or gestures.

An automation track can capture all events and parameter changes snapped to the refresh rate and controller clock tick 1022.

This enables, for example, playback of the recording exactly as the interactions, performance, and execution took place with the system 100. This functional utility mirrors automation tracks used in audio production systems (such as captured MIDI control parameters and values).

During playback, the controller module 182 can sequence events and actions as parsed from the recorded automation track. These include setup and control of the playback devices and management of filter chains 1064 and parameters across tracks according to how they were recorded in sequence.

In at least one embodiment, the client device 170 can carry out a method of controlling the operation of devices module 184 and tracks module 186, using controller configuration 1000. The method begins with the controller module 182 generating controller clock ticks 1022. The controller module 182 receives a first plurality of input data from a first input device having a first set of corresponding time stamps determined from the controller clock ticks 1022. The controller module 182 receives a second plurality of input data from a second input device having a second set of corresponding time stamps determined from the controller clock ticks 1022. The controller module 182 stores the plurality of input data in a buffer 1062 using its corresponding tracks module 186. The controller module 182 sends each of the plurality of input data to a filter chain 1064 at different controller clock ticks 1022. The filter chain 1064 generates a first plurality of filter chain output of processed first input data and a second plurality of filter chain output of processed second input data. The controller module 182 generates a plurality of data frames based on the first plurality of filter chain output and the second plurality of filter chain output along with the first set of corresponding time stamps and the second set of corresponding time stamps. The client device 170 sends each of the plurality of data frames and time stamps to the server 110 through the WebSocket client module 178. The client device 170 outputs each of the plurality of data frames to an AR application 172.

In at least one embodiment, the client devices 170 and the server 110 can carry out a method of maintaining synchronization of real-time input data for broadcast and session logging functions. The method beings with the primary client device 170 generating first clock ticks. The server 110 receives a first plurality of data frames from the input device of the primary client device 170, which have a first set of corresponding time stamps determined from the first clock ticks. The replicate client device 170a generates second clock ticks. The server 110 receives a second plurality of data frames from the input device of the replicate client device 170a, which have a second set of corresponding time stamps determined from the second clock ticks. The server 110 combines the plurality of data frames based on the first plurality of data frames and the second plurality of data frames along with the first set of corresponding time stamps and the second set of corresponding time stamps, including the server time stamps at time of receiving the data frames. The server 110 outputs the combined data frames and time stamps for storage and/or broadcast.

In at least one embodiment, the client devices 170 and the server 110 can carry out a method of synchronizing devices and tracks of a multi-user AR collaboration. The method begins with the primary client device 170 storing the first real-time input data in a first buffer in corresponding first device tracks. A track (which may be part of the device tracks) may be, for example, a signal flow from an input device, starting from input data in the buffer. The primary client device 170 generates first clock ticks. The primary client device 170 processes the first real-time input data in the first buffer through a first filter chain from the first clock ticks. A filter chain may be, for example, a sequence of steps that transforms an input signal where the output of a previous step routes to the input of the next step. The primary client device 170 generates first data frames from the first filter chain. The server 110 receives the first data frames from the primary client device 170 having a first set of corresponding time stamps determined from the first clock ticks. The replicate client device 170a stores the second real-time input data in a second buffer in corresponding second device tracks. The replicate client device 170a generates second clock ticks. The replicate client device 170a processes the second real-time input data in the second buffer through a second filter chain from the second clock ticks. The replicate client device 170a generates second data frames from the second filter chain. The server 110 receives the second data frames from the replicate client device 170a having a second set of corresponding time stamps determined from the second clock ticks. The server 110 generates combined data frames based on the first data frames and the second data frames along with the first set of corresponding time stamps and the second set of corresponding time stamps. The server 110 stores the combined data frames in the database 150.

In at least one embodiment, the client devices 170 and the server 110 can use the plurality of data frames stored in the database. The method begins with the server 110 retrieving the combined data frames from the database 150. The server 110 generates output clock ticks. Each of the clock ticks may be programmatically determined by checking against the operating system (OS) clock. The OS clock is continuously running, and a clock tick corresponds to an event where a set frequency/interval match an elapsed time on the OS clock. The server 110 extracts a primary client data frame and a primary client time stamp from the combined data frames for the primary client device 170 corresponding to a current output clock tick of the output clock ticks. The server 110 extracts a replicate client data frame and a replicate client time stamp from the combined data frames for the replicate client device 170a corresponding to the current output clock tick. The server 110 combines extracted data frames of the primary client device 170 and the replicate client device 170a between server time stamps corresponding to the current and previous output clock ticks. The server 110 broadcasts combined output data frames along with corresponding time stamps to the primary client device 170 and the replicate client device 170a.

In at least one embodiment, the client devices 170 and the server 110 can carry out a method of controlling devices and tracks of a multi-user AR collaboration. The method comprises: generating clock ticks; receiving a first plurality of input data from the primary client device 170 into a buffer; determining a first set of corresponding time stamps from the clock ticks; processing first buffer data from the buffer on the clock ticks to generate a first plurality of data frames along with the first set of corresponding time stamps; receiving a second plurality of input data from the replicate client device 170a into the buffer; determining a second set of corresponding time stamps determined from the clock ticks; processing second buffer data from the buffer on the clock ticks to generate a second plurality of data frames along with the second set of corresponding time stamps; sending the first plurality of data frames and the first set of corresponding time stamps to the server 110; sending the second plurality of data frames and the second set of corresponding time stamps to the server 110; and outputting each of the plurality of data frames to an AR application.

Advantageously, in at least one embodiment, the system 100 provides recording and playback of device data fused with AR content, including annotations with spatial/temporal context, and feedback of device data with respect to a plan (i.e., surgical, intervention, guidance, or education).

Figure 11:
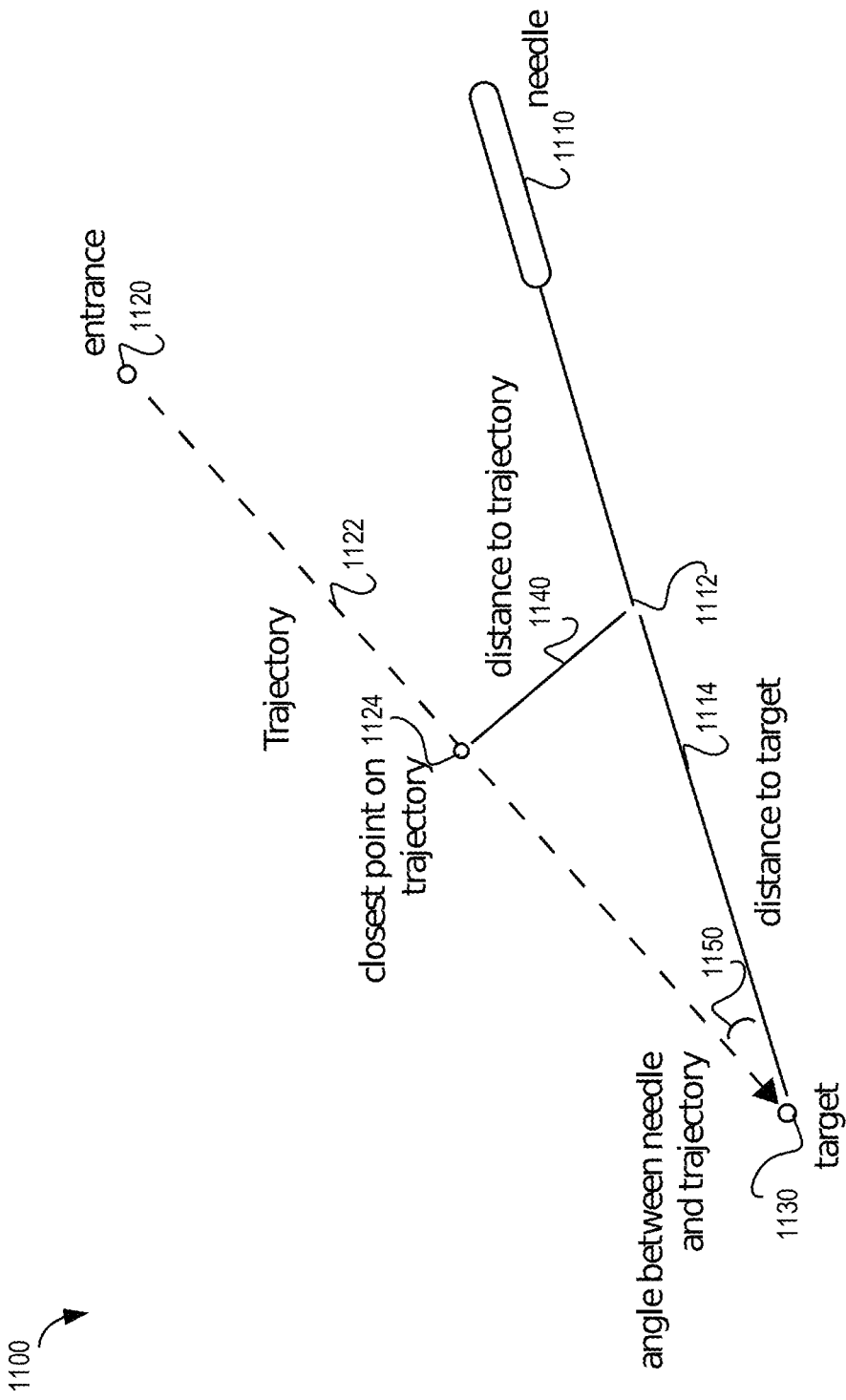
FIG. 11 shows an example of metrics used in needle guidance.

Referring now to FIG. 11, shown therein is an example of metrics used in needle guidance 1100.

The metrics module 188 contains software code for evaluators that may be used on static or dynamic data to generate quantitative output for feedback and guidance in virtual walkthroughs, simulations, or live cases. Real-time data may be live from the devices module 184 of connected devices or recorded from the devices module 184. Examples of real-time data include position and orientation of tracked surgical instruments (e.g., needle tip and orientation, plane of cutting saw or osteotome), or video streams from sources such as ultrasound or endoscopy systems.

Surface or volumetric data may be collected after execution of a procedure to co-register with pre-op or intraoperative datasets and surgical plans. These may include surface models of the ex-vivo specimen and patient as captured by a spatial computing device (e.g., stereoscopic cameras, RGB-D cameras) or ex-vivo and post-op imaging across CT, MR, etc. Registered post-op and ex-vivo datasets to model sets records 154 and plans records 156 used during intervention can provide an assessment of execution via volume and mesh intersections.

Certain volume operations can assist in quantitative assessments of performance with respect to volume representations. Common volume operations include morphology operations such as dilation and erosion, and Boolean operations such as union and intersect. Dilation volumes can be stored beforehand in model sets records 154 to define planning volumes, such as Planning Target Volume (PTV) in radiation therapy, negative margin volumes in surgical oncology, or warning/no-fly zones around anatomical structures. However, they can be adjusted during a session 164 based on requirements and constraints.

Dilation and erosion, for example, expand and shrink the volume under operation. Dilation can be used to expand a volume by a specified amount and be used in defining negative margin boundaries and ablation volumes.

The intersection of two volumes can be defined by voxel pairs using the Boolean AND operation. The union of two volumes can be defined by voxel pairs using the Boolean OR operation.

Mesh operations include splitting a polygonal mesh via a cut plane and calculating the intersection between a cut plane and a mesh, Boolean operations can be used to calculate union and intersection between meshes, mesh simplification and reduction, spatial smoothing, and space portioning operations to query an intersection with a given trajectory.

A needle 1110 (or needle-like instrument) can be defined by its direction aligned with its z-axis. Given a set of trajectories, the needle guidance 1100 can relay needle poses to an active planned trajectory 1122 as defined by an entrance point 1120 and a target 1130.

Metrics for needle procedures include a first distance 1114 between a needle tip 1112 and the target 1130, an angle 1150 between the needle 1110 and the planned trajectory 1122, a second distance 1140 between the needle tip 1112 and a closest point 1124 along the trajectory 1122, and an intersecting point with the plane (not shown).

For ablative procedures, ablation volume can be calculated at the needle tip. Coverage can be calculated with updated needle poses by the intersection of the ablation and lesion volumes.

Figure 12:
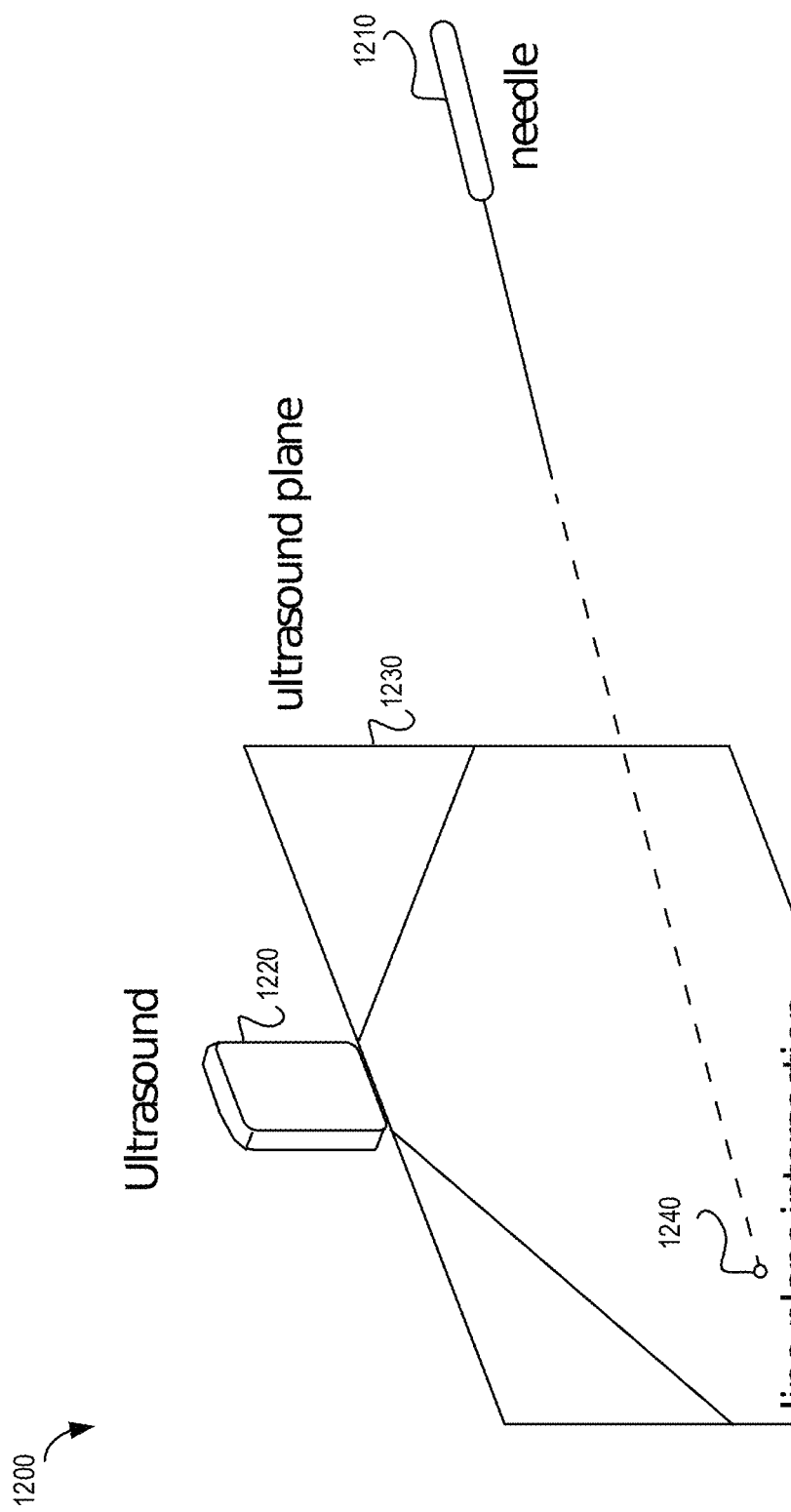
FIG. 12 shows an example of an intersection of a needle with an ultrasound plane enabling out-of-plane advancement of the needle.

Referring now to FIG. 12, shown therein is an example plane intersection 1200 where an intersection of a needle 1210 with an ultrasound plane 1230 enables out-of-plane advancement of the needle 1210.

Plane intersection 1200 can be useful when a needle procedure is performed under ultrasound guidance. A calibrated and tracked ultrasound probe 1220 can register ultrasound video frames to the probe tip. Tracking may be done via sensor attachments onto the ultrasound probe 1220 such as infrared reflective fiducials or small radiofrequency coils. Thus, needle tracking with the tracked ultrasound probe 1220 can provide out-of-plane guidance towards an intended line-plane intersection 1240. This can provide a significant advantage when combined with anatomical representations of surrounding structures from other modalities as traditionally needle advancement under ultrasound are constrained to be in-plane.

Figure 13:
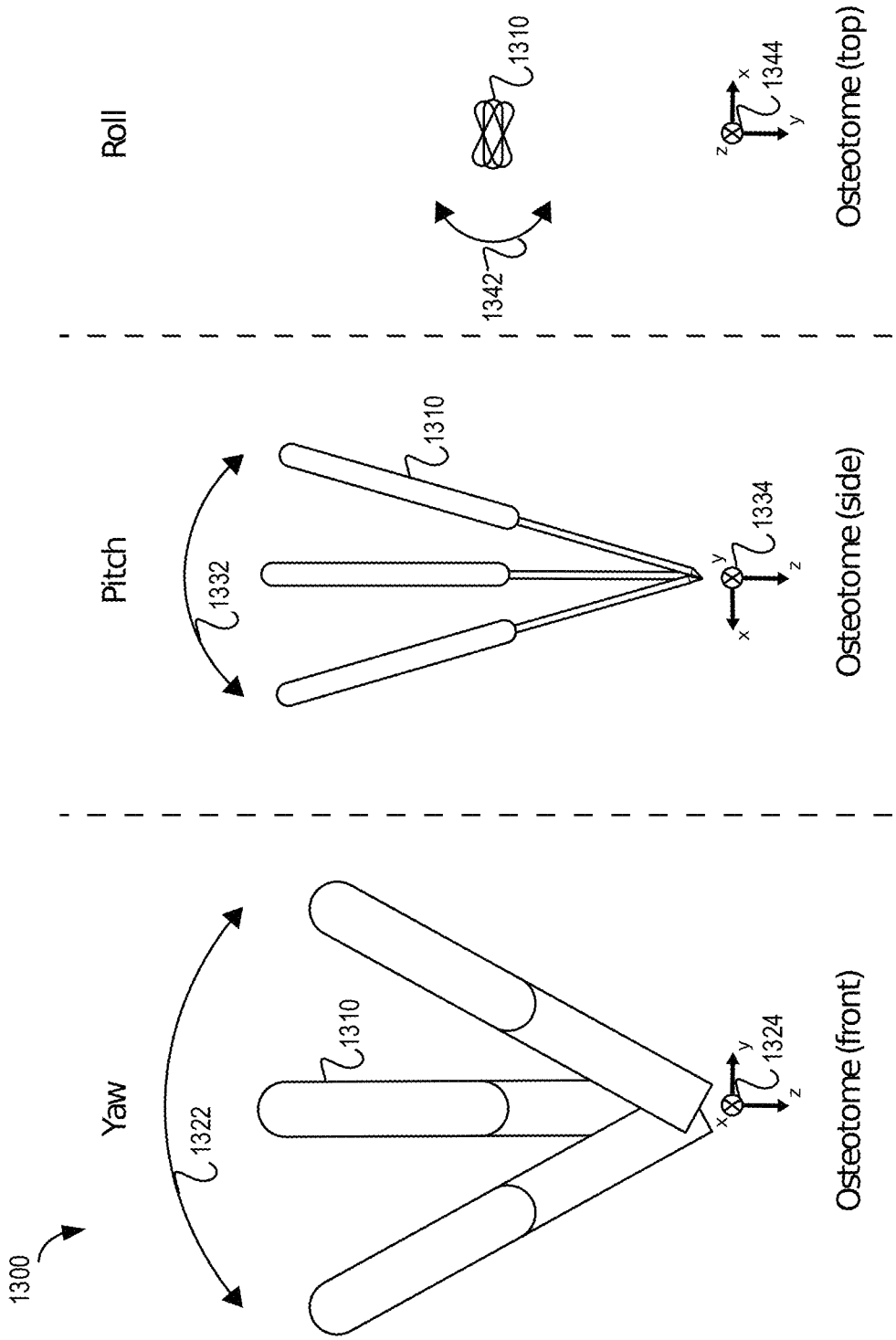
FIG. 13 shows an example of yaw, pitch, and roll pivots for an osteotome and planar tools.

Referring now to FIG. 13, shown therein is an example of yaw, pitch, and roll pivots 1300 for an osteotome and planar tools.

Given a set of planned cuts, a guided resection can relay feedback of the cutting tool poses to the active planned cut plane, where the cut plane is defined by a point and a normal. The metrics module 188 can determine the distance between the cutting tool's tip and the planned cut plane, the pitch, yaw, and roll angles, and whether the cutting tool is inside or outside the negative margin volume.

Pitch angle can be calculated through application of the dot product between the planned cut plane's normal and tool's z-axis, yaw angle can be calculated with the dot product of the plane normal with the tool's y-axis, and roll angle can be calculated with the dot product of the plane normal with the tool's x-axis. FIG. 13 shows an example of the yaw 1322, pitch 1332, and roll 1342 tilts on an osteotome 1310. The convention can apply to any planar tool, where the y-z plane defines the blade of the tool, with the z-axis being the pointing direction. Where the osteotome 1310 is seen from the front, the axes can be seen in a first orientation 1324. Where the osteotome 1310 is seen from the side, the axes can be seen in a second orientation 1334. Where the osteotome 1310 is seen from the top, the axes can be seen in a third orientation 1344.

The planned resection volume can be calculated by splitting the anatomical surface representation with each cutting plane in the set. This can enable comparison of the planned resection volume against the guided resection. The planned resection volume is, for example, the resulting model after splitting the anatomical surface representation in sequence across all the planned cutting planes. The guided resection volume is, for example, the resulting model after splitting in sequence with the performed cuts as recorded by the tracked instrument. The guided resection volume in this context can be in reference to the virtual model and surgical plan, where it may be compared quantitatively to the real resected specimen after registration with ex-vivo and post-operative imaging.

Methods described above can be combined to evaluate execution with respect to surgical plans and tasks. For example, line metrics can be used to evaluate how well a surgeon maneuvers in accordance with the planned trajectory, quantifying distance to planned trajectory as well as overshoot/undershoot of target, and jitter.

For geometric resections, evaluations can be made according to the performed cut relative to the planned cutting plane, including distance and angles (e.g., at entrance and deep points), overshoot/undershoot at target depth, and jitter.

Figure 14:
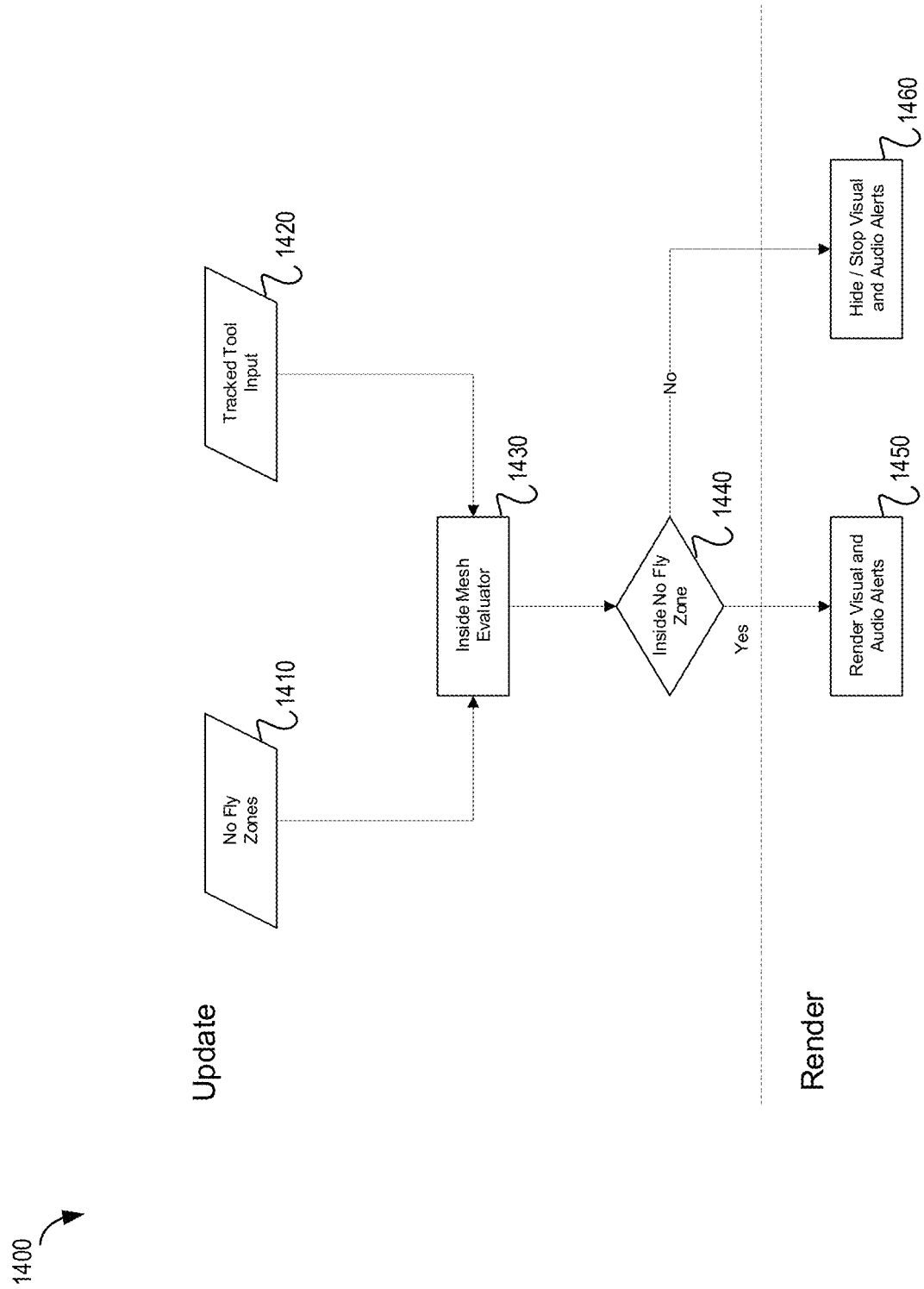
FIG. 14 shows a flow chart of an example embodiment of a method of managing critical structure avoidance in the AR system of FIG. 1A.

Referring now to FIG. 14, shown therein is a flow chart of an example embodiment of a method of managing critical structure avoidance 1400 in the AR system 100 of FIG. 1A.

Figure 33:
FIG. 33 shows an example visualization of a critical structure and no-fly zones in a skull model.

Critical structures in the surgical field may be highlighted to avoid damage/proximity. These can be based on prior imaging modalities where volume and surface representations have been segmented and are part of the model sets record 154. An example of contoured critical structures and 3 mm "no-fly zones" created from volume dilation 3300 is shown in FIG. 33, where the no-fly zones on the left indicate a critical structure to be avoided during a procedure. Tracked instruments that enter the no-fly zone can trigger visual and audio alerts. The system 100 may provide visualization of the critical structure and no-fly zones in a skull model. Segmentations include carotid (red), pituitary (blue), optic nerve (yellow), and orbit (purple). The surrounding dilation regions are the no-fly zones.

In at least one embodiment, the system 100 utilizes the server 110 and the database 150 to manage avoidance of critical structures. The server 110 obtains data models 152 that contain dilation regions around segmented critical structures. The server 110 identifies when tracked instruments are within the dilation regions (here, "no-fly zones"). The client device 170 alerts the user with audio/visual indicators when the tracked instruments go into the no-fly zones.

Critical structure avoidance may assist in AR intervention in situations where display devices look directly over the intervention field. Critical structures and no-fly zones may be hidden sub-surface. Critical structure avoidance can relay information such as whether a tool is clipping a tumor or a critical anatomy.

Direct in-field overlay for case-relevant data such as saw/drill settings for orthopedic cases or blood pressure and other vital data in microsurgical cases may be displayed on applications across client devices 170.

Combinations of surface/volume representations, plan, and patient images may be presented in a virtual window where the user may interact (e.g., scroll, rotate, zoom) with it throughout the procedure.

Case-specific notes and annotations planned by the surgeon or team pre-operatively may be pulled up with their spatial context and in reference to the surgical plan (e.g., to flag difficult portions of the surgery, avoidance/awareness of critical aberrant anatomy).

With spatial registration and tracking, the virtual surgical plan can be translated to a real-time environment where feedback is provided to the surgeon while performing the procedure, such as by providing visualizing metrics using the metrics module 188 from geometric resection, needle/tool placements (e.g., biopsies, targeted drug delivery, ablative procedures), and critical structure avoidance.

Additional data may be displayed in the field, such as case notes, annotations, and feeds from vitals. These may be anchored spatially to the reconstructed environment/tracked reference marker, or relative to the coordinate of the device.

Method 1400 can be divided into an update stage and a render stage, although method 1400 need not be so divided. At 1410, the application 172 selects no-fly zone data received from the server 110 and the plans record 156. At 1420, the application 172 receives tracked tool input data. At 1430, the application 172 executes an inside-mesh evaluator, using the no-fly zone data and tracked tool input data as data for evaluation if the tracked tool tip is inside the no-fly zone. At 1440, the method 1400 branches, depending on the result of 1430. If the inside-mesh evaluator determines that the tool is inside the no-fly zone, the method proceeds to 1450. If the inside-mesh evaluator determines that the tool is not inside the no-fly zone, the method proceeds to 1460. At 1450, the application 172 renders visual and/or audio alerts. At 1460, the application 172 hides or stops visual and/or audio alerts.

In method 1400, the processor of the client device 170 may use metrics to produce an AR visualization. The metrics are used to produce a heads-up display (HUD) display of an alert (e.g., if the tool trajectory intersects or the tool tip is within a no-fly zone, a warning message or window border flash is rendered). The AR visualization may be displayed on the primary client device 170, the replicate client device 170a, or both. The AR visualization may be produced by showing in-field alerts indicating placement or trajectory of the tracked instrument intersecting with the no-fly zone.

Geometric Resection

Figure 31:
FIG. 31 shows an example of playback of a navigated osteotomy on a femur.

For geometric resection of tumors, a plan is obtained from the plans records 156. The plan consists of a set of resection planes to be executed. A user can select the active cut plane to evaluate metrics against where the metrics are provided by the metrics module 188. The cutting tool can be quantitatively compared to the planned cut with respect to angle offsets (e.g., pitch and roll may be the most important) and distance between tip and plane. FIG. 31 illustrates a playback of navigated osteotomy (or "guided osteotomy") on the femur 3100. The visualizations include a set of planned cuts (blue outline), an active planned cut (green outline), a 5 mm negative margin (orange outline), and a tumor (red). The tumor, 5 mm negative margin, and surgical plan (set of cut planes) can be visualized on top of a physical model. The osteotome can be updated in real time with its position and orientation compared to the current cut in the plan. Real-time metrics from the metrics module 188 include distance and angles to the active planned cut.

In at least one embodiment, the system 100 utilizes the server 110 and the databases 150 to manage geometric resection. The server 110 obtains a surgical plan from the data model 152 that contains a set of cuts to be performed. The client device 170 enables visualization of the surgical plan over a physical model. The application 172 compares a tracked instrument to an active cut. The application 172 produces metrics based on the comparison, such as distance and angle to the cutting plane.

Figure 15:
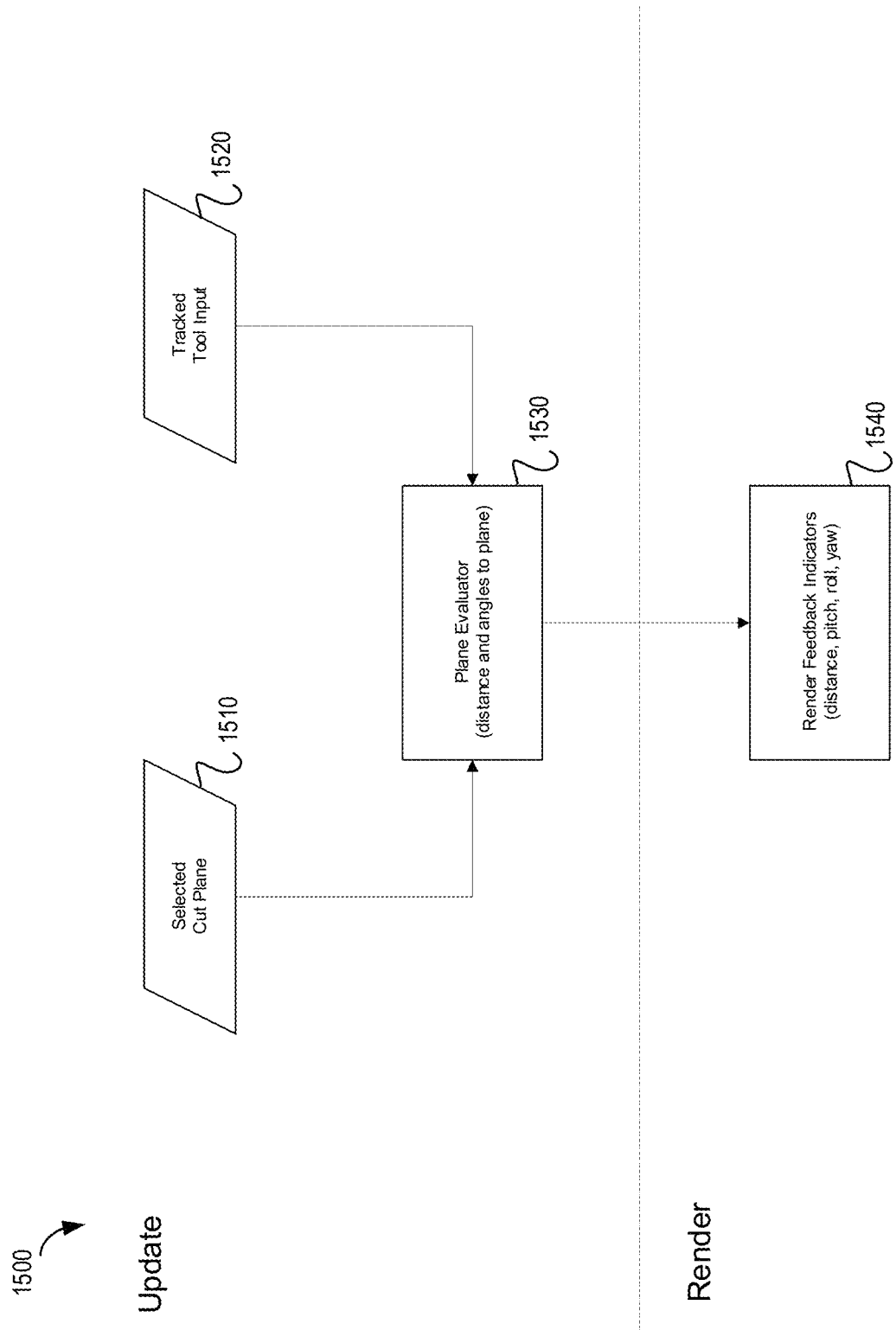
FIG. 15 shows a flow chart of an example embodiment of a method of managing geometric resection in the AR system of FIG. 1A.

Referring now to FIG. 15, shown therein is a flow chart of an example embodiment of a method of managing geometric resection 1500 in the AR system 100 of FIG. 1A. Method 1500 can be divided into an update stage and a render stage, although method 1500 need not be so divided. At 1510, the application 172 on a client device 170 selects a cut plane data received from the server 110 from the plans record 156. At 1520, the application 172 receives tracked tool input data. At 1530, the application 172 executes a plane evaluator, using the selected cut plane data and the tracked tool input data as data for evaluation. The evaluation can include distances and angles to the plane. At 1540, the application 172 renders feedback indicators, such as distance, pitch, roll, and yaw.

In method 1500, the processor of the client device 170 may use metrics to produce an AR visualization. The processor of the client device 170 may determine the pose of the tracked instruments, which updates its graphical representation. The intersection of the surface model and the plane of the tracked instrument may be used to select faces of the surface model that is on the intersecting plane, creating a subsection of the surface model corresponding to an outline. The AR visualization may be displayed on the primary client device 170, the replicate client device 170a, or both. The AR visualization may be produced by generating the trajectory of the tracked instrument, outlining an intersection of one of the plurality of active cut planes and the model set, and displaying a color-coded angle offset and a tip-to-plane distance to indicate precision. The precision may be tolerance or closeness to the intervention plan.

Needle Placements (Kyphoplasty, Biopsy, Ablation, Etc.)

For needle procedures, plan data from the plans records 156 may be selected where the plan data includes a set of line trajectories defined by an entrance point and target point. The metrics module 188 may then be used to generate metrics that include the distance of the needle or instrument tip to an active trajectory, the distance to a target, as well as the angle between needle and trajectory. For ablative procedures, the ablation volume can be considered in calculation of coverage with respect to segmented lesion volume from the model sets record 154. The ablation volume can be dynamically positioned with center aligned with the needle tip.

Figure 32:
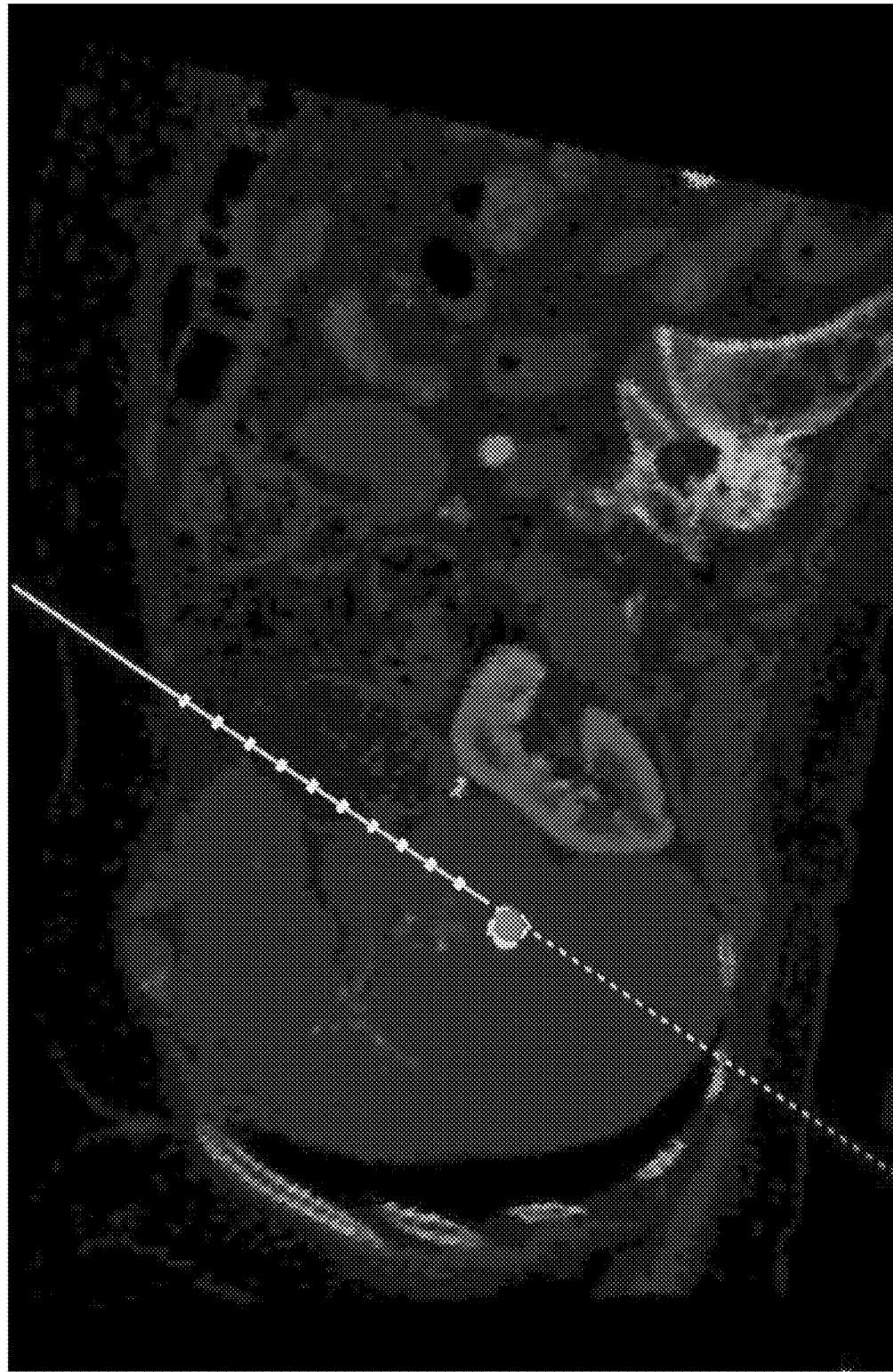
FIG. 32 shows an example of an ablative needle procedure.

An ablative needle procedure example 3200 is shown in FIG. 32. A surface representation of a liver lesion is shown in red. An oblique CT slice is in plane with the lesion—a green outline around the lesion demonstrates that the needle plane is aligned with the lesion.

In at least one embodiment, the system 100 utilizes the server 110 and the databases 150 to manage needle placement. The server 110 obtains a surgical plans record 156 that contains a set of needle trajectories (e.g., path, entry+target points). The client device 170 visualizes the trajectory over a physical model, using additional inputs (e.g., intersecting DICOM slice, ultrasound). The application 172 compares the tracked needle instrument to an active needle path. The application 172 uses the metrics module 188 to generate metrics, such as angle to planned path, distance to target, and distance to path. For ablation needles, the application 172 visualizes the ablation volume at the tip of the instrument, then calculates coverage (e.g., overlap between ablation volume and lesion volume).

Figure 16:
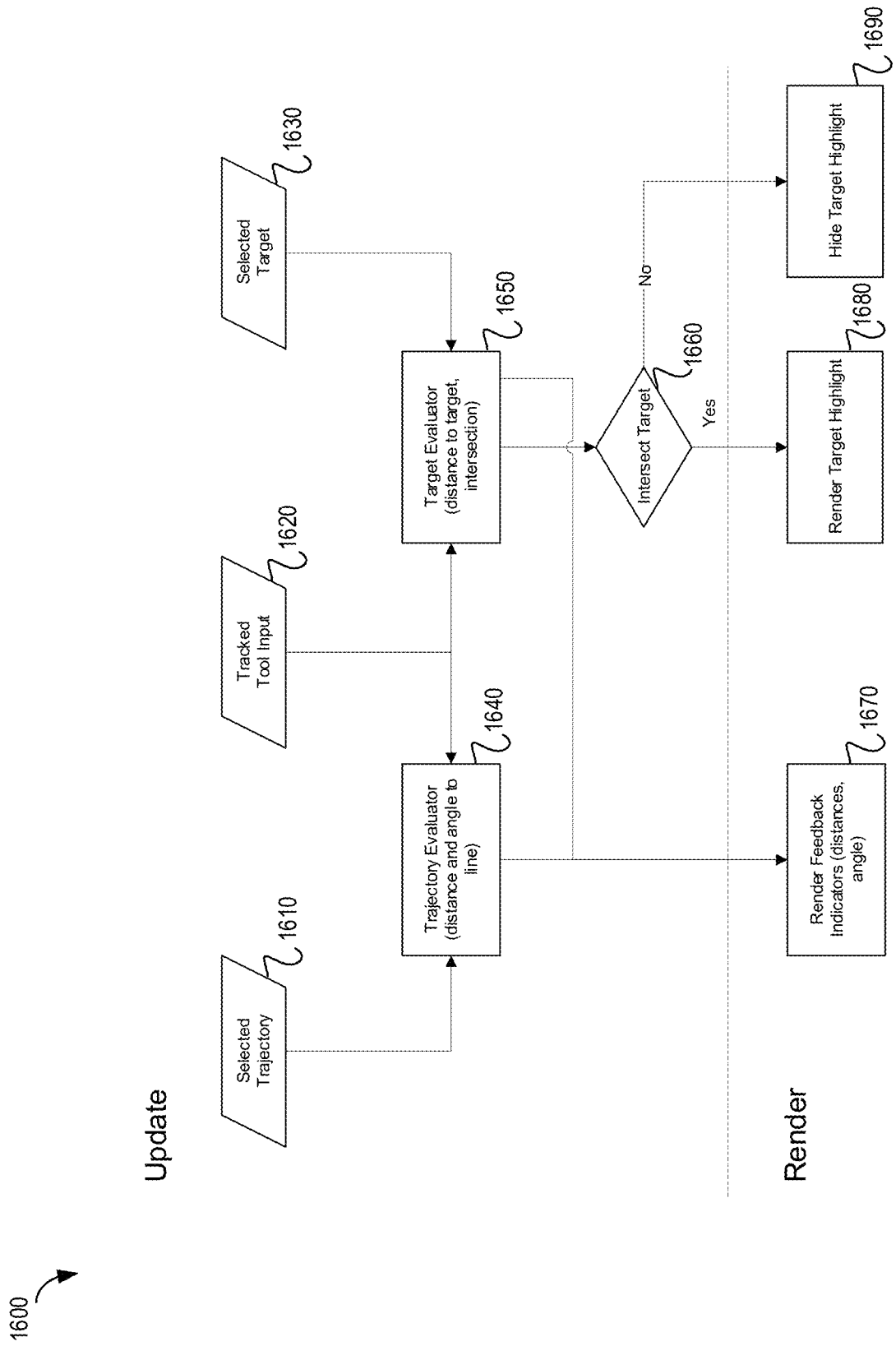
FIG. 16 shows a flow chart of an example embodiment of a method of guiding a needle in the AR system of FIG. 1A.

Referring now to FIG. 16, shown therein is a flow chart of an example embodiment of a method of guiding a needle 1600 in the AR system 100 of FIG. 1A. Method 1600 can be divided into an update stage and a render stage, although method 1600 need not be so divided. At 1610, the application 172 on client device 170 selects trajectory data from the plan received from the server 110. At 1620, the application 172 receives tracked tool input data. At 1630, the application 172 selects a target. At 1640, the application 172 executes a trajectory evaluator, using the selected trajectory and the tracked tool input as data for evaluation. The evaluation can include a distance and an angle to a line (or line segment) taken from the selected trajectory. At 1650, the application 172 executes a target evaluator, using the tracked tool input data and the selected target as data for evaluation. The evaluation can include a distance to the target or an intersection. At 1660, the method 1600 branches, depending on the result of 1650. If the target evaluator determines that the tool intersects with the target, the method proceeds to 1680. If the target evaluator determines that the tool does not intersect with the target, the method proceeds to 1690. At 1670, the application 172 renders feedback indicators, such as distances and angles. At 1680, the application 172 renders a target highlight. At 1690, the application 172 hides the target highlight.

In method 1600, the processor of the client device 170 may use metrics to produce an AR visualization. The processor of the client device 170 may determine the pose of the tracked instruments, which updates its graphical representation. The intersection of the surface model and the plane of the tracked instrument may be used to select faces of the surface model that is on the intersecting plane, creating a subsection of the surface model corresponding to an outline. The AR visualization may be displayed on the primary client device 170, the replicate client device 170a, or both. The AR visualization may be produced by generating a trajectory of the tracked instrument, generating an intersection of a trajectory of the tracked instrument with the target point, generating a line between a tip of the tracked instrument and a planned line trajectory, and displaying a color-coded tip-to-trajectory distance, a tip-to-target distance, and an instrument-to-trajectory angle to indicate precision.

Passive, Visual Walkthroughs

Figure 17:
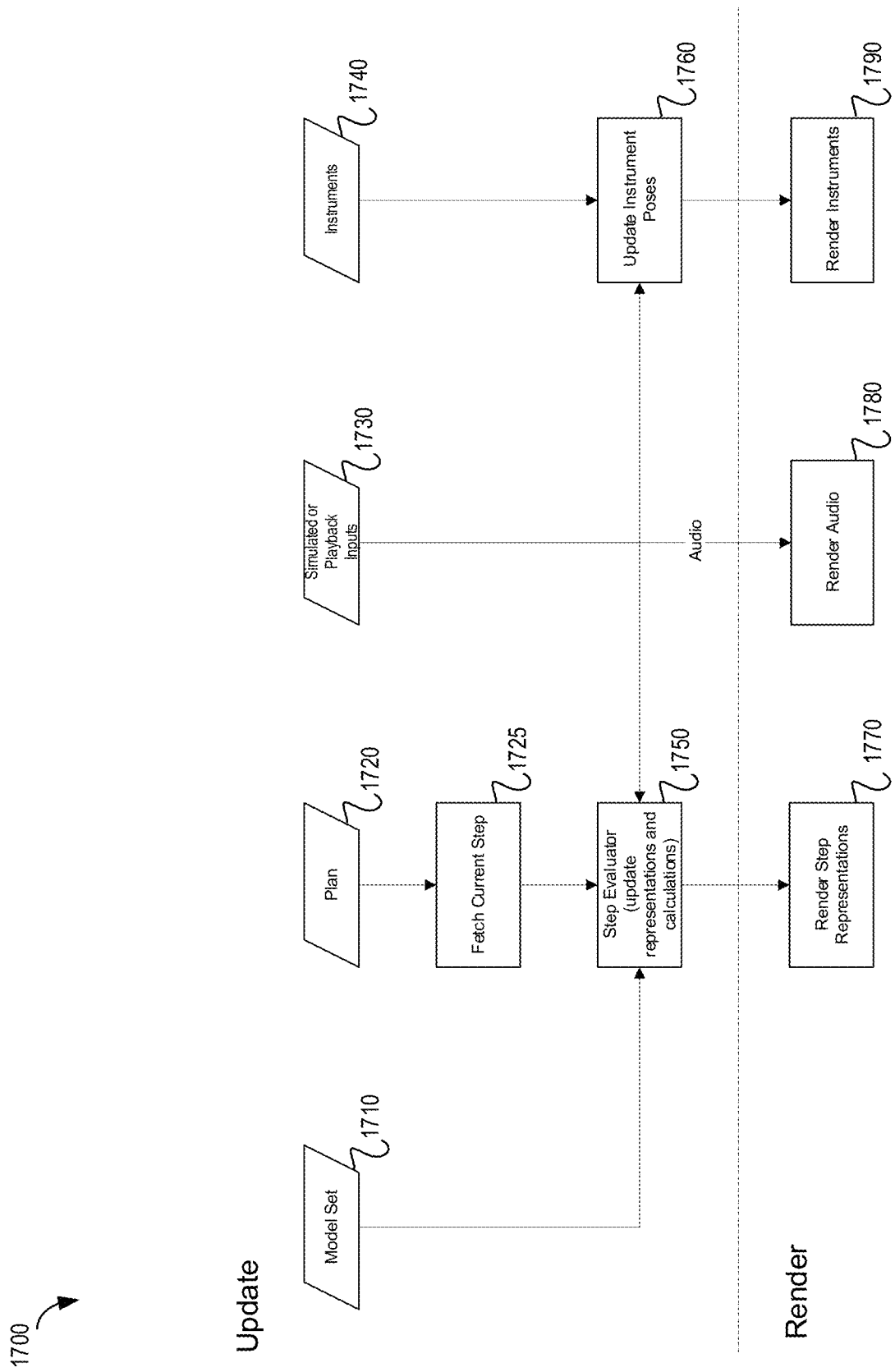
FIG. 17 shows a flow chart of an example embodiment of a method of managing a procedure walkthrough in the AR system of FIG. 1A.

Referring now to FIG. 17, shown therein is a flow chart of an example embodiment of a method of managing a procedure walkthrough 1700 in the AR system 100 of FIG. 1A.

A surgeon can utilize an AR device (e.g., headset, smartphone) to visualize a standard (e.g., surgical) procedure before performing it to prepare and gain familiarity. The demonstration may also include 3D manipulation and physical models, which are defined as follows:

3D manipulation: the user can interact with the model sets record 154, including altering the perspective or view angle, or adding/removing layers of surface and volume representations to help with visualization; and Physical models: the demonstration may integrate physical model fusion whereby there exists AR overlays on physical models, and the surgeon can physically perform aspects of the procedure while gaining the extra insight provided by the holographic or otherwise augmented overlays.

In at least one embodiment, the system 100 utilizes the server 110 and the database 150 to coordinate passive, visual walkthroughs. Data models 152 (e.g., anatomical segmentation, surgical plan) are generated in post-processing at an institution after image acquisition. The data models are sent to one or more connected client devices 170 by the server 110. A client device camera is used to localize a flat surface on which to place virtual content. For physical model fusion, the data model 152 (e.g., virtual) is aligned through a marker tracked by the camera. A user may select through and view different steps of the procedure—if there is playback data, the instrument representations are updated during playback along with audio if available.

Surgical Procedure Walkthroughs

Moderated walkthroughs combined with traditional education media can be used to enhance education of early-stage learners. These include visualization of a data model from a model sets record 154 fused or embedded to physical teaching models or textbook illustrations. Annotations and comments can be made by the individual learner or classmates, where annotations may be textual notes, audio, or video demonstrating or summarizing the sequence and steps of the procedure.

Method 1700 can be divided into an update stage and a render stage, although method 1700 need not be so divided. At 1710, the application 172 on client device 170 selects model set data from the model sets records 154 and receives the model set data from the server 110. At 1720, the application 172 selects plan data received from the server 110 and the plans record 156. At 1725, the application 172 fetches the current step from the plan data. At 1730, the application 172 receives simulated or playback input data. At 1740, the application 172 selects instrument data received from the server 110 and the instruments records 160. At 1750, the application 172 executes a step evaluator, using the model set data, the current step, and an instrument pose as data for evaluation. The output from the step evaluator may include updated step representations and calculations. At 1760, the application 172 updates instrument poses based on the instrument inputs, which may be fed back to the step evaluator. At 1770, the application 172 renders step representations based on the output from the step evaluator. At 1780, the application 172 renders audio based on the simulated or playback inputs. At 1790, the application 172 renders the instruments, based on the updated instrument poses.

In at least one embodiment, the client device 170, having a processor, can carry out a method for performing AR-assisted surgical procedure walkthrough, the method comprising: receiving a virtual surgical plan at the client device; receiving a virtual model at the client device; embedding the virtual model to a physical object using the processor; receiving tool manipulation data from user input at the client device; modifying a view of the virtual model in relation to the physical object using the processor based on the tool manipulation data; determining metrics by using the processor to apply spatial registration and track the tool used in execution of the virtual surgical plan; and providing feedback at the client device based on the metrics.

Anatomic Visualization

Figure 34:
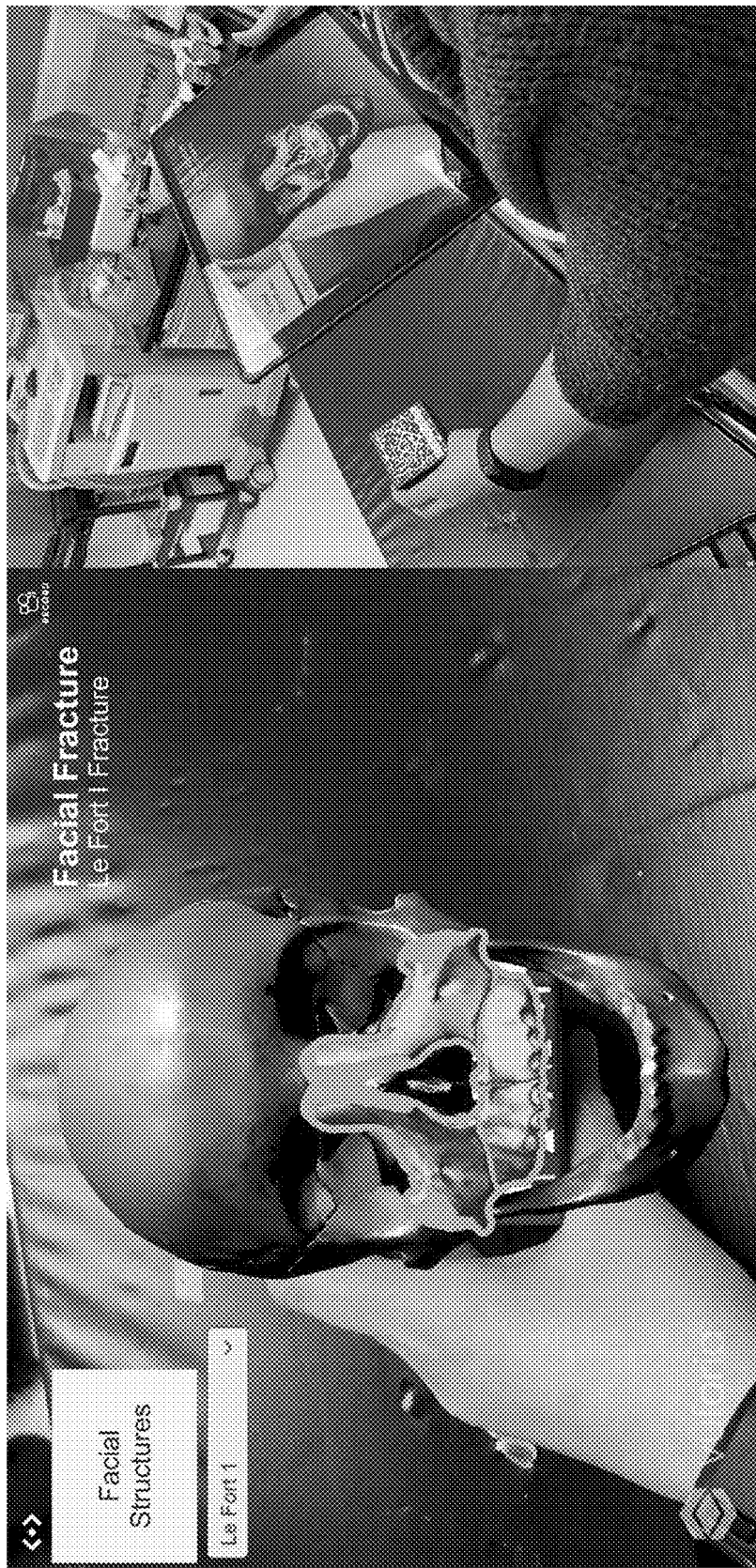
FIG. 34 shows an example virtual skull model mapped to a physical object.

Reference data models from the model set records 152 may be used in isolation or fused with physical models to present an anatomy in 3D. Users may interact with the data through 3D manipulation or view AR visualizations of simulated real-world actions across procedures (e.g., osteotomy, radiofrequency ablation) over the virtual or physical models. FIG. 34 demonstrates a visualization of a virtual skull mapped to a physical object, with selectable fracture patterns 3400. A user may interact with the physical object and the model to display fracture patterns and highlight different parts of the skull.

In at least one embodiment, the system 100 utilizes the server 110 and the database 150 to manage anatomic visualization. The server 110 sends reference data models selected from the data model records 152 to client devices 170 to be used for visualization and teaching.

Augmenting Scientific Output with FAIR Principles

When the data models records 152 are stored in a human and machine consumable way with persistent universally unique identifiers, they may be cross-referenced by traditional scientific output and serve as a new medium of communication, providing spatial context and dynamic content to papers and conference proceedings.

Figure 35:
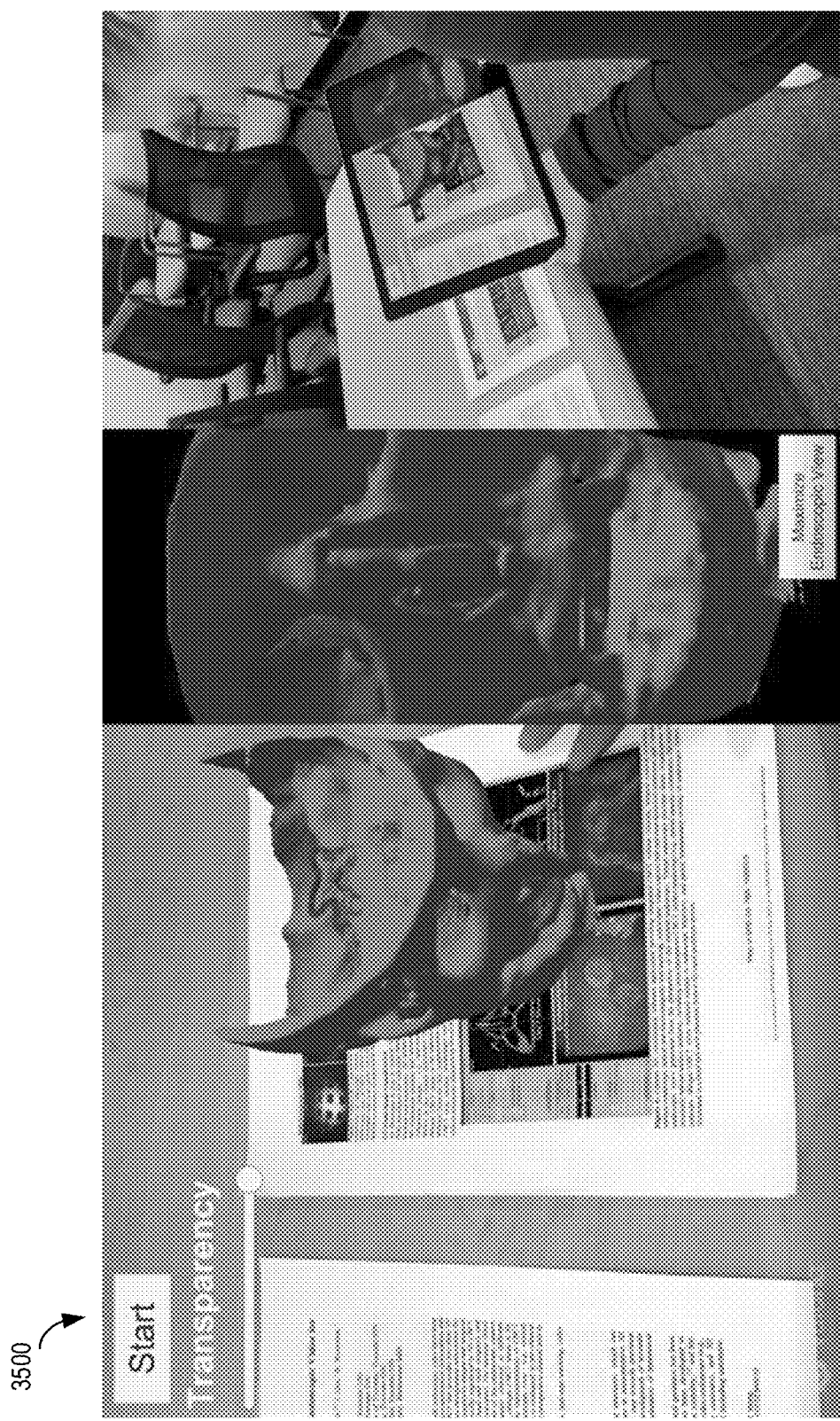
FIG. 35 shows an example of an AR-enhanced paper.

For example, see FIG. 35, which illustrates a surface representation of a Cone Beam Computed Tomography (CBCT) model from a previously published paper 3500. The model is anchored to the figure (in the published paper), which acts as a reference plane where known spatial points are matched to image points to calculate the pose via homography.

In at least one embodiment, the system 100 utilizes the server 110 and the database 150 to augment scientific output with FAIR principles. The server 110 obtains figures (e.g., from a scientific paper) to use as AR markers for overlay. The client device 170 visualizes virtual models or playback relevant to the figures, and the application 172 spatially anchors the virtual models or playback to the figures.

Figure 18:
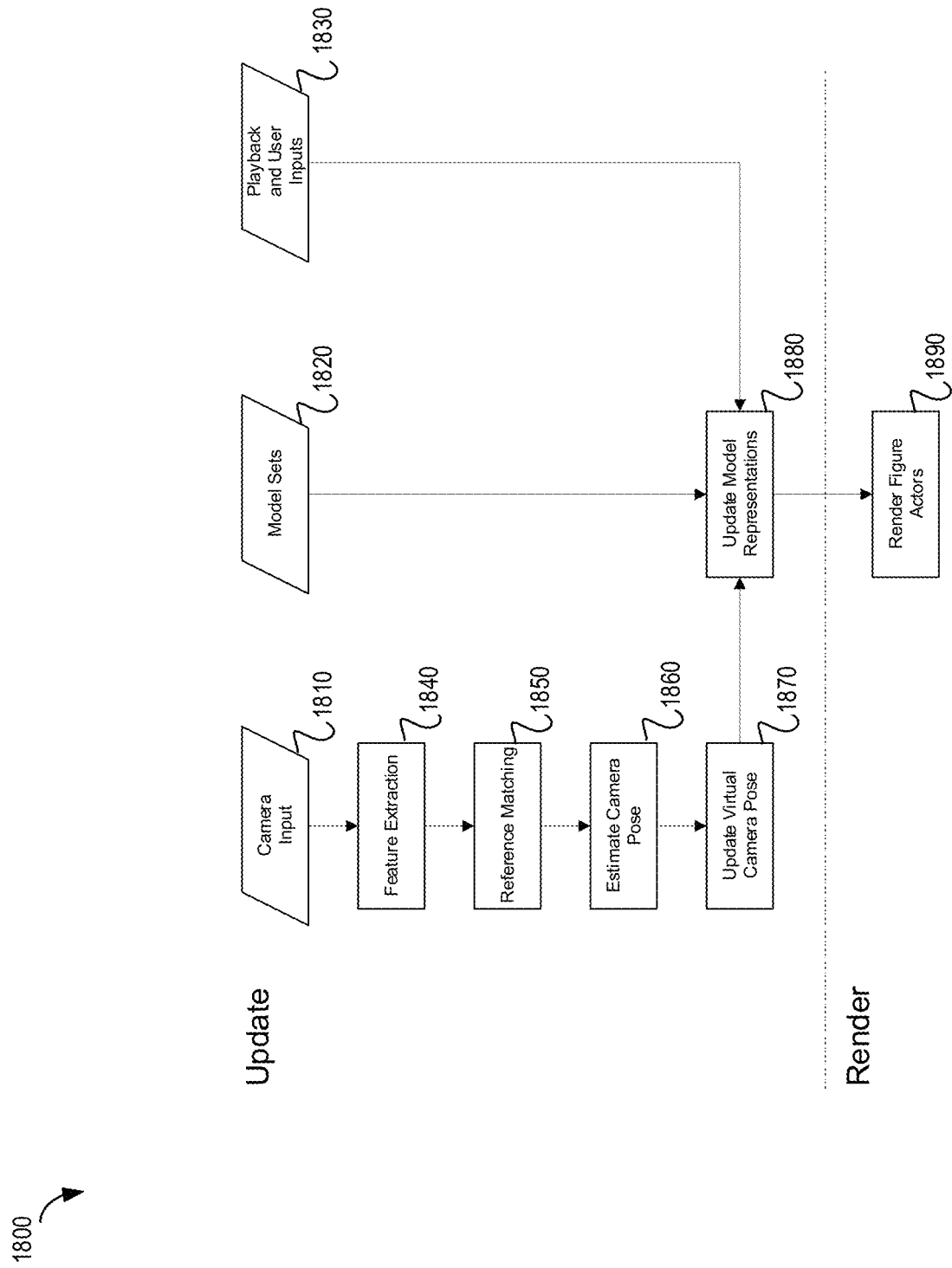
FIG. 18 shows a flow chart of an example embodiment of a method of tracking a figure and enhancing a publication in the AR system of FIG. 1A.

Referring now to FIG. 18, shown therein is a flow chart of an example embodiment of a method of tracking a figure and enhancing a publication 1800 in the AR system 100 of FIG. 1A. Method 1800 can be divided into an update stage and a render stage, although method 1800 need not be so divided. At 1810, the client device 170 receives camera input data. At 1820, the application 172 selects model data that is received from the server 110 and the model sets records 154. At 1830, the client device 170 receives playback and user input data. At 1840, the application 172 extracts features from the camera input data. At 1850, the application 172 matches features to references of known spatial objects based on the extracted features. At 1860, the application 172 estimates the camera pose based on matched references of known spatial objects. At 1870, the application 172 updates virtual camera pose data to align the virtual camera to the real camera of the client device 170. At 1880, the application 172 updates model representations based on the updated virtual camera pose data, the model set data, and the playback and user input data. At 1890, the application 172 renders figure actors based on the updated model representations.

In at least one embodiment, the client device 170, having a processor, can carry out a method for performing AR-assisted scientific output augmentation, the method comprising: receiving a surface representation of a Cone Beam Computed Tomography (CBCT) model and a corresponding figure from a journal article at the client device; anchoring the CBCT model to the figure image using the processor; calculating a pose using the processor by matching known spatial points of the figure image to image points of the CBCT model via homography; and displaying the pose on a display.

Skills Translation and Evaluation

The metrics module 188 may be used to score performance in a competency-based skills program. Data models 152 can be developed and stored to teach specific procedures, with recording of performances for review and feedback. Spatial overlay and practice under guidance with physical models can help teach best practices and skills.

Holographic or otherwise augmented visualizations of maneuvers and tasks may provide spatial guidance for the individual to perform. Plans from the plans records 156 for procedures may also be used to score performances under tool tracking, either virtually or in combination with a physical model. One example is shadowing a sequence of steps through suturing where hand and instrument positions are visualized. For needle or geometric resection procedures, evaluation of execution with respect to the plan includes time, distance, and angles (average and variance) to the planned trajectory or cut plane, undershoot/overshoot at target or depth, and jitter.

In at least one embodiment, the system 100 utilizes the server 110 and the database 150 to manage skills translation and evaluation. The server 110 provides a client device 170 with a session 164 on which individuals may practice procedures in a guided way (e.g., plan and execution visualized/played back). The client device 170 evaluates the individuals on how well they perform tasks. The application 172 produces and stores metrics that are generated by metrics module 188 using data from tracked instruments and/or tracked hands (i.e., the user's tracked hand movements) for score assessment. The application 172 displays the metrics so that the individuals can compare their own statistics across attempts as well as against the population.

Self-Assessment for Performance Enhancement

Tracked tools, maneuvers, and tasks performed by an individual may be evaluated against averages across different skill groups and individual performance statistics.

Learners can flag or comment across steps in performance to convey their thought process and reasoning for review later by a mentor or teacher.

Formal Assessments in a Standardized Environment

Common data models 152 may be used for formal assessments in a standardized environment with one or more learners in series or parallel. The teacher or reviewer may define objective measurements for assessment or feedback of the procedure (e.g., in place of standardized patients of clinical scenario questions).

Figure 19:
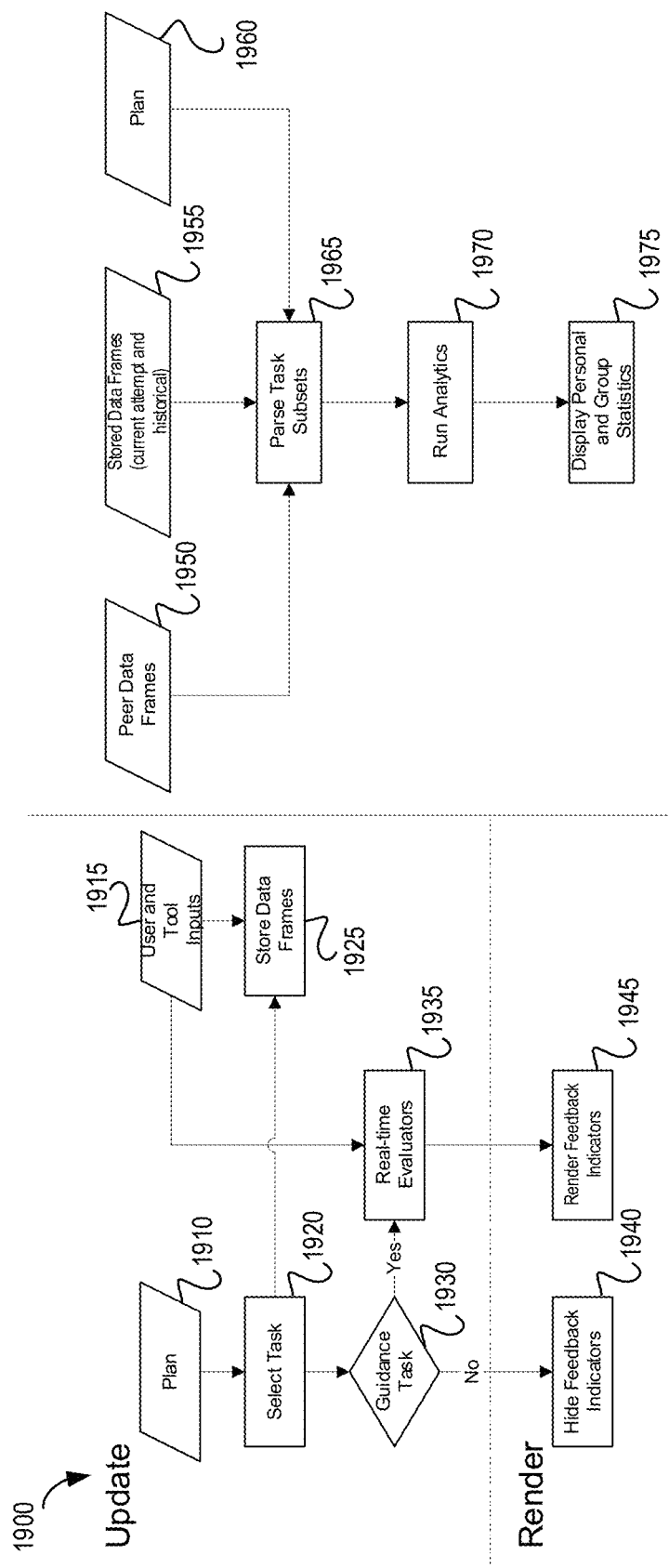
FIG. 19 shows a flow chart of an example embodiment of a method of managing an assessment and review in the AR system of FIG. 1A.

Referring now to FIG. 19, shown therein is a flow chart of an example embodiment of a method of managing an assessment and review 1900 in the AR system 100 of FIG. 1A. Method 1900 can be divided into an update stage and a render stage, although method 1900 need not be so divided. At 1910, the user selects a plan using the client device 170, and the selected plan is sent to the server 110. The server 110 then obtains the selected plan data from the plans record 156 and sends it to the client device 170. At 1915, the application 172 receives user and tool input data. The user data can be data about how the user is interacting with the device 170, and the tool data can be data about how the tool is moved by the user. At 1920, the application 172 receives a task selection from the user via the client device 170 identifying what task the user will perform. At 1925, the client device 170 and/or server 110 stores data frames based on the selected task and inputs from the user and tools that perform the task. For example, the inputs can be collected data for the user executing a first cut with a tool (e.g., a saw) in a plan. At 1930, the method 1900 branches, depending on the result of 1920. If the selected task is flagged as requiring guidance, the method 1900 proceeds to 1935. If the selected task is not flagged as requiring guidance, the method 1900 proceeds to 1940. At 1935, the application 172 provides real-time evaluators based on the selected task and the user and tool input data. At 1940, the application 172 hides feedback indicators, which may be done so that the user is not distracted with the feedback indicators such as when the user is performing a movement with a tool, for example. At 1945, the application 172 renders feedback indicators to show the user how they have performed; this may be done when the user is finished moving the tool. At this point, method 1900 may end if no review is selected. However, if review is selected, method 1900 continues at 1950. At 1950, the client device 170 receives peer data frames (e.g., recorded data from peers executing the task) from the server 110. At 1955, the application 172 aggregates the stored data frames (e.g., the recorded device data, such as tracked hands or instruments, from task execution), such as the current attempt and historical attempts. At 1960, the application 172 receives the plan data from the plans record 156 from the server via HTTP request and WebSocket and then selects the plan data used for analysis. At 1965, the application 172 parses task subsets based on one or more of the peer data frame data, the stored data frame data, and the plan data. The application 172 may do the parsing using metadata from the plan. For example, a biopsy plan may have many trajectories, where each trajectory is a task. Also for example, a geometric resection plan may contain many cutting planes, where each cut plane is a task. At 1970, the application 172 runs analytics on the parsed task subsets to obtain personal statistics. The application 172 can compute the personal statistics, for example, from stored data obtained at 1915 and/or 1925. At 1975, the application 172 displays personal and/or group statistics. The application 172 can compute the group statistics from peer data, where each peer runs its own instance and has data stored as at 1915 and 1925.

Walkthroughs (e.g., Multidisciplinary Difficult Case Rounds)

In another aspect, multiple users may join a session 164 that has been setup by the server 100 to collaboratively walk through a simulation of a difficult case to gain shared insight and share perspective on a proposed procedure/surgery. Annotations and case notes may be stored to assist in planning or in context of the surgical plan and tasks. Collaborative walk-throughs may include physical model fusion and 3D manipulation where interaction with a model data from the model sets records 154 and changes in visualization are updated and shared across users.

Accordingly, in at least one embodiment, the system 100 utilizes the server 110, database 150, and client devices 170 to coordinate walkthroughs. The server 110 receives requests from multiple users via their client devices 170 to join a session. The server 110 joins two or more of the users via their client devices 170 to the session. The server 110 assigns one of the client devices 170 as the primary client device 170, and the rest of the client devices 170 are denoted as replicate client devices 170a. The primary client device 170 dictates the data flow and controls viewing options, similar to a presenter in a remote presentation application. The server 110 causes display changes and options to be broadcast from the primary client device 170 to the replicate client devices 170a in the session. The server 110 may route audio (e.g., on a separate data stream or in packets along with the video) to enable two-way audio. The system 100 may be distributed such that physical models require each institution or remote user to have the model used for virtual/real fusion, which can be fabricated through 3D printing at each institution.

In at least one embodiment, the system 100 utilizes the server 110 and database 150 to coordinate a surgical procedure walkthrough for educational purposes. The server 110 obtains reference (or standardized) data sets and additional annotation media from the database 150.

Telementoring

In another aspect, in at least one embodiment, the system 100 may provide telementoring capabilities so a remotely located surgeon may be guided by an expert or team from a hospital from across the world. The server 110 may be hosted in the cloud or at the institution accessible remotely through a virtual private network (VPN), enabling authenticated users to join a session 164 locally and remotely.

Examples include oncology procedures where video streams are shared across users in a session 164. The remote expert may contour over video where the resection margin should be to provide real-time guidance. The contour may be presented over video, or ray-casted to select elements of the underlying surface representations if virtual models are present. Physical models or reference markers may also be fabricated and registered with client devices 170 across different locations. Tools may then be positioned by one user in reference to virtual/physical models and displayed virtually to others. The user may then shadow the sequence and steps spatially as indicated by the expert.

Accordingly, in at least one embodiment, the system 100 utilizes the server 110, database 150, and client devices 170 to coordinate telementoring. Each client device 170 connects to the server 110 through WebSocket. The server 110 broadcasts device data between users at the different client devices 170 over WebSockets (e.g., audio, video, tracked instruments, gestures). The server 110 causes the expert user's input from a remote device to be broadcast to a remote user. The server 110 enables input from the remote user device to be streamed to the expert user for feedback. In an example sequence of events, the server 110 enables: (a) video to be broadcast from the client device of the novice user to the client device of the expert user; (b) the expert user can use their client device and application 172 to trace over the model and over the video generated by the novice user; and (c) the expert-modified video can then be sent from the client device of the expert user to the server 110 which can then broadcast the expert-modified video back to the client device of the novice user.

Individualized Difficult Case Practice/Pre-Execution

Physical models may be fabricated (e.g., one or a combination of 3D printing and molding of rigid or flexible materials) from surface or volume representations generated from patient images to practice difficult approaches and dissections.

Physical models may be fused with holographic or otherwise augmented visualizations. Virtual models and visualizations may include: (1) surface and volume representations from model data from a model sets record 154 and plan data from a plans record 156; (2) interactivity and comparison of the model set data and the plan data in reference to anatomical norms (e.g., facial proportions, measurements, cephalometric data, etc.); and (3) reference to a normal data set for age/gender matched normals.

Accordingly, in at least one embodiment, the system 100 utilizes the server 110, the database 150, and the client device 170 to coordinate individualized difficult case practice. The database 150 comprises data models 152 that include a reference set for age/gender matched normals. The client device 170 produces a visualization of the individual against the reference normal set. To produce the visualization, for example, two model sets can be registered (e.g., via facial or anatomical features) and overlaid; spatial deviations can be heat mapped to denote areas that differ and degree of magnitude. A clinician may then use the application 172 on their client device 170 to measure over the visualization of the individual and reference sets to measure and analyze differences and send data on these differences to the server 110. The server 110 may then store these differences and/or produce a report thereon.

Figure 20:
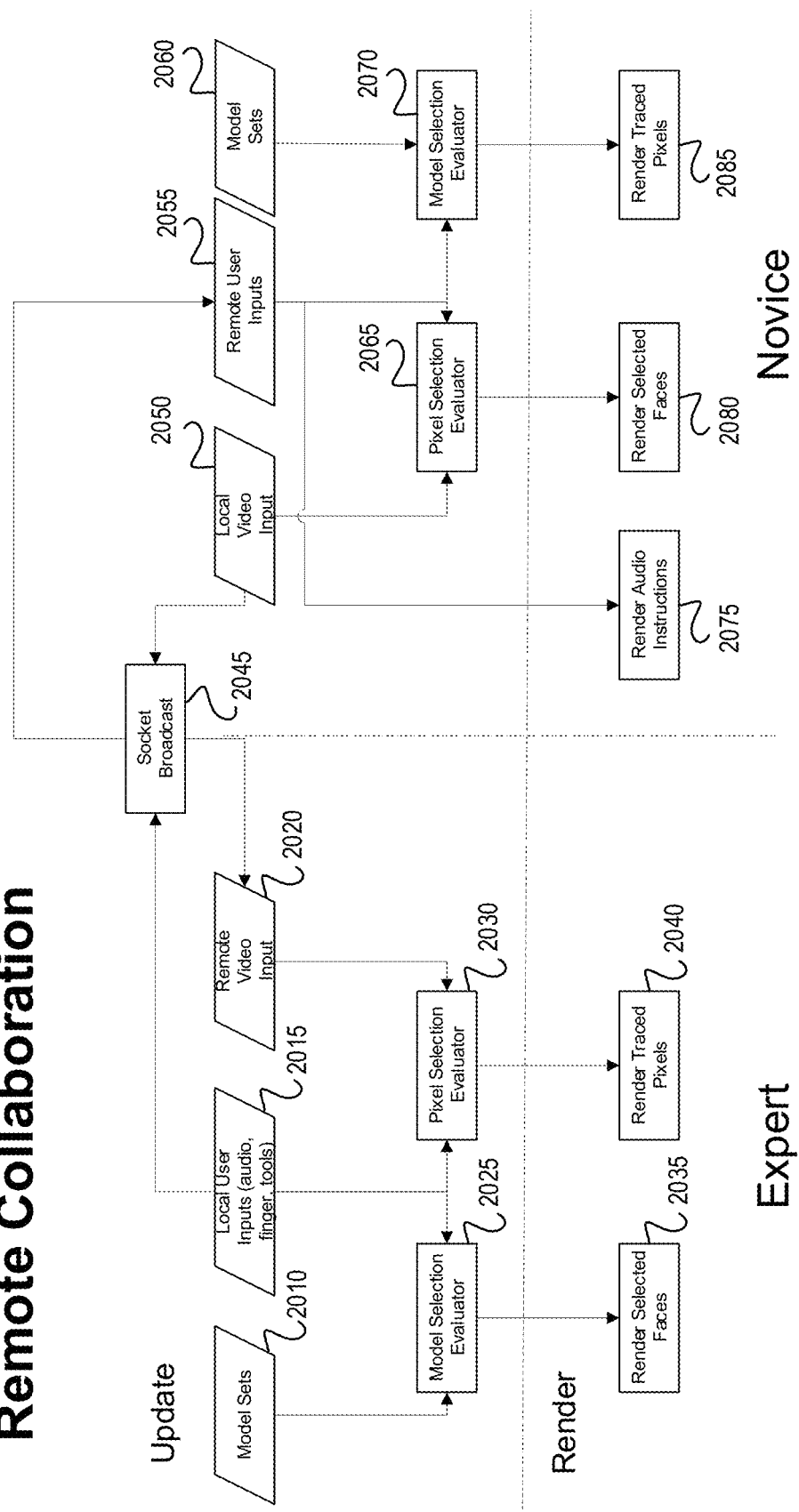
FIG. 20 shows a flow chart of an example embodiment of a method of managing remote collaboration in the AR system of FIG. 1A.

Referring now to FIG. 20, shown therein is a flow chart of an example embodiment of a method of managing remote collaboration 2000 in the AR system 100 of FIG. 1A. Method 2000 provides steps (which may or may not occur in an order, and some of which may be processed concurrently) that may be carried out in whole or in part to manage walkthroughs, telementoring, individualized difficult case practice, or other forms of remote collaboration. Method 2000 can be divided into an update stage and a render stage, although method 2000 need not be so divided.

At 2010, the client device 170 receives model set data from the model sets record 154 in the database 150. The session creator can specify which model set data is to be received by the client device 170. At 2015, the client device 170 receives local user input data, such as audio data, finger gesture data, and tool data. At 2020, the client device 170 processes remote video input data received from the server 110. The server 110 can obtain details on what data to select and which client device 170 to send the data to from a WebSocket message (e.g., which is broadcast through a WebSocket connection). At 2025, the application 170 executes a model selection evaluator based on the model set data and the local user input data. At 2030, the application 170 executes a pixel selection evaluator based on the local user input data and the remote video input data. At 2035, the application 170 renders selected faces based on the output from the model selection evaluator. At 2040, the application 170 renders traced pixels based on the output from the pixel selection evaluator. An "expert" may be designated to provide the input data sent to the system 100 or to receive the outputs provided by the system 100 at 2010 to 2040. A "novice" may be designated to provide the input data sent to the system 100 or to receive the outputs provided by the system 100 at 2050 to 2085. At 2045, the server 110 manages a socket broadcast. The socket can broadcast local user input data (e.g., from an expert) and local video input data (e.g., from a novice) to generate remote video input data (e.g., to send to the client device of the expert) and remote user input data (e.g., to send to the client device of the novice). At 2050, the client device 170 receives local video input data (e.g., video from a camera connected locally to the client device 170). At 2055, the client device 170 processes remote user input data. The client device 170 may process the remote user input data, for example, by determining the location of interaction by a user on a render window, ray-casting the location from the render window out to determine if part of a model is hit (and if so, which face or vertices). Here, remote and local users can be at two different geo-locations; they may have their own client devices, where each person interacts with a render window and underlying model independently. At 2060, the client device 170 receives the model set data from the model sets record 154. At 2065, the application 172 executes a pixel selection evaluator based on the local video input data and the remote user input data. At 2070, the application 172 executes a model selection evaluator based on the remote user input data and the model set data from the model sets record 154 to select vertices or faces of the models in the model set. When selecting parts of the model, a location on the render window (e.g., where user input comes from a mouse or touch) can be projected out to determine a part of model is hit to select the underlying face or vertices. At 2075, the client device 170 renders audio instructions based on the remote user input data. For example, the instructions include how the user should perform a task based on what is happening in the video, how to proceed, what to avoid, etc. At 2080, the application 172 renders selected faces based on the output from the pixel selection based on the pixel selection evaluator. At 2085, the application 172 renders traced pixels based on the output from the model selection evaluator.

In at least one embodiment, the client devices 170 and the server 110 can carry out a modified version of method 2000 for managing multi-user AR collaboration. The method begins with the replicate client device 170*a* receiving model sets and an intervention plan from the server 110. The model sets and the intervention plan can provide visualization and remote guidance. The server 110 receives local user inputs from the replicate client device 170*a* providing remote instructions. The remote instructions may be from expert to novice and include how to best perform an intervention; the remote instructions may be, for example, audio or spatial annotations. The replicate client device 170*a* sends the local user inputs through the server 110 to the primary client device 170. The local user inputs can provide visual annotation and guidance remotely (e.g., from an expert to a novice). The replicate client device 170*a* displays remote video input in combination with the model sets and the intervention plan, the model sets including an underlying surface model. The remote video input may be obtained from a replicate client device 170*a*. The remote video may be spatially registered to the intervention field and data models so the novice can perform the intervention with AR guidance and overlay. For example, the person performing the intervention may have their display device with camera over the surgical field-of-view. The remote video input, when fused with the model sets and the intervention plan, provide an AR perspective of the novice and how they are currently performing the intervention. The underlying surface model may be, for example, an underlying graphic model of patient anatomy or disease. The replicate client device 170*a* executes a pixel selection evaluator based on the local user inputs and the remote video input, thereby generating a first pixel selection output. The pixel selection evaluator maps a pixel location in a render window to a 3D location of the underlying surface model. The replicate client device 170*a* executes a model selection evaluator based on the model sets and the first pixel selection output to map a pixel location in a render window to a 3D location of an underlying surface model, thereby generating a first model selection output. The replicate client device 170*a* renders first selected faces of the underlying surface model based on the first model selection output. The face may be a graphic primitive of a surface mesh, which may be a set of edges (which can be a set of vertices). Selecting a face may then also include selecting the corresponding edges and vertices. A selection of faces may be a subsection of the surface mesh. The replicate client device 170*a* renders first traced pixels based on the first pixel selection output. Traced pixels may be obtained when the render window location is captured by an input interface such as a capacitive touch or mouse. The display location may be used to determine the corresponding pixel location of the video in the render window. The first trace pixels relate to the render window (or display) of the primary client device 170.

In at least one embodiment, the client devices 170 and the server 110 can carry out a modified version of method 2000 for managing multi-user AR collaboration at the primary client device 170 performing the AR intervention. The method begins with the primary client device 170 receiving model sets and an intervention plan from the server 110. The primary client device 170 processes remote user inputs. The remote user inputs may be, for example, remote instructions from an expert user on the replicate client device 170a. The primary client device 170 receives local video input. The local video input may be video of the intervention field in which virtual content is overlaid to provide the AR experience (e.g., video from a camera on the display device or via an endoscope). The local video input may be, for example, AR video input that allows for real-virtual fusion; this provides a spatial perspective of the primary client device 170, which is used to perform the intervention. The primary client device 170 executes a pixel selection evaluator based on the remote user inputs and the local video input, thereby generating a second pixel selection output. The primary client device 170 executes a model selection evaluator based on the model sets and the remote user inputs, thereby generating a second model selection output. The primary client device 170 renders audio instructions based on the remote user inputs. The audio instructions may provide, for example, vocal instructions to novices/learners. The remote user inputs may be, for example, spatial annotations or audio to help the local user of the primary client device 170. The primary client device 170 renders second selected faces based on the second pixel selection output. The primary client device 170 renders second traced pixels based on the second model selection output. The renderings by the primary client device 170 may allow, for example, the primary client device 170 to draw the attention of the user of the primary client device 170 to something in particular (e.g., what to do with an instrument or tool).

In at least one embodiment, the client device 170 performs one or more of the AR methods described herein (such as, but not limited to, method related to planning, intervention, guidance, education for medical applications). The client device 170 includes a display for displaying AR images. The client device 170 includes a user interface (which may be a combination of hardware and/or software) for receiving user input. The client device 170 includes a memory for storing program instructions for performing the one or more methods. The client device 170 includes a processor that is operatively coupled to the display, the user interface, and the memory, wherein the processor is configured to execute the program instructions for performing the one or more methods.

Figure 21:
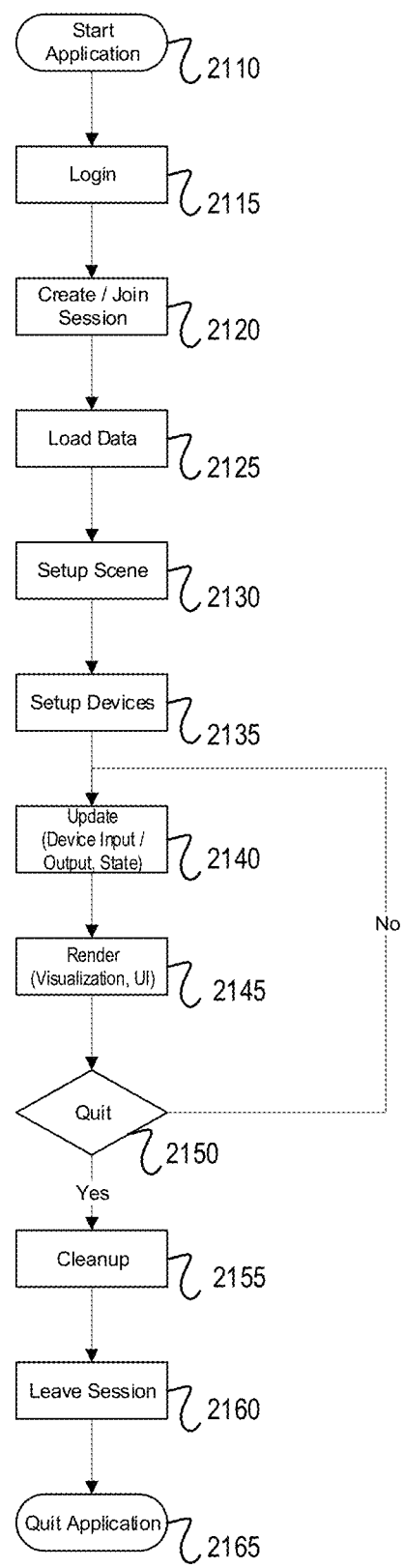
FIG. 21 shows a flow chart of an example embodiment of a method of application management in the AR system of FIG. 1A.

Referring now to FIG. 21, shown therein is a flow chart of an example embodiment of a method of application management 2100 in the AR system 100 of FIG. 1A. At 2110, the client device 170 receives a request to start an application. At 2115, the server 110 receives login credentials from a client device 170. The server 110 checks the credentials and returns access tokens that are required for any client requests or data access for auditing and authorization. At 2120, the server 110 creates a session or allows the user to join an existing session. The server 110 sends back success or failure to the client device 170 in a response. At 2125, the server 110 sends the specified data model 152 of the session to the client device 170, and the client device 170 loads data for the application. At 2130, the application 172 sets up a scene. At 2135, the application 172 sets up data devices. Data devices can be set up for communication and data streaming (e.g., camera device id, resolution, frame rate, IP address/device id of tracking system, which sensors to track, etc.) At 2140, the client device 170 updates the application 172, based on input/output data and/or state data. At 2145, the application 172 renders an image (e.g., visualization, UI). To render an image, a 3D model may contain graphics primitives and geometries that dictate how light/color should be displayed (e.g., specular, diffuse, ambient properties, vertex/face normals). The position/orientation of light, the camera, or the model may dictate the color and illumination at a particular instance in time, which may combine to compute a color value at the location, which can then be rasterized for display. At 2150, the method 2100 branches, depending on whether the user requests to quit the application 172. If the user does not request to quit the application, the method goes back to 2140. If the user requests to quit the application, the method goes to 2155. At 2155, the application 172 performs a cleanup. At 2160, the application 172 causes the user to leave the session. At 2165, the client device 170 quits the application.

Figure 22:
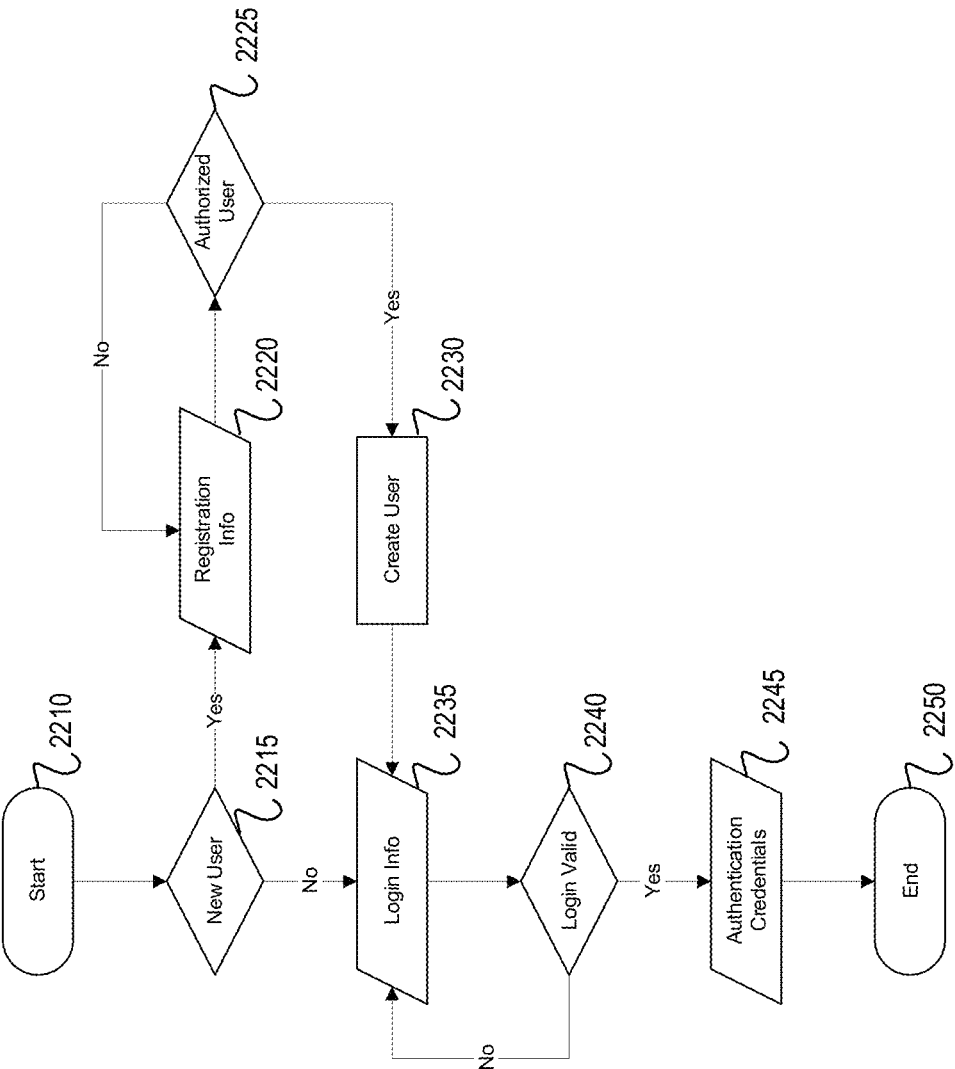
FIG. 22 shows a flow chart of an example embodiment of a method of login management in the AR system of FIG. 1A.

Referring now to FIG. 22, shown therein is a flow chart of an example embodiment of a method of login management 2200 in the AR system 100 of FIG. 1A. At 2210, the server 110 receives a request to start the login process. At 2215, the method 2200 branches depending on whether a new user is logging in. If it is a new user, the method 2200 continues at 2220. If it is not a new user, the method 2200 continues at 2235. At 2220, the server 110 receives registration information. At 2225, the method 2200 branches depending on whether the new user is authorized. If the new user is not authorized, the method 2200 returns to 2220. If the new user is authorized, the method 2200 continues to 2230. At 2230, the server 110 creates a new user profile. At 2235, the server 110 receives login information. At 2240, the method 2200 branches depending on whether the login is valid. If the login is not valid, the method 2200 returns to 2235. If the login is valid, the method 2200 continues to 2245. At 2245, the server 110 authenticates credentials for the user. At 2250, the server 110 ends the login process.

Figure 23:
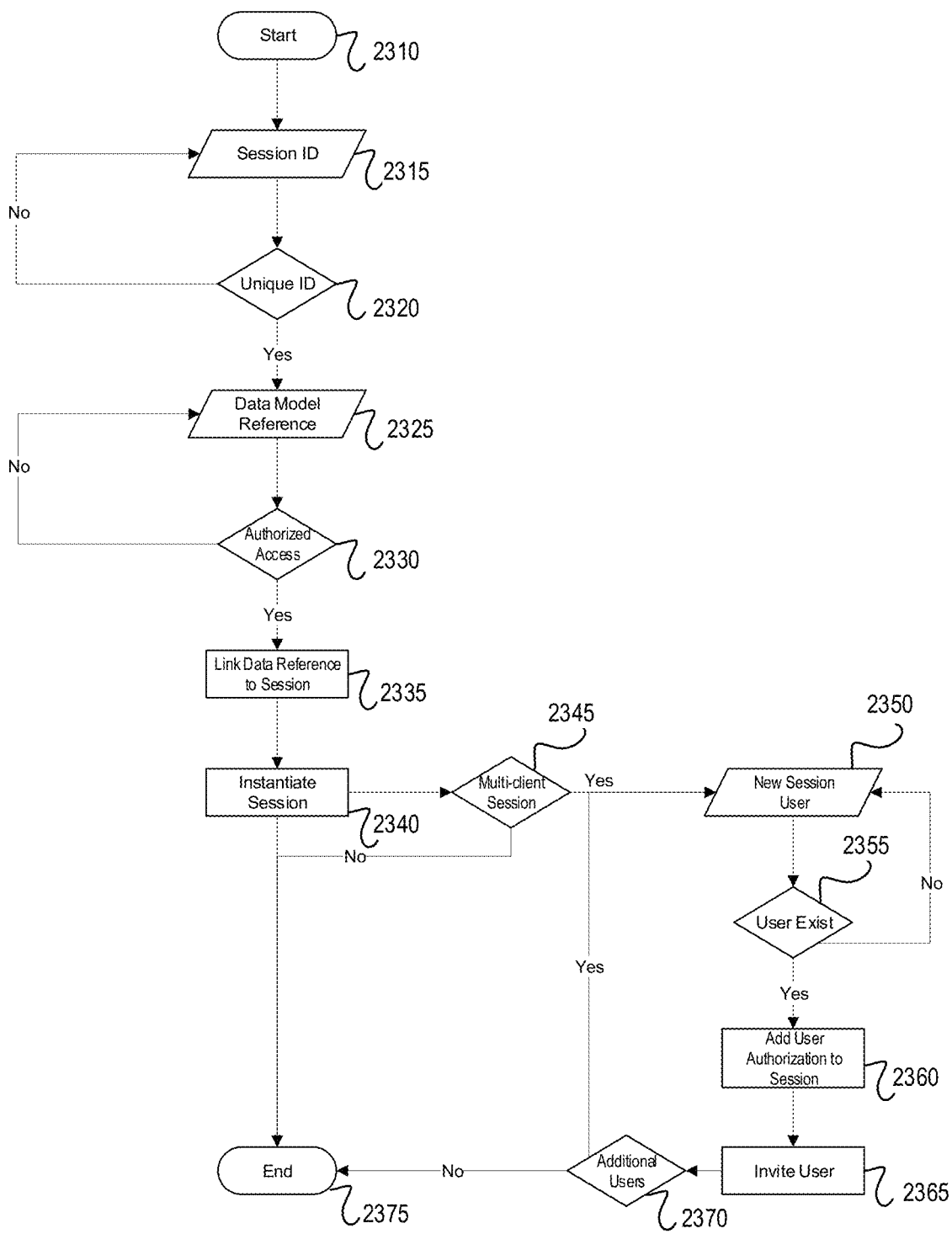
FIG. 23 shows a flow chart of an example embodiment of a method of session creation in the AR system of FIG. 1A.

Referring now to FIG. 23, shown therein is a flow chart of an example embodiment of a method of session creation 2300 in the AR system 100 of FIG. 1A. At 2310, the client device 170 receives a request to start the session creation process. At 2315, the server 110 receives a session ID from the application 172 (e.g., specified by a user) to create a session. At 2320, the method 2300 branches depending on whether the session ID is unique. If the session ID is not unique, the method 2300 returns to 2315. If the session ID is unique, the method 2300 proceeds to 2325. In at least one embodiment, a specified session ID is only allowed to contain alphanumeric characters. At 2325, the server 110 receives a data model reference for a data model 152 for the session through the application 172 (e.g., specified by the user). At 2330, the method 2300 branches depending on whether access is authorized. If access is not authorized, the method 2300 returns to 2325. If access is authorized, the method 2300 proceeds to 2335. Access is authorized if the user has access credentials to the specified data model 152. At 2335, the server 110 links the data model reference to the session. At 2340, the server 110 instantiates the session. At 2345, the method 2300 branches depending on whether it is a multi-client session 164. If it is not a multi-client session 164, the method 2300 goes to 2375. If it is a multi-client session 164, the method 2300 proceeds to 2350. At 2350, the client device 170 (e.g., as determined by the user) grants session access to another client device 170 of a specified user (i.e., a new session user) through application 172. At 2355, the method 2300 branches depending on whether the new session user exists. If the new session user does not exist, the method 2300 returns to 2350. If the new session user exists, the method 2300 proceeds to 2360. At 2360, the server 110 adds user authorization to the session. At 2365, the server 110 invites the user to the session. At 2370, the method 2300 branches depending on whether to add additional users. If there are additional users to add, the method 2300 returns to 2350. If there are not additional users to add, the method 2300 proceeds to 2375. At 2375, the client device 170 ends the session creation process.

Figure 24:
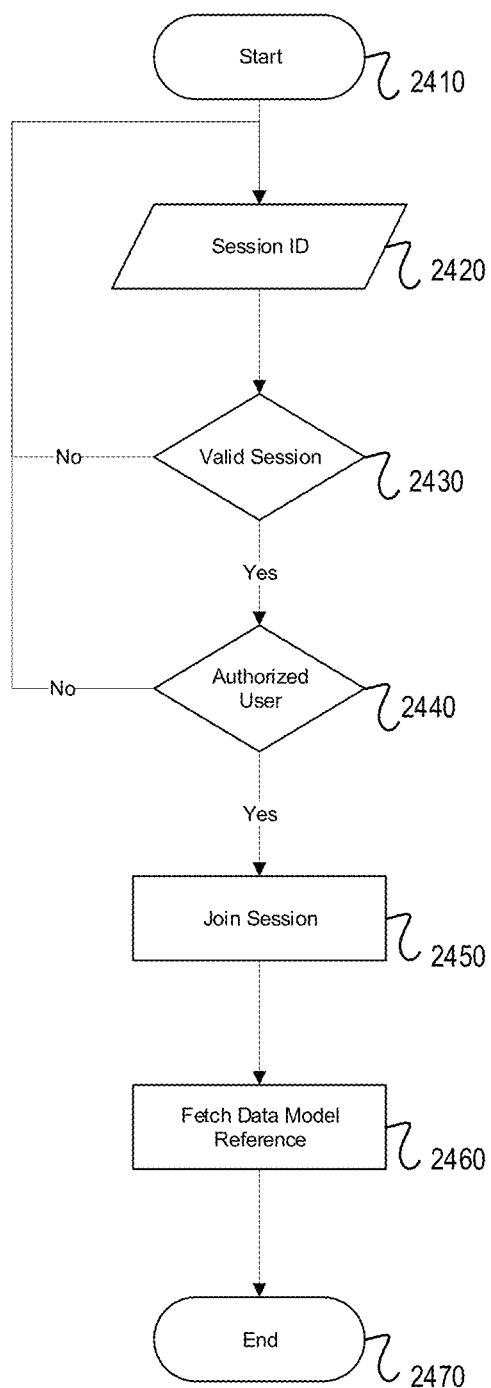
FIG. 24 shows a flow chart of an example embodiment of a method of session joining in the AR system of FIG. 1A.

Referring now to FIG. 24, shown therein is a flow chart of an example embodiment of a method for joining a session 2400 in the AR system 100 of FIG. 1A. At 2410, the client device 170 receives a request to start the session joining process. At 2420, the application 172 receives a session ID for a session from user input specified by the user at the client device 170. At 2430, the method 2400 branches depending on whether the session ID identifies a valid session. If it is not a valid session, the method 2400 returns to 2420. If it is a valid session, the method 2400 proceeds to 2440. The session ID is checked with the server 110. In at least one embodiment, a session is valid if there are no special characters in its identifier (i.e., only alphanumeric) and is open. At 2440, the method 2400 branches depending on whether an authorized user is trying to join the session. If it is not an authorized user, the method 2400 returns to 2420. If it is an authorized user, the method 2400 proceeds to 2450. The user on the client device 170 is an authorized user if the session creator had added them to the list of session users (e.g., as described in method 2300). At 2450, the server 110 allows the user to join the session. At 2460, the client device 170 fetches a data model reference for one of the data model records 152 through the server 110. At 2470, the client device 170 ends the session joining process.

Figure 25:
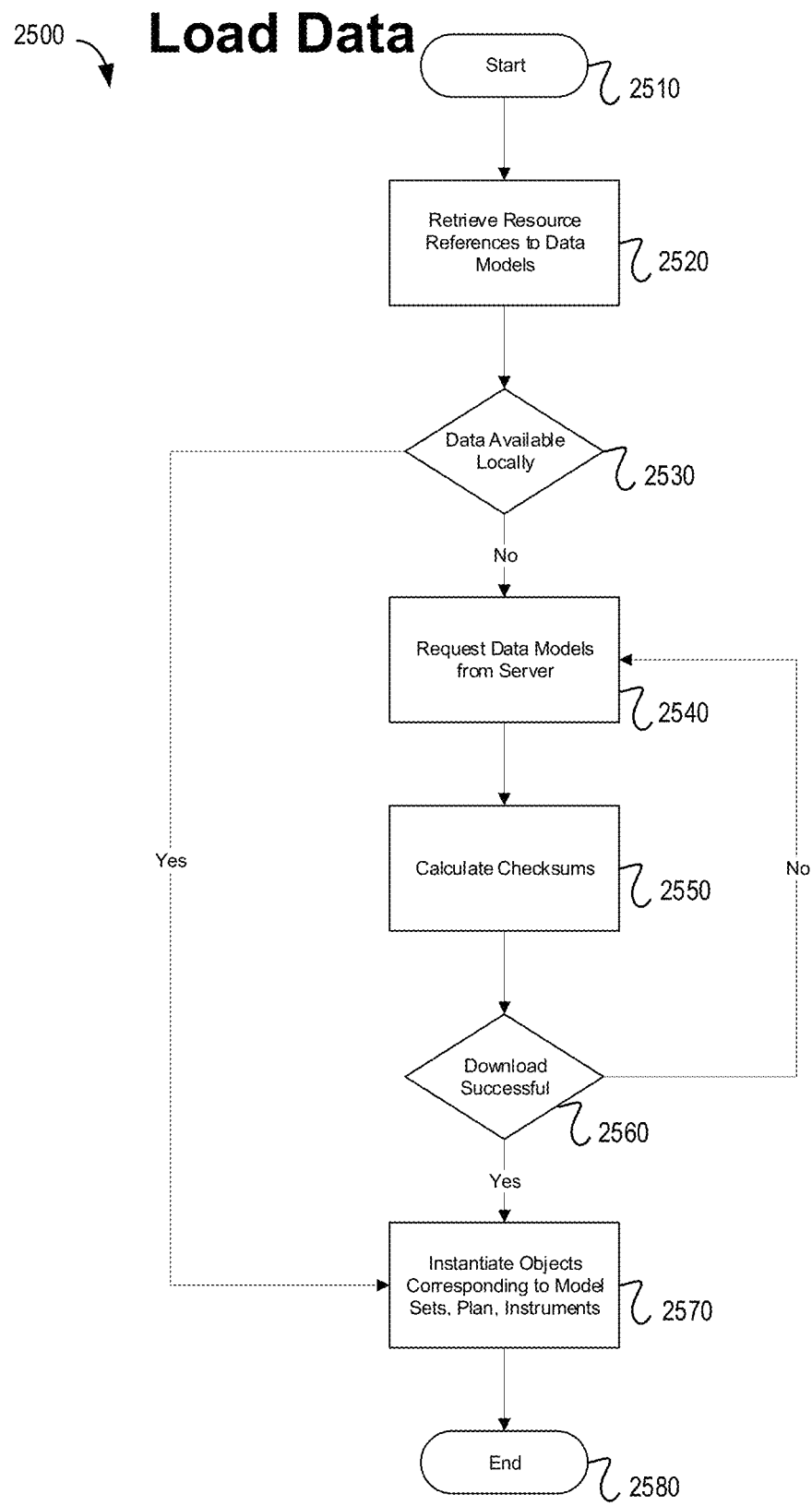
FIG. 25 shows a flow chart of an example embodiment of a method of data loading in the AR system of FIG. 1A.

Referring now to FIG. 25, shown therein is a flow chart of an example embodiment of a method of loading data 2500 in the AR system 100 of FIG. 1A. At 2510, the client device 170 receives a request to load data specified by the user. At 2520, the application 172 retrieves resource references (e.g., references to data in the database 150 as specified by a session creator, for example, as described in method 2300) to data models 152 as specified by the user. At 2530, the method 2500 branches depending on whether the data is available locally. If the data is not available locally, the method 2500 proceeds to 2540. If the data is available locally, the method 2500 goes to 2570. At 2540, the application 172 gets model data from the data models record 152 through the server 110. At 2550, the application 172 calculates checksums for the data received to make sure there is no error in data transmission. At 2560, the method 2500 branches depending on whether the data download was successful. If the data download was not successful, the method 2500 returns to 2540. If the data download was successful, the method 2500 proceeds to 2570. The data download is successful if all requested data are received and matches their checksum. Data not successfully retrieved (e.g., not matching checksum or failed) are re-requested. At 2570, the application 172 instantiates objects corresponding to the model sets data, the plans data, and/or the instruments data. At 2580, the client device 170 ends the data loading process.

Figure 26:
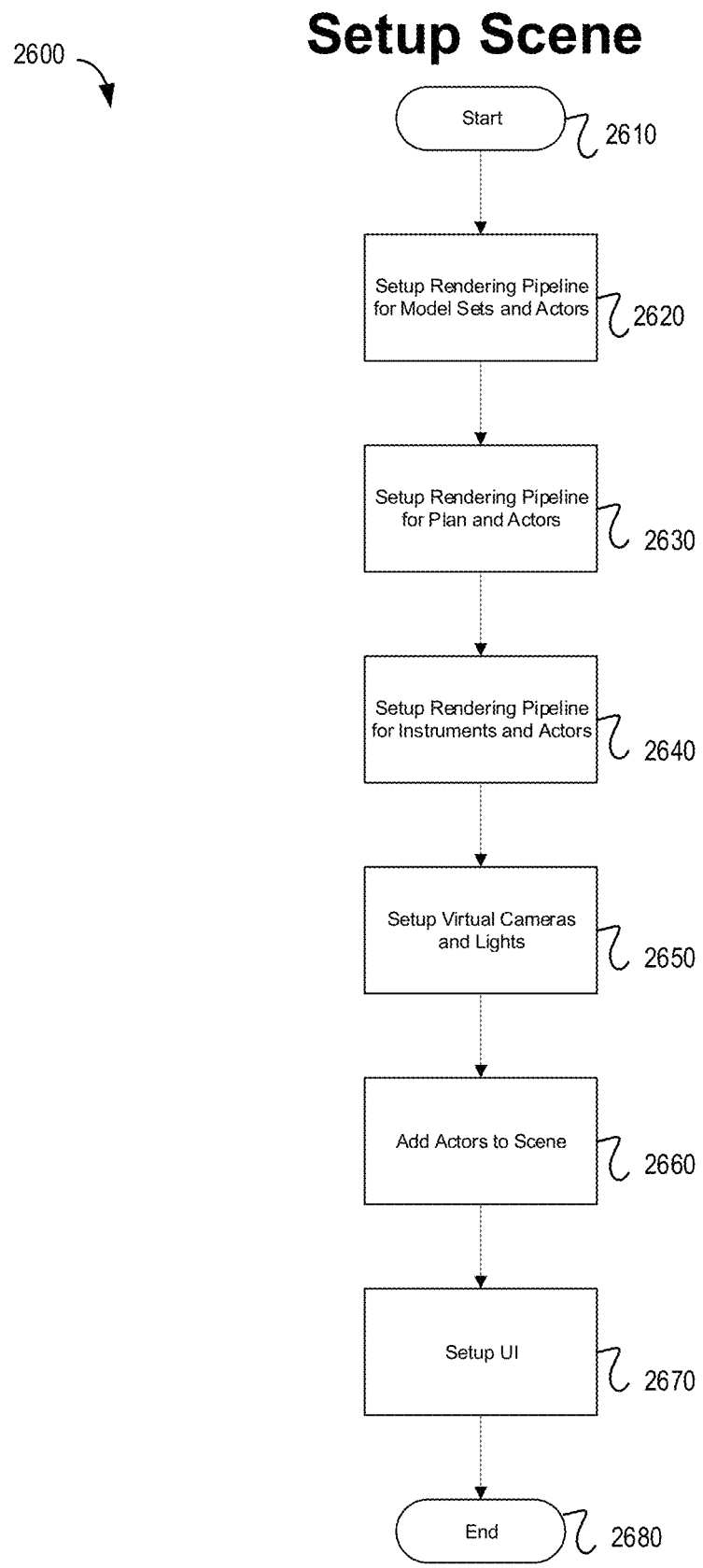
FIG. 26 shows a flow chart of an example embodiment of a method of setting up a scene in the AR system of FIG. 1A.

Referring now to FIG. 26, shown therein is a flow chart of an example embodiment of a method of setting up a scene 2600 in the AR system 100 of FIG. 1A. At 2610, the client device 170 receives a request to set up a scene which includes lights, camera, and actors for rendering. A scene may contain cameras, lights, and actors to be rendered by a graphics pipeline. At 2620, the application 172 sets up a rendering pipeline for model sets data and actors (i.e., for the model sets). At 2630, the application 172 sets up a rendering pipeline for plan data and actors (i.e., for the plan data). At 2640, the application 172 sets up a rendering pipeline for instruments data and actors (i.e., for the instruments). At 2650, the application 172 sets up virtual cameras and lights. At 2660, the application 172 adds actors to the scene. In at least one implementation, actors are not rendered and visible until added to the scene. At 2670, the application 172 sets up a UI. The application 172 may set up the UI programmatically or through a WYSIWYG editor of the framework used (such as Unity). At 2680, the client device 170 ends the scene setup process.

Figure 27:
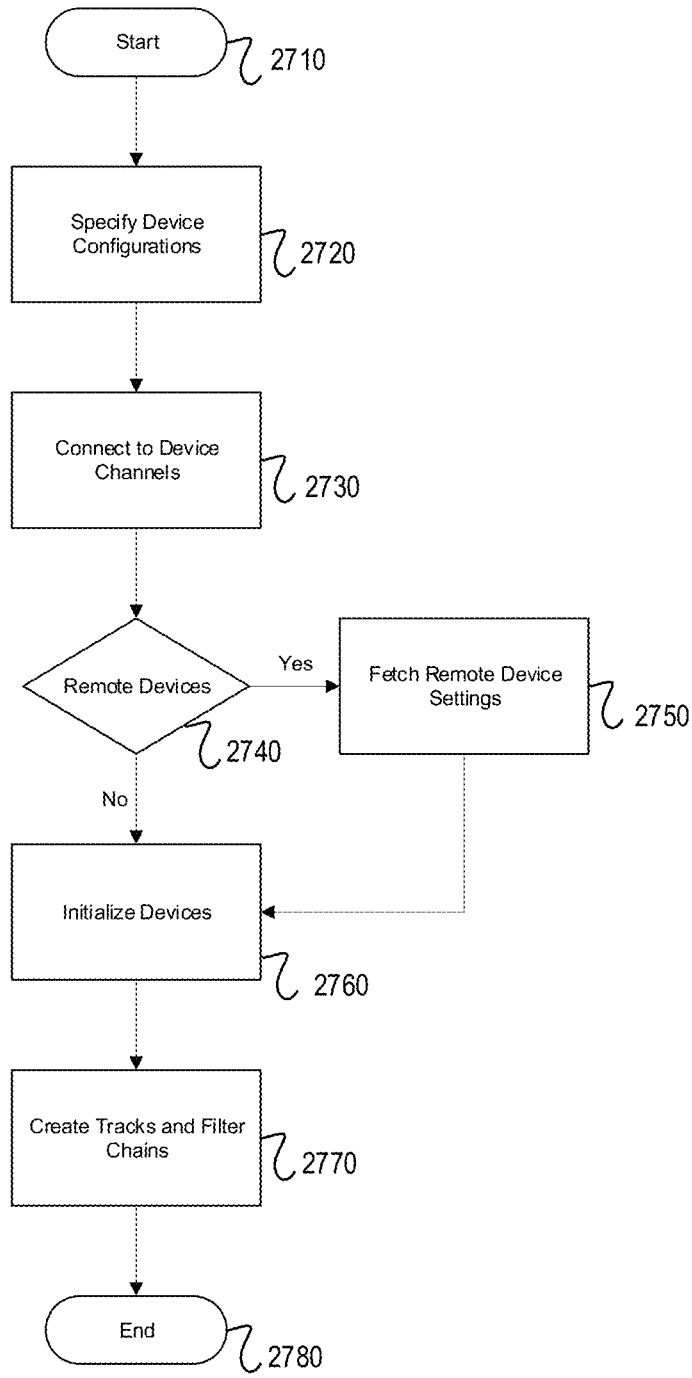
FIG. 27 shows a flow chart of an example embodiment of a method of setting up devices in the AR system of FIG. 1A.

Referring now to FIG. 27, shown therein is a flow chart of an example embodiment of a method of setting up data devices 2700 in the AR system 100 of FIG. 1A. For example, devices may need to be setup for data streaming (e.g., camera device id, resolution, frame rate, IP address/device id of tracking system, which sensors to track, etc.). At 2710, the client device 170 receives a request to start setting up devices. Setting up the device may be through the UI of the application 172. A user may initiate setting up devices for communication and data streaming. At 2720, the application 172 specifies device configurations. The device configurations include, for example, which devices are to be used and configured for use (e.g., camera device id, resolution, frame rate, IP address/device id of tracking system, which sensors to track, etc.). At 2730, the client device 170 connects the data devices to data device channels, allowing data to be sent to and received from other connected client devices 170 in a session. At 2740, the method 2700 branches depending on whether the devices 170 are remote. If the devices 170 are remote, the method 2700 proceeds to 2750. If the devices are not remote, the method 2700 goes to 2760. At 2750, the application 172 fetches remote device settings from the server 110. The remote device settings may include identifiers and settings required to receive data from a remote source—identifiers to know which remote devices are available and will stream data, and settings to receive data appropriately, such as width, height of video frame, and color space. At 2760, the application 172 initializes the devices. The application 172 may initiate devices to ready them for communication and receive data streams. At 2770, the application 172 creates tracks and filter chains 1064 using the tracks module 186. At 2780, the client device 170 ends the device setup process.

Figure 28:
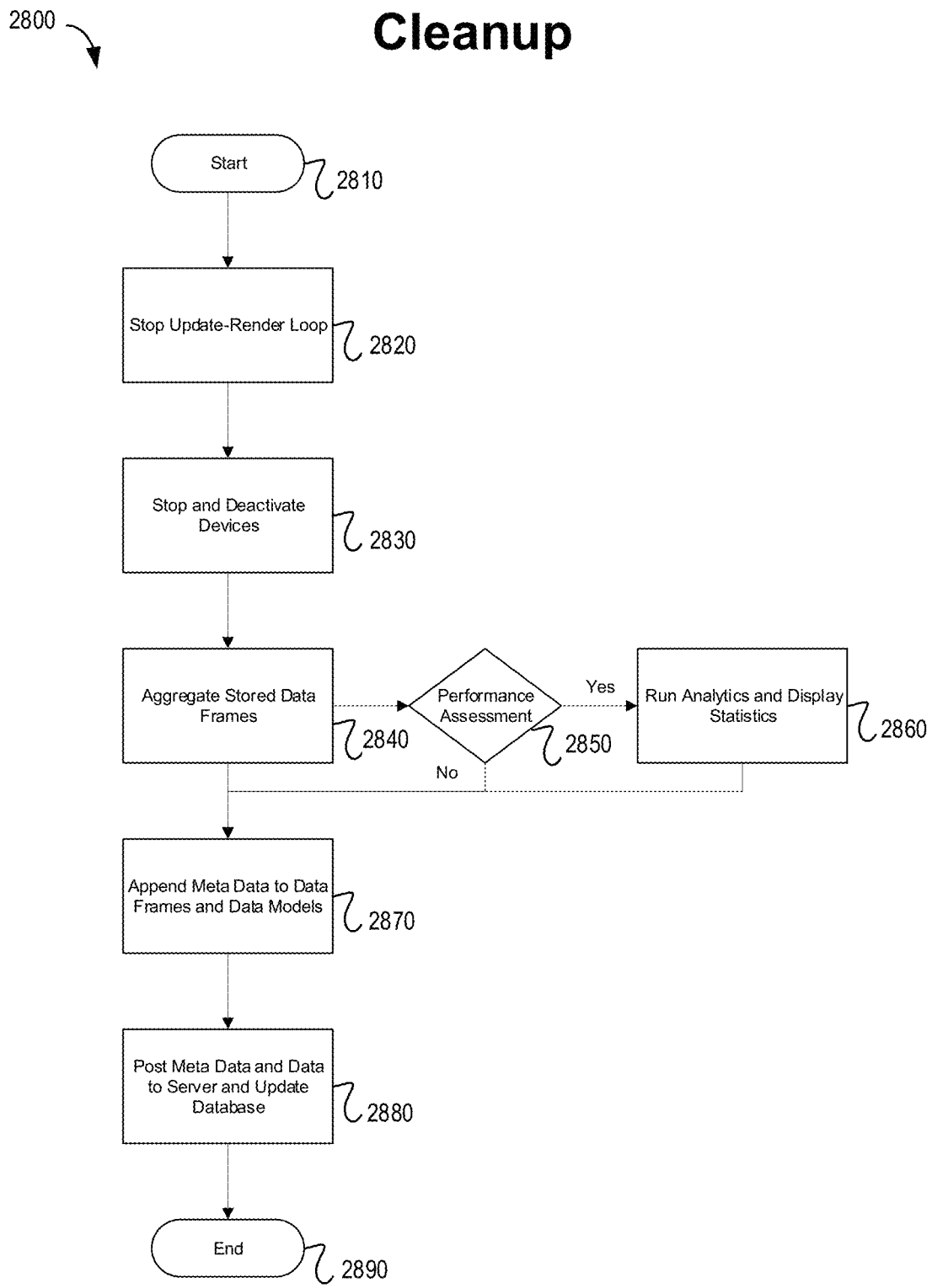
FIG. 28 shows a flow chart of an example embodiment of a method of application cleanup in the AR system of FIG. 1A.

Referring now to FIG. 28, shown therein is a flow chart of an example embodiment of a method of application cleanup 2800 in the AR system 100 of FIG. 1A. At 2810, the client device 170 receives a request to start application cleanup from the server 110. At 2820, the application 172 stops the update-render loop so that any acquired data is no longer used to update objects in the application 172 or used for rendering a scene. Objects used for rendering a scene are no longer re-rendered. At 2830, the application 172 stops and deactivates devices. Data is no longer streamed from local/remote devices or broadcasted to other clients in a session. At 2840, the application 172 aggregates stored data frames. Recorded data from specified data streaming devices are combined with settings of associated devices, timestamps, and device and data identifiers. For example, data may come from multiple devices, such as tracked hand data from a gesture interface or tracked surgical instruments from a tracking system. At 2850, the method 2800 branches depending on whether a performance assessment is requested (e.g., from a UI prompt to the user through the application 172). If a performance assessment is requested, the method 2800 proceeds to 2860. If a performance assessment is not requested, the method 2800 goes to 2870. At 2860, the server 110 or application 172 runs analytics and causes statistics to be displayed. The analytics may depend on, for example, the application context and individual or group statistics. The analytics may include amount of jitter in hand/instruments when performing a task, spatial deviation from a reference task (such as path of instrument or angle/distance to planned cut), and time taken to execute a task. At 2870, the application 172 appends metadata to data frames and data models 152. Appending the metadata may be done, for example, so that content adheres to FAIR principles (findable, accessible, interoperable, reusable). At 2880, the application 172 posts metadata and data recorded or modified to the server 110, which is used to update the database 150. At 2890, the client device 170 ends the application cleanup.

Figure 29:
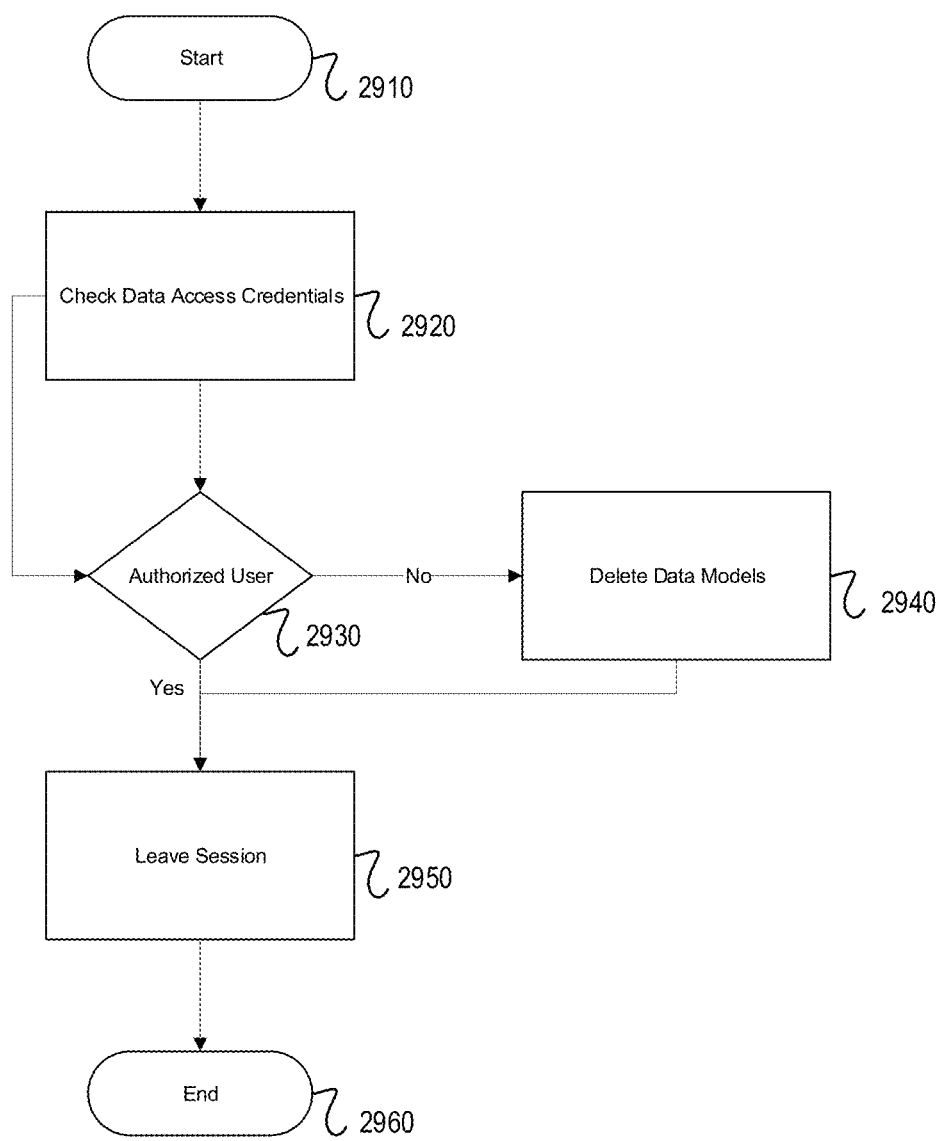
FIG. 29 shows a flow chart of an example embodiment of a method of leaving a session in the AR system of FIG. 1A.

Referring now to FIG. 29, shown therein is a flow chart of an example embodiment of a method of leaving a session 2900 in the AR system 100 of FIG. 1A. At 2910, the server 110 receives a request from a client device 170 (e.g., input by a user) to leave a session. At 2920, the server 110 checks data access credentials. If a user is not authorized to access data, then data should not persist on the client device 170. At 2930, the method 2900 branches depending on whether the user 162 is authorized. If the user 162 is not authorized, the method 2900 proceeds to 2940. If the user 162 is authorized, the method 2900 goes to 2950. At 2940, the client device 170 deletes data models 152. At 2950, the application 172 causes the user to leave the session on the client device 170. At 2960, the server 110 ends the process of leaving a session.

Figure 30:
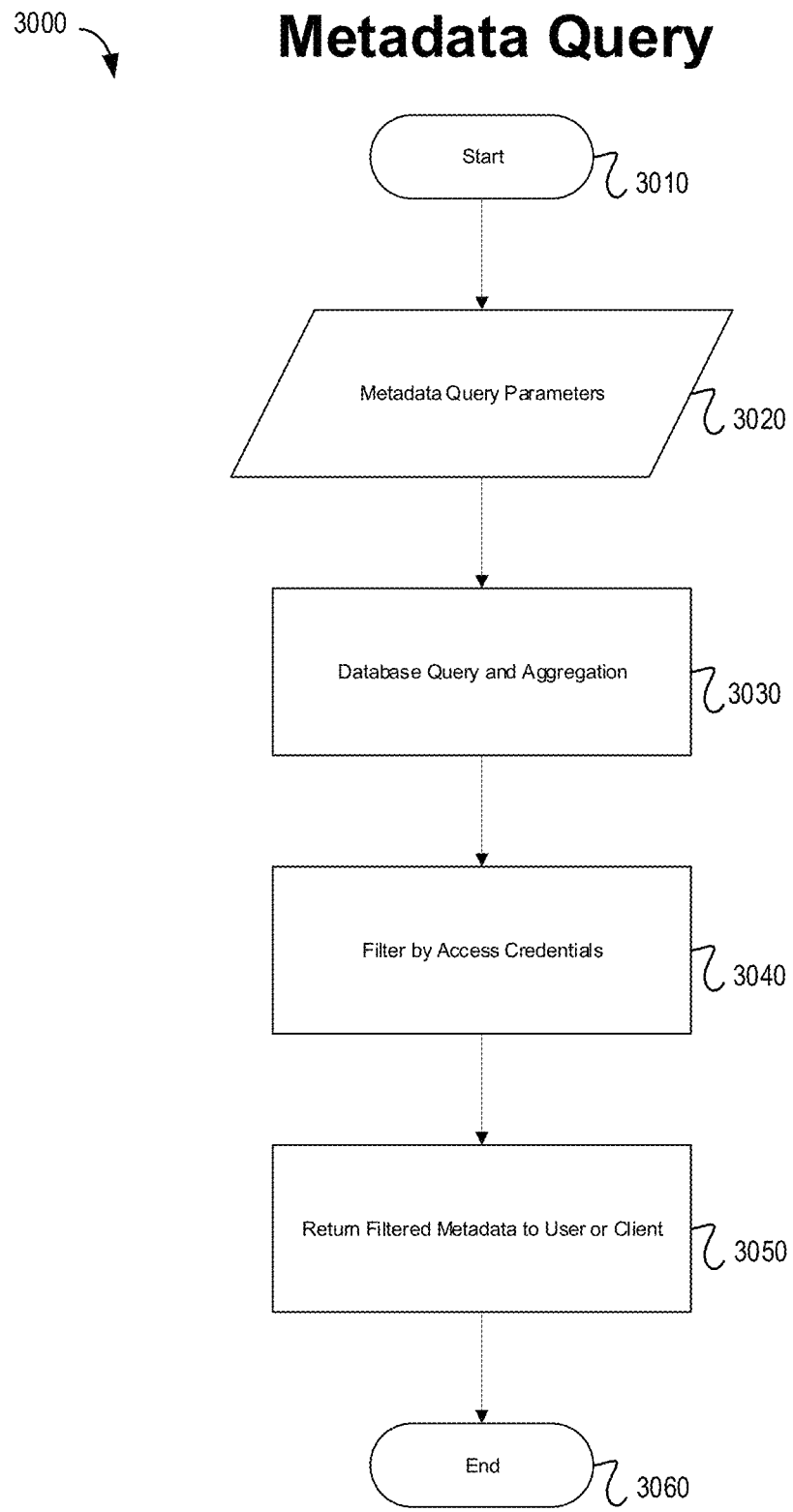
FIG. 30 shows a flow chart of an example embodiment of a method of querying metadata in the AR system of FIG. 1A.

Referring now to FIG. 30, shown therein is a flow chart of an example embodiment of a method of querying metadata 3000 in the AR system 100 of FIG. 1A. At 3010, the server 110 receives a metadata query request. At 3020, the server 110 parses the metadata query parameters. At 3030, the server 110 executes a database query to the database 150 and aggregates the metadata that is obtained from the database 150. At 3040, the server 110 filters the metadata by access credentials. The server preserves results that a client device 170 (e.g., used by a specific user) is authorized to access. At 3050, the server 110 returns filtered metadata to a user or a client. At 3060, the server 110 ends the metadata query.

Referring now to FIG. 41, shown therein is a flow chart of an example embodiment of a method 4100 of speech to text conversion in the AR system 100 of FIG. 1A. In method 4100, a client input mode is added to AR system 100 to improve usability. Along with the traditional keyboard input, a speech-to-text feature can be used. This application can be initialized by the client device 170. The client device 170 may use device-specific language processing algorithms, such as natural language processing (NLP), to detect the words in the input audio. A text string is built from this. Once the text has been created, it is displayed on the client device 170. The client device 170 may have the option of editing the text through the use of a traditional keyboard. Method 4100 may be added to complement features such as chat and annotation creation.

At 4110, the client device 170 receives audio input from a local user. At 4120, the client device 170 detects audio phonemes from the audio input. At 4130, the client device 170 carries out language processing on the detected audio phonemes to determine words that correspond to the audio phonemes. For example, the client device 170 may determine words by analyzing each audio phoneme using adjacent phonemes to determine the context and therefore what word it has the highest probability of being. At 4140, the client device 170 uses the processed audio words to create a string representation of the audio input. The server 110 sends the string representation (e.g., as raw text or formatted text) to the client device 170. At 4150, the client device 170 renders the string representation as text in a manner readable by the local user. Method 4100 can be divided into an update stage (e.g., 4110 to 4140) and a render stage (e.g., 4150), although method 4100 need not be so divided. In alternative implementations of method 4100, some or all acts carried out on the client device 170 may be carried out on the server 110, and vice versa (e.g., to speed up processing or to reduce network traffic).

Referring now to FIG. 42, shown therein is a flow chart of an example embodiment of a method 4200 of text to speech conversion in the AR system 100 of FIG. 1A. In method 4200, the audio features of the AR system 100 are expanded to include the reading of text from many features to the client devices 170. This may be accomplished through device specific language processing, such as natural language processing (NLP). The words are converted into sound clips that are then combined into an audio file that is then played. This feature facilitates features including instruction texts, chats, and annotation creation and viewing.

At 4210, the server 110 receives a request to generate audio output for a client device 170. At 4220, the server 110 parses text from the audio output to words. At 4230, the server 110 converts the words into sound clips. At 4240, the server 110 combines the sound clips into audio. The server 110 sends the audio (e.g., as raw audio signals or a formatted audio file) to the client device 170. At 4250, the client device 170 renders the audio in a manner listenable by a user. Method 4200 can be divided into an update stage (e.g., 4110 to 4140) and a render stage (e.g., 4150), although method 4200 need not be so divided. In alternative implementations of method 4200, some or all acts carried out on the server 110 may be carried out on the client device 170, and vice versa (e.g., to speed up processing or to reduce network traffic Experimental Results for Guided Osteotomy Saw bone phantoms generated from CT were used in AR navigated osteotomy. The data model consisted of the bone tumor volume contoured from CT (visible extent of disease) and a 5 mm extended planning volume to account for subclinical microscopic malignant lesions and uncertainty (registration and navigation accuracy). Planar cuts were planned around the planning volume for resection. Two participants executed two cuts on a bone phantom via AR guidance.

Rigid registration was performed using anatomical landmarks on the saw bone phantoms and their CT scans, with fiducial registration error (FRE) of 0.68 mm and 0.62 mm for the two bones respectively. Quantitative metrics for evaluation included distance to the planned cut, the instrument pitch angle to the planned cut, and instrument roll angle to the planned cut.

Figure 43:
FIG. 43 shows an example of visual feedback of misalignment during AR guidance of osteotomy.
Figure 44:
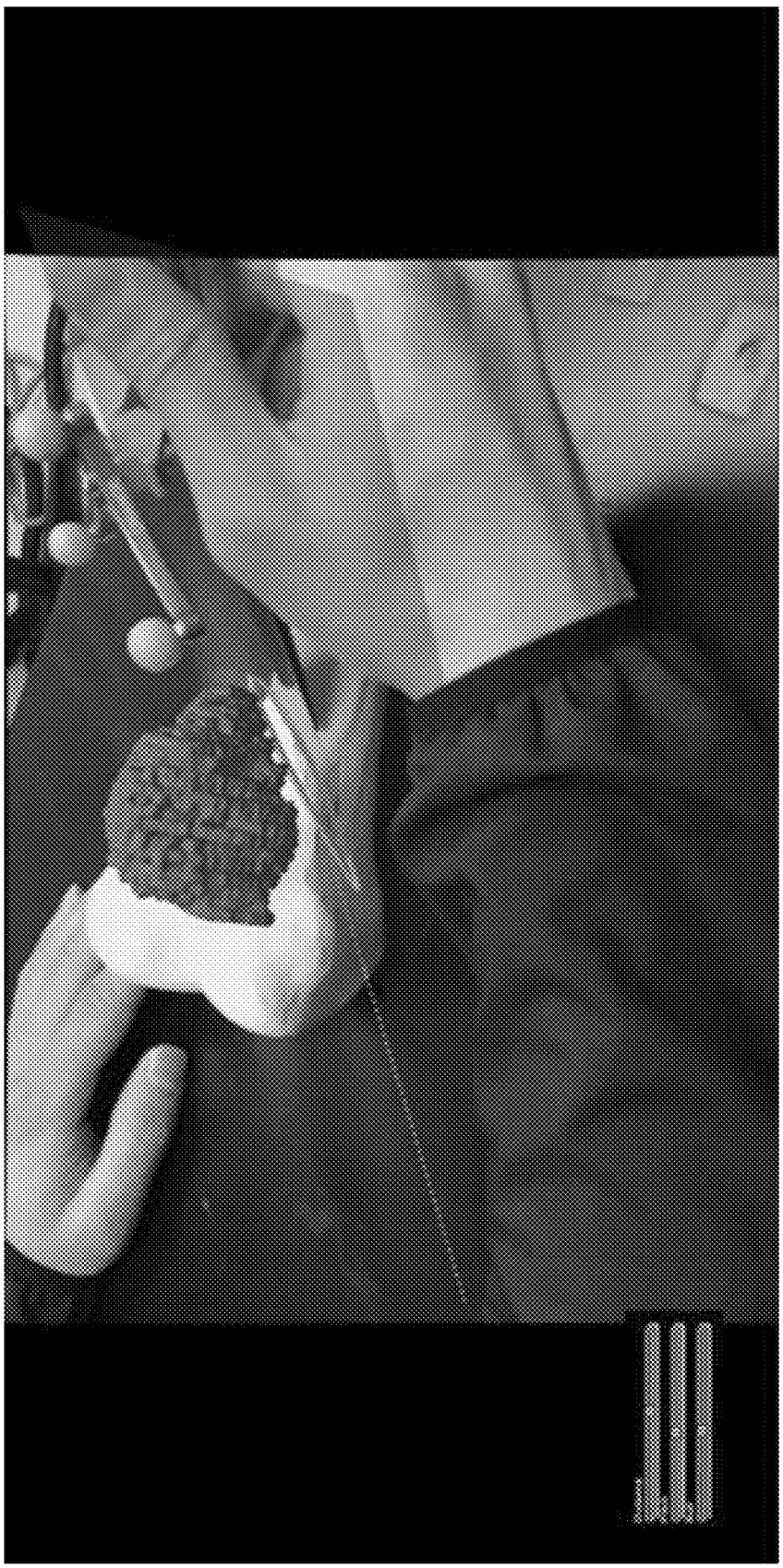
FIG. 44 shows an example of visual feedback of proper alignment during AR guidance of osteotomy.

The AR guidance visualized the tumor volume over real-time video feed along with the outline of the cut to be executed. A semi-transparent cutting plane was aligned with the movement of the tracked osteotome, where the current intersection of the blade with the anatomy was calculated in real time and visualized as an outline. This provided visual feedback as the user was able to visually identify when the cut was misaligned (shown in FIG. 43) or when they were aligned and were able to proceed with intervention (shown in FIG. 44). Distance, pitch, and roll sliders were also used to provide feedback to the user.

Post osteotomy, the saw bones were imaged using a flat panel Conebeam CT for registration and analysis. Post and pre CT scans were co-registered using anatomical landmarks. A best-plane fit was performed using sample points of the executed cuts, and pitch, roll, and distance were calculated against the planned cut. These results are shown in Table 1.

TABLE 1

AR guided osteotomy results on saw bone phantom

| Bone | Cut | Pitch (degrees) | Roll (degrees) | Distance (mm) |
|---|---|---|---|---|
| 1 | 1 | 0.36 | 9.03 | 3.51 |
| 1 | 2 | 1.75 | 10.67 | 0.89 |
| 2 | 1 | 8.47 | 1.36 | 1.53 |
| 2 | 2 | 5.31 | 3.06 | 0.25 |
| Average | | 3.97 | 6.03 | 1.54 |

Experimental Results for Needle Guidance 3D printed molds designed from CT tongue scans were used to cast silicon tongue phantoms for AR guidance using a needle instrument. Virtual targets and planned paths were defined in the CT scans of the silicon phantoms. Two participants performed needle insertion on the phantoms via AR guidance.

Rigid registration was performed using added fiducials on the silicon phantoms, resulting in FRE of 1.33 mm and 1.10 mm respectively. Quantitative metrics for evaluation included distance to target, distance to planned path, and angle to planned path.

Figure 45:
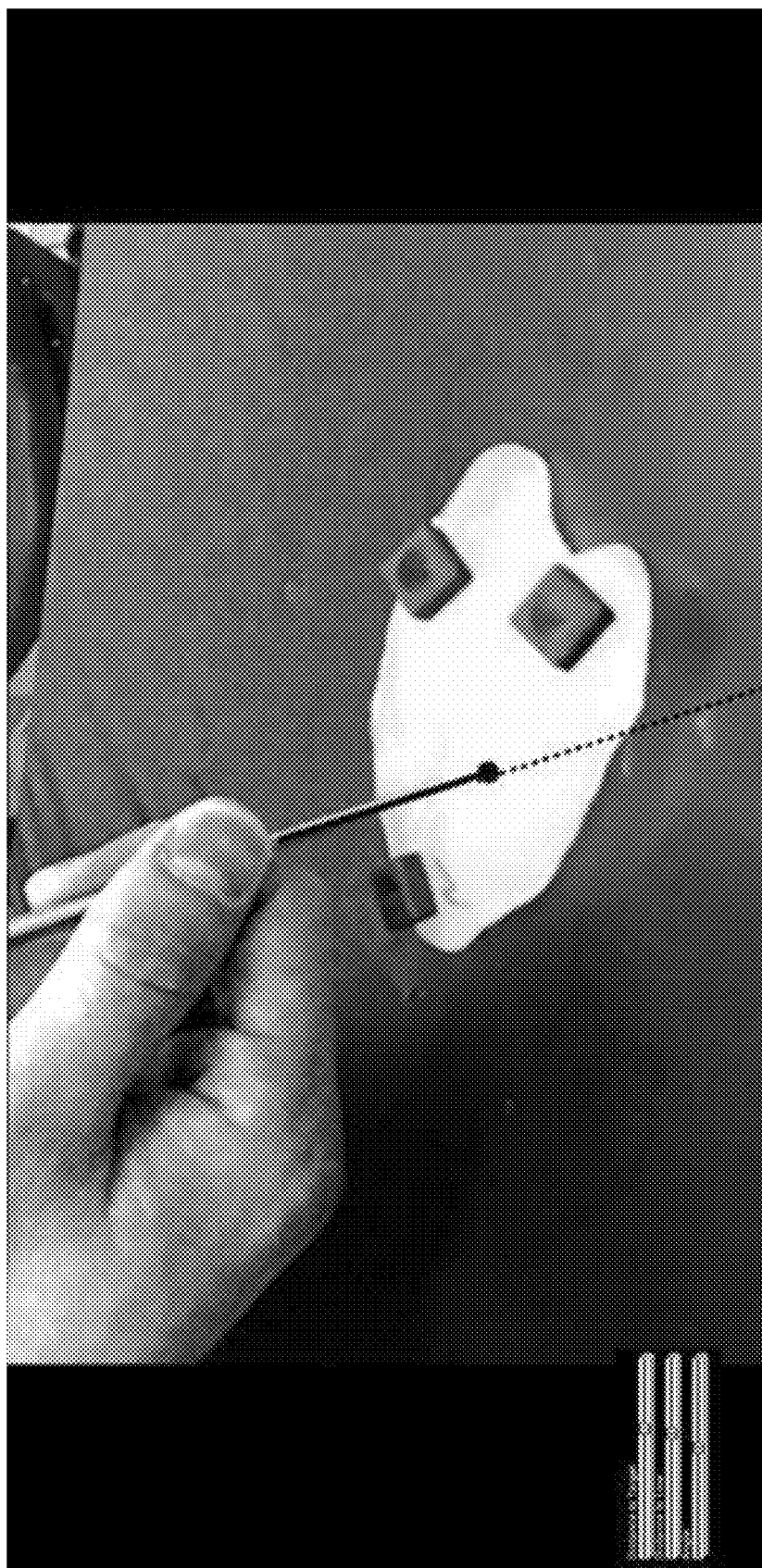
FIG. 45 shows an example of visual feedback during AR guidance of needle insertion.

AR guidance visualized the planned path and the target, trajectory of the tool, and visualization of the line between the tool tip and closest point on the planned path, which provided feedback to the user to visually minimize deviation before advancing the needle. FIG. 45 illustrates visual guidance where the solid line is the planned path, the sphere is the target, and the dashed line represents the trajectory of the needle.

The tracked needle path and final positions were recorded for angle and distance comparisons on the silicon phantom. These results are shown in Table 2.

TABLE 2

AR path guidance results on silicon tongue phantom

| Tongue | Distance to Target (mm) | Angle to Path (degrees) |
|---|---|---|
| 1 | 1.10 | 6.36 |
| 2 | 2.10 | 10.45 |
| Average | 1.60 | 8.41 |

While the applicant's teachings described herein are in conjunction with various embodiments for illustrative purposes, it is not intended that the applicant's teachings be limited to such embodiments as the embodiments described herein are intended to be examples. On the contrary, the applicant's teachings described and illustrated herein encompass various alternatives, modifications, and equivalents, without departing from the embodiments described herein, the general scope of which is defined in the appended claims.

The invention claimed is:

1. A computer-implemented method of guiding augmented reality (AR) intervention using a primary client device and a server, the primary client device having a first processor and a first input device, the method comprising:
   receiving, at the primary client device, model sets, an intervention plan having an intervention field, and session information about a session related to the AR intervention from the server;
   receiving, at the primary client device, first real-time input data from the first input device;
   generating, at the first processor, metrics by determining an evaluation of an execution of the intervention plan by comparing the intervention plan to the first real-time input data;
   displaying, on the primary client device, real-time graphics, based at least in part on the metrics, spatially over the intervention field;
   receiving, at the primary client device, real-time status data, from the server, about a replicate client device connected to the server after the replicate client device joins the session;
   sending, from the primary client device, the first real-time input data, through the server, to the replicate client device within the session;
   sending, from the primary client device, the metrics and the evaluation computed from the intervention plan, through the server, to the replicate client device within the session;
   receiving, at the primary client device, second real-time input data from the server, the second real-time input data originating from the replicate client device and relating to the intervention plan; and
   displaying, at the primary client device, real-time graphics based at least in part on the second real-time input data from the replicate client device.

2. The computer-implemented method of claim 1, wherein for remotely observing the guided AR intervention using the replicate client device having a second processor and a second input device, the method further comprises:
   receiving, at the replicate client device, the model sets, the intervention plan, and the session information about the session related to the AR intervention from the server;
   receiving, at the replicate client device, the first real-time input data, the metrics, and the evaluation broadcasted from the primary client device; and
   displaying, on the replicate client device, real-time graphics based at least in part on the model sets, the intervention plan, the first real-time input data, the metrics, and the evaluation.

3. The computer-implemented method of claim 2, wherein for providing remote mentoring of the guided AR intervention, the method further comprises:
   receiving, at the replicate client device, the second real-time input data from the second input device; and
   sending, from the replicate client device, the second real-time input data, through the server, to one or more additional replicate client devices connected to the server and the primary client device.

4. The computer-implemented method of claim 2, wherein for managing multi-user AR collaboration, the method further comprises:
   receiving, at the server, local user inputs from the replicate client device providing remote instructions;
   sending the local user inputs through the server to the primary client device;

displaying remote video input on the replicate client device in combination with the model sets and the intervention plan, the model sets including an underlying surface model;

executing, by the replicate client device, a pixel selection evaluator based at least in part on the local user inputs and the remote video input, thereby generating a first pixel selection output;

executing, by the replicate client device, a model selection evaluator based at least in part on the model sets and the first pixel selection output to map a pixel location in a render window to a 3D location of the underlying surface model, thereby generating a first model selection output;

rendering, on the replicate client device, first selected faces of the underlying surface model based at least in part on the first model selection output; and rendering, on the replicate client device, first traced pixels based at least in part on the first pixel selection output.

5. The computer-implemented method of claim 2, wherein for managing the multi-user AR collaboration at the primary client device performing the AR intervention, the method further comprises:

processing remote user inputs on the primary client device;

receiving local video input from the primary client device;

executing, by the primary client device, a pixel selection evaluator based at least in part on the remote user inputs and the local video input, thereby generating a second pixel selection output;

executing, by the primary client device, a model selection evaluator based at least in part on the model sets and the remote user inputs, thereby generating a second model selection output;

rendering audio instructions based at least in part on the remote user inputs at the primary client device;

rendering second selected faces based at least in part on the second pixel selection output at the primary client device; and rendering second traced pixels based at least in part on the second model selection output at the primary client device.

6. The computer-implemented method of claim 2, wherein to synchronize devices and tracks of the multi-user AR collaboration, the method further comprises:

storing the first real-time input data in a first buffer in corresponding first device tracks of the primary client device;

generating first clock ticks at the primary client device;

processing the first real-time input data in the first buffer through a first filter chain from the first clock ticks;

generating first data frames from the first filter chain;

receiving, at the server, the first data frames from the primary client device having a first set of corresponding time stamps determined from the first clock ticks;

storing the second real-time input data in a second buffer in corresponding second device tracks of the replicate client device;

generating second clock ticks at the replicate client device;

processing the second real-time input data in the second buffer through a second filter chain from the second clock ticks;

generating second data frames from the second filter chain;

receiving, at the server, the second data frames from the replicate client device having a second set of corresponding time stamps determined from the second clock ticks;

generating, at the server, combined data frames based at least in part on the first data frames and the second data frames along with the first set of corresponding time stamps and the second set of corresponding time stamps; and storing the combined data frames in a database.

7. The computer-implemented method of claim 2, further comprising:

retrieving, by the server, the combined data frames from the database;

generating, by the server, output clock ticks;

extracting, by the server, a primary client data frame and a primary client time stamp from the combined data frames for the primary client device corresponding to a current output clock tick;

extracting, by the server, a replicate client data frame and a replicate client time stamp from the combined data frames for the replicate client device corresponding to the current output clock tick;

combining, by the server, extracted data frames of the primary client device and the replicate client device between server time stamps corresponding to current and previous output clock ticks; and broadcasting, by the server, the combined data frames along with corresponding time stamps to the primary client device and the replicate client device.

8. The computer-implemented method of claim 2, wherein for guiding geometric resection by AR visualization, the method further comprises:

obtaining, by the server, a plurality of resection planes from the intervention plan;

obtaining, by a client device, a plurality of active cut planes from a tracked instrument from one of the first real-time input data or the second real-time input data;

determining, by the client device, the evaluation by comparing at least one of the plurality of active cut planes to at least one of the plurality of resection planes;

calculating, by the client device, the metrics to determine at least one of angle offset and tip-to-plane distance;

calculating, by the client device, the faces of the surface model that intersects with the plane of the tracked instrument; and producing, by the client device, the AR visualization by generating the trajectory of the tracked instrument, outlining an intersection of one of the plurality of active cut planes and the model set, and displaying a color-coded angle offset and a tip-to-plane distance to indicate precision, wherein the client device is the primary client device or the replicate client device.

9. The computer-implemented method of claim 2, wherein for guiding needle placement by AR visualization, the method further comprises:

obtaining, by the server, a plurality of line trajectories from the intervention plan, each of the line trajectories comprising an entrance point and a target point;

obtaining, by a client device, a plurality of active instrument line placements from a tracked instrument from one of the first real-time input data or the second real-time input data;

determining, by the client device, the evaluation by comparing at least one of the plurality of active instrument line placements to at least one of the plurality of line trajectories;

calculating, by the client device, the metrics to determine at least one of tip-to-trajectory distance, tip-to-target distance, and instrument-to-trajectory angle;

calculating, by the client device, the closest point between the tracked instrument tip and the planned trajectory; and producing, by the client device, the AR visualization by generating a trajectory of the tracked instrument, generating an intersection of a trajectory of the tracked instrument with the target point, generating a line between a tip of the tracked instrument and a planned line trajectory, and displaying a color-coded tip-to-trajectory distance, a tip-to-target distance, and an instrument-to-trajectory angle to indicate precision, wherein the client device is the primary client device or the replicate client device.

10. The computer-implemented method of claim 2 wherein for displaying critical structure avoidance by AR visualization, the method further comprises:

obtaining, by the server, a first image of an intervention target and a critical structure image of the intervention target from the intervention plan;

obtaining, by a client device, a plurality of tool placements from one of the first real-time input data or the second real-time input data from a tracked instrument;

determining, by the client device, the evaluation by comparing at least one of the plurality of tool placements to a no-fly zone obtained from an overlay of the critical structure image on the first image;

calculating, by the client device, the metrics to determine an incidence of the at least one of the plurality of tool placements with the no-fly zone; and displaying the AR visualization on the client device by showing in-field alerts indicating placement or trajectory of the tracked instrument intersecting with the no-fly zone, wherein the client device is the primary client device or the replicate client device.

11. A system for performing guiding augmented reality (AR) intervention for planning, intervention, guidance, and/or education for medical applications, wherein the system comprises:

a server including:
  a database having:
    a plurality of data models that each have a plurality of model set records, a plurality of plans records, a plurality of recordings records, and a plurality of instruments records;
    a plurality of user records; and
    a plurality of session records; and
  at least one processor that is operatively coupled to the database and configured to execute program instructions for implementing:
    an HTTP server for providing endpoints for queries and delivery of content, user authentication, and management of sessions; and
    a WebSocket server to enable multi-client broadcast of data across device specific listening channels by setting up WebSocket clients; and a primary client device that is communicatively coupled to the server to interact with the HTTP server and the WebSocket server, the primary client device including a first processor and a first input device, the primary client device being configured to:

receive model sets, an intervention plan having an intervention field, and session information about a session related to the AR intervention from the server;

receive first real-time input data from the first input device;

generate metrics by determining an evaluation of an execution of the intervention plan by comparing the intervention plan to the first real-time input data;

display real-time graphics, based at least in part on the metrics, spatially over the intervention field;

receive real-time status data, from the server, about a replicate client device connected to the server after the replicate client device joins the session;

send the first real-time input data, through the server, to the replicate client device within the session;

send the metrics and the evaluation computed from the intervention plan, through the server, to the replicate client device within the session;

receive second real-time input data from the server, the second real-time input data originating from the replicate client device and relating to the intervention plan; and display real-time graphics based at least in part on the second real-time input data from the replicate client device.

12. The system of claim 11, wherein the system further comprises the replicate client device, the replicate client device having a second processor and a second input device, wherein for remotely observing the guided AR intervention the replicate client device is configured to:

receive the model sets, the intervention plan, and the session information about the session related to the AR intervention from the server;

receive the first real-time input data, the metrics, and the evaluation broadcasted from the primary client device; and display real-time graphics based at least in part on the model sets, the intervention plan, the first real-time input data, the metrics, and the evaluation.

13. The system of claim 12, wherein for providing remote mentoring of the guided AR intervention:

the replicate client device is configured to:
  receive the second real-time input data from the second input device; and
  send the second real-time input data, through the server, to one or more additional replicate client devices connected to the server and the primary client device.

14. The system of claim 12, wherein for managing multi-user AR collaboration:

the server is configured to receive local user inputs from the replicate client device providing remote instructions and send the local user inputs to the primary client device; and the replicate client device is configured to:
  display remote video input in combination with the model sets and the intervention plan, the model sets including an underlying surface model;
  execute a pixel selection evaluator based at least in part on the local user inputs and the remote video input, thereby generating a first pixel selection output;
  execute a model selection evaluator based at least in part on the model sets and the first pixel selection output to map a pixel location in a render window to a 3D location of the underlying surface model, thereby generating a first model selection output;

render first selected faces of the underlying surface model based at least in part on the first model selection output; and render first traced pixels based at least in part on the first pixel selection output.

15. The system of claim 12, wherein for managing the multi-user AR collaboration at the primary client device performing the AR intervention, the primary client device is configured to:

process remote user inputs;

receive local video input;

execute a pixel selection evaluator based at least in part on the remote user inputs and the local video input, thereby generating a second pixel selection output;

execute a model selection evaluator based at least in part on the model sets and the remote user inputs, thereby generating a second model selection output;

render audio instructions based at least in part on the remote user inputs;

render second selected faces based at least in part on the second pixel selection output; and render second traced pixels based at least in part on the second model selection output.

16. The system of claim 12, wherein to synchronize devices and tracks of the multi-user AR collaboration:

the primary client device is configured to:

store the first real-time input data in a first buffer in corresponding first device tracks of the primary client device;

generate first clock ticks;

process the first real-time input data in the first buffer through a first filter chain from the first clock ticks; and generate first data frames from the first filter chain;

the replicate client device is configured to:

store the second real-time input data in a second buffer in corresponding second device tracks of the replicate client device;

generate second clock ticks at the replicate client device;

process the second real-time input data in the second buffer through a second filter chain from the second clock ticks; and generate second data frames from the second filter chain; and the server is configured to:

receive, from the primary client device, the first data frames having a first set of corresponding time stamps determined from the first clock ticks;

receive the second data frames from the replicate client device having a second set of corresponding time stamps determined from the second clock ticks; and generate combined data frames based at least in part on the first data frames and the second data frames along with the first set of corresponding time stamps and the second set of corresponding time stamps; and store the combined data frames in a database.

17. The system of claim 12, wherein the server is further configured to:

retrieve the combined data frames from the database;

generate output clock ticks;

extract a primary client data frame and a primary client time stamp from the combined data frames for the primary client device corresponding to a current output clock tick;

extract a replicate client data frame and a replicate client time stamp from the combined data frames for the replicate client device corresponding to the current output clock tick;

combine extracted data frames of the primary client device and the replicate client device between server time stamps corresponding to current and previous output clock ticks; and broadcast the combined data frames along with corresponding time stamps to the primary client device and the replicate client device.

18. The system of claim 12, wherein for guiding geometric resection by AR visualization:

the server is configured to obtain a plurality of resection planes from the intervention plan and send the plurality of resection planes to a client device; and the client device is configured to:

obtain a plurality of active cut planes from a tracked instrument from one of the first real-time input data or the second real-time input data;

determine the evaluation by comparing at least one of the plurality of active cut planes to at least one of the plurality of resection planes;

calculate the metrics to determine at least one of angle offset and tip-to-plane distance;

calculate the faces of the surface model that intersects with the plane of the tracked instrument; and produce the AR visualization by generating the trajectory of the tracked instrument, outlining an intersection of one of the plurality of active cut planes and the model set, and displaying a color-coded angle offset and a tip-to-plane distance to indicate precision, wherein the client device is the primary client device or the replicate client device.

19. The system of claim 12, wherein for guiding needle placement by AR visualization:

the server is configured to obtain and send a plurality of line trajectories from the intervention plan to a client device, where each of the line trajectories comprise an entrance point and a target point; and the client device is configured to:

obtain a plurality of active instrument line placements from a tracked instrument from one of the first real-time input data or the second real-time input data;

determine the evaluation by comparing at least one of the plurality of active instrument line placements to at least one of the plurality of line trajectories;

calculate the metrics to determine at least one of tip-to-trajectory distance, tip-to-target distance, and instrument-to-trajectory angle;

calculate the closest point between the tracked instrument tip and the planned trajectory; and produce the AR visualization by generating a trajectory of the tracked instrument, generating an intersection of a trajectory of the tracked instrument with the target point, generating a line between a tip of the tracked instrument and a planned line trajectory, and displaying a color-coded tip-to-trajectory distance, a tip-to-target distance, and an instrument-to-trajectory angle to indicate precision, wherein the client device is the primary client device or the replicate client device.

20. The system of claim 12 wherein for displaying critical structure avoidance by AR visualization:
the server is configured to obtain and send a first image of an intervention target and a critical structure image of the intervention target from the intervention plan to a client device; and
the client device is configured to:
obtain a plurality of tool placements from one of the first real-time input data or the second real-time input data from a tracked instrument;
determine the evaluation by comparing at least one of the plurality of tool placements to a no-fly zone obtained from an overlay of the critical structure image on the first image;
calculate the metrics to determine an incidence of the at least one of the plurality of tool placements with the no-fly zone; and
display the AR visualization on the client device by showing in-field alerts indicating placement or trajectory of the tracked instrument intersecting with the no-fly zone,
wherein the client device is the primary client device or the replicate client device.

\* \* \* \* \*